US009220838B2

(12) United States Patent
Soma et al.

(10) Patent No.: US 9,220,838 B2
(45) Date of Patent: Dec. 29, 2015

(54) PUNCTURE DEVICE

(71) Applicant: TERUMO KABUSHIKI KAISHA, Shibuya-ku (JP)

(72) Inventors: Takahiro Soma, Kanagawa (JP); Hiromasa Kohno, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/225,074

(22) Filed: Mar. 25, 2014

(65) Prior Publication Data

US 2014/0228759 A1 Aug. 14, 2014

Related U.S. Application Data

(63) Continuation of application No. PCT/JP2012/075276, filed on Sep. 24, 2012.

(30) Foreign Application Priority Data

Sep. 26, 2011 (JP) ................................. 2011-209978
Sep. 26, 2011 (JP) ................................. 2011-209980

(51) Int. Cl.
*A61M 5/142* (2006.01)
*A61M 1/36* (2006.01)
(Continued)

(52) U.S. Cl.
CPC ............. *A61M 5/14248* (2013.01); *A61M 1/36* (2013.01); *A61M 5/158* (2013.01); *A61M 5/20* (2013.01);
(Continued)

(58) Field of Classification Search
CPC ......... A61M 2005/14252; A61M 2005/14284; A61M 2005/14256; A61M 2005/14268; A61M 2005/1581; A61M 2005/1583; A61M 2005/1585; A61M 2005/1586; A61M 2005/1587; A61M 25/0606; A61M 25/0612; A61M 25/0625; A61M 25/0631
See application file for complete search history.

(56) References Cited

U.S. PATENT DOCUMENTS

| 2002/0123740 | A1* | 9/2002 | Flaherty et al. ............. 604/890.1 |
| 2007/0282269 | A1 | 12/2007 | Carter et al. |
| 2008/0051714 | A1* | 2/2008 | Moberg et al. ................ 604/135 |
| 2008/0077081 | A1 | 3/2008 | Mounce et al. |
| 2009/0018495 | A1 | 1/2009 | Panduro |

(Continued)

FOREIGN PATENT DOCUMENTS

| JP | 2008-546496 A | 12/2008 |
| JP | 2009-101217 A | 5/2009 |
| JP | 2009-538693 A | 11/2009 |
| JP | 2009-539444 A | 11/2009 |

(Continued)

OTHER PUBLICATIONS

International Search Report (PCT/ISA/210) mailed on Jan. 8, 2013, by the Japanese Patent Office as the International Searching Authority for International Application No. PCT/JP2012/075276.

*Primary Examiner* — Bhisma Mehta
*Assistant Examiner* — James Ponton
(74) *Attorney, Agent, or Firm* — Buchanan Ingersoll & Rooney PC

(57) ABSTRACT

A puncture device comprising a hollow needle, a fixing portion fixed to the hollow needle, a sheath portion covering a part/entirety of the hollow needle and including a plastically deformable elongating member, a holding portion holding the hollow needle and the sheath portion in an integrated manner, with the holding portion positioned between the tip portion of the hollow needle and the plastically deformable elongating member, a holding release mechanism that releases the holding of the holding portion between the hollow needle and the sheath portion after the hollow needle and the sheath portion puncture the living body. The sheath portion elongates and is held in an elongated condition when the holding portion moves by the holding release mechanism, or when the holding of the hollow needle using the holding portion in an integrated manner is released, and the elastic portion contracts.

5 Claims, 32 Drawing Sheets

(51) Int. Cl.
*A61M 5/20* (2006.01)
*A61M 5/158* (2006.01)
*A61M 25/06* (2006.01)
*A61M 5/14* (2006.01)

(52) U.S. Cl.
CPC ... *A61M 25/0606* (2013.01); *A61M 2005/1401* (2013.01); *A61M 2005/14252* (2013.01); *A61M 2005/14268* (2013.01); *A61M 2005/1585* (2013.01); *A61M 2205/10* (2013.01)

(56) References Cited

U.S. PATENT DOCUMENTS

2009/0099521 A1\* 4/2009 Gravesen et al. ............ 604/136
2009/0254041 A1 10/2009 Krag et al.

FOREIGN PATENT DOCUMENTS

JP 2010-501283 A 1/2010
WO WO 2008/024814 A 2/2008

\* cited by examiner

FIG. 4
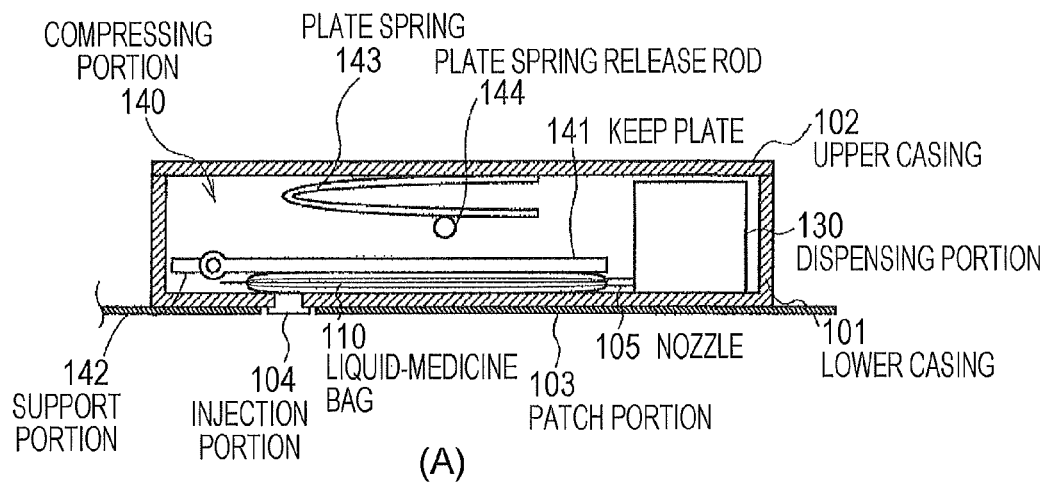
(A)
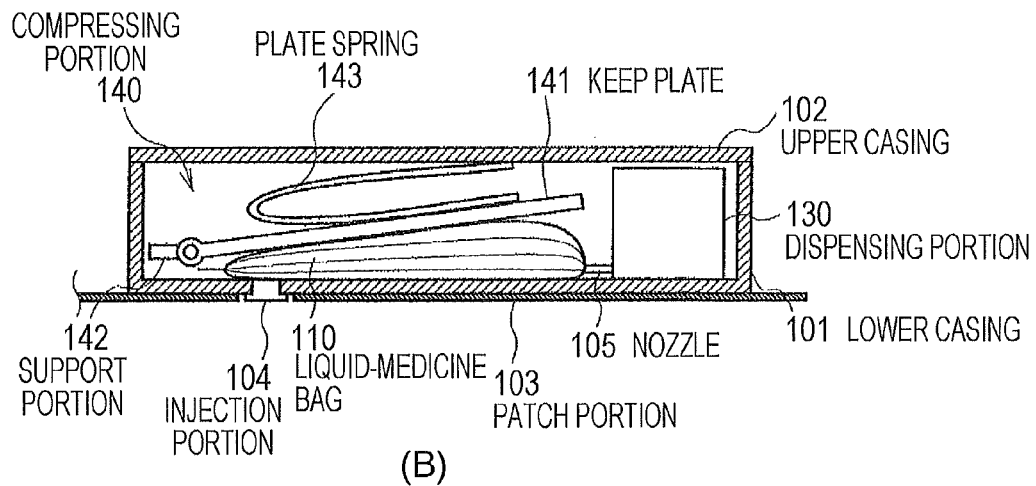
(B)

FIG. 7
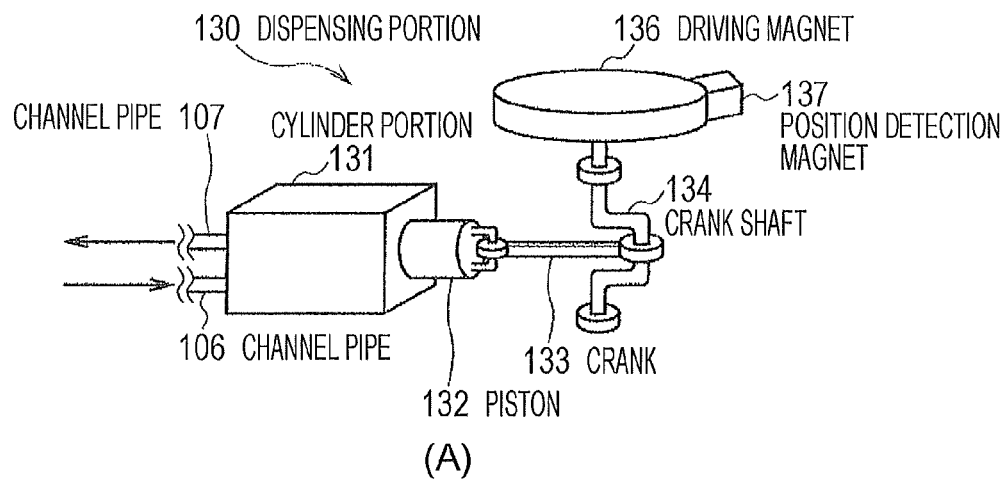
(A)
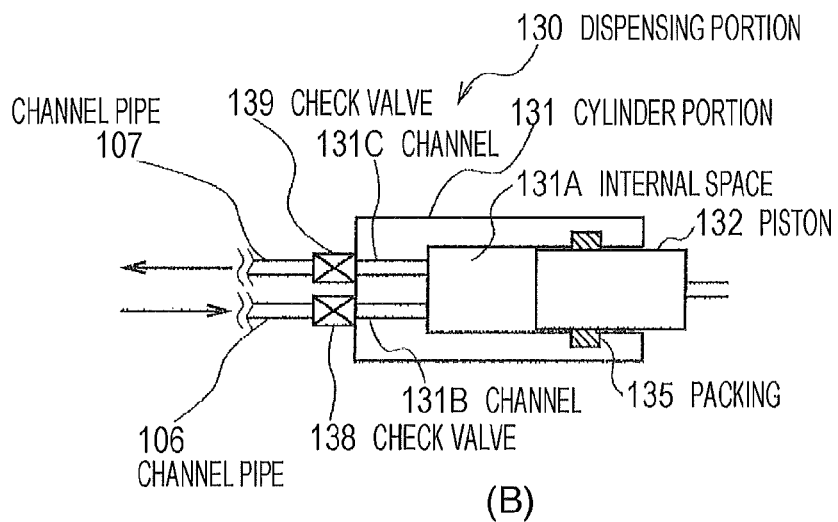
(B)

FIG. 8
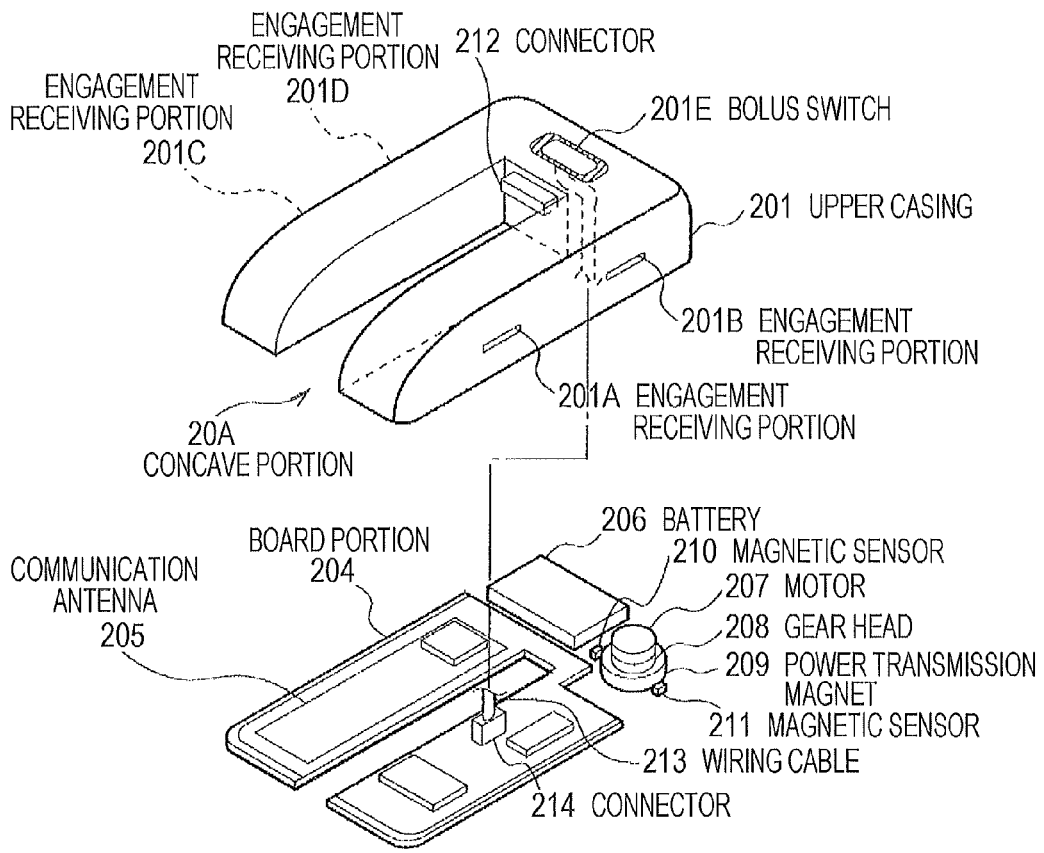
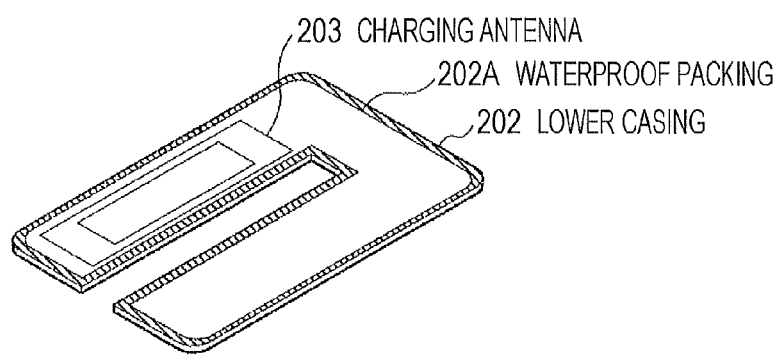

FIG. 10
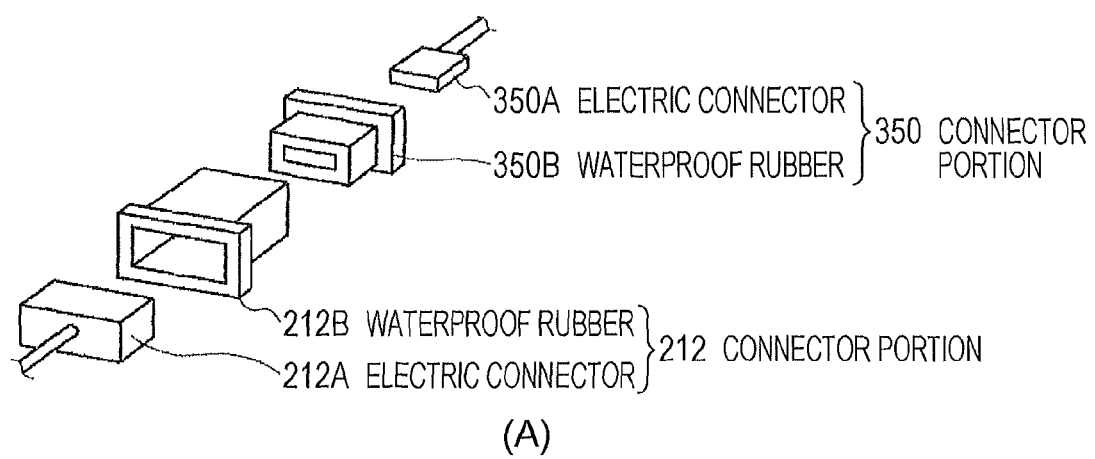
(A)
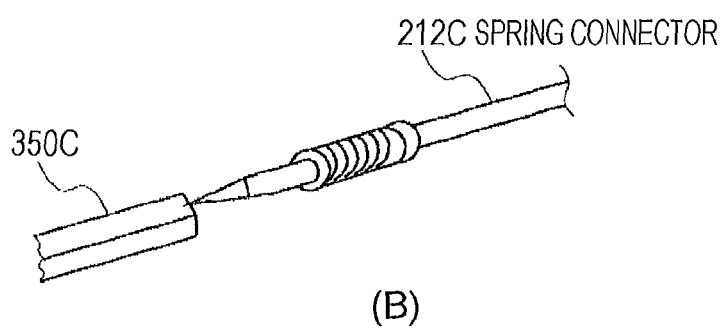
(B)

PUNCTURE DEVICE

CROSS-REFERENCES TO RELATED APPLICATIONS

This application is a continuation of International Application No. PCT/JP2012/075276 filed on Sep. 24, 2012, and claims priority to Japanese Application No. 2011-209978 filed on Sep. 26, 2011 and Japanese Application No. 2011-209980 filed on Sep. 26, 2011, the entire content of all three of which is incorporated herein by reference.

TECHNICAL FIELD

The present invention generally relates to a liquid-medicine administration device, a puncture device, a liquid-medicine filling device, a liquid-medicine filling method, and liquid-medicine filling system suitably applied to a case where, for example, insulin is injected into a human body.

BACKGROUND DISCUSSION

In recent years, the number of the worldwide diabetes patients tends to increase including Japan. Accordingly, there is concern that medical expense may seriously increase. Considering diabetes types, type-1 diabetes is a chronic disease, and for a type-1 diabetes patient is necessary to inject a suitable amount of insulin at a prescribed time. In the past, insulin was dispensed manually using a syringe or an injector. In this regard, an automatic liquid-medicine administration system has been developed, by which a dose and a dispense time can be programmed in order to more conveniently and safely perform appropriate treatment.

Such a system has an infusion pump, a dedicated infusion set, and a catheter. Currently, a system having a portable liquid-medicine administration device is also employed. Recently, as such a portable system, in order to remove cumbersomeness in tubing of the infusion set and improve operability, a patch type liquid-medicine administration device has been developed, in which a liquid medicine is administered by directly inserting a catheter and performing administration from a small-sized and light-weight infusion pump attached to a body surface using a double-sided tape without using the infusion set. An example is disclosed in Japanese Application Publication No. 2010-501283.

SUMMARY

According to one aspect, a portable liquid-medicine administration device configured to be held on a living body comprises: a first casing; a liquid-medicine storage portion in the first casing to store liquid medicine; a dispensing portion in the first casing that externally dispenses the liquid medicine stored in the liquid-medicine storage portion; a first power transmission mechanism in the first casing that transmits power to the dispensing portion to operate the dispensing portion to dispense the liquid medicine stored in the liquid-medicine storage portion; a second casing detachably installed in the first casing; a second power transmission mechanism in the second casing, with the second power transmission mechanism mechanically or electromagnetically interacting with the first power transmission mechanism; a driving portion in the second casing that drives the dispensing portion via the first and second power transmission mechanisms to dispense the liquid medicine from the dispensing portion; and a detection portion in the second casing which detects that the dispensing portion is driven by the driving portion.

In this configuration, even when the dispensing portion and the driving portion are provided in different casings in the portable liquid-medicine administration device held by a living body, it is possible to detect driving of the dispensing portion in a contactless manner using the detection portion provided in the second casing where the driving portion is provided. Therefore, it is possible to monitor whether or not a liquid medicine is suitably administered and feedback driving information of the dispensing portion to control of the driving portion. Accordingly, it is possible to perform stable control.

According to another aspect, a liquid-medicine administration device configured to be attached to a body surface of a user's living body comprises: a casing possessing a surface configured to be attached to the body surface of the user's living body; a liquid-medicine storage portion configured to store liquid medicine; a puncture portion in communication with the liquid-medicine storage portion and forming a flow channel positionable in the user's living body and through which the liquid medicine flows from the liquid-medicine storage portion into the user's living body after a tip of the puncture portion moved to a position projecting beyond the surface of the casing punctures the user's living body by a puncture mechanism and a puncture release mechanism when a controller orders with the wireless that inject a tip of the hollow needle and a tip of the sheath into the user's living body after the surface of the casing is attached to the body surface of the user's living body, and the hollow needle is only retracted with a caulking releasing by a puncture release mechanism and with an elastic portion, and the tip of the sheath is indwelling in the user's living body; and an angle adjustment portion that adjusts a protruding angle of the tip portion of the puncture portion relative to the surface of the casing to adjust an angle at which the tip portion enters the user's living body.

This liquid-medicine administration device makes it possible to adjust the angle of the puncture portion against a surface arranged to adjoin a living body. Therefore, even when a movement distance of the puncture portion is fixed, it is possible to perform the puncture, and the sheath indwelling, up to any depth inside the living body just by adjusting the angle.

It is thus possible to administer medicine into an infusion layer of subcutaneous tissues depending on physiques according to a medicine design and improve medication safety and user-friendliness.

According to still another aspect disclosed here, a puncture device includes a hollow needle possessing both a tip portion configured to puncture a living body and an elastic portion; a fixing portion fixed to a part of the hollow needle so that the part of the hollow needle is a fixed part of the hollow needle, with the fixed part of the hollow needle being positioned on a side of the elastic portion opposite the tip portion so that the elastic portion is located axially between the tip portion and the fixed part; a sheath portion covering a part of or entirety of the hollow needle from the elongating portion to the tip portion, where the elongating portion is a plastically deformable elongating member, with one end of the sheath portion located closer to the elongating portion that being fixed to the elongating portion without any gap between an outer periphery of the sheath portion and an inner periphery of the elongating portion; and located closer to the elongation portion that being fixed to the hollow needle without any gap between outer periphery of the hollow needle and an inner periphery of the elongating portion. The holding portion (caulking) is positioned between the tip portion of the hollow needle and the plastically deformable elongating member. A caulking release mechanism releases the caulking of the holding portion between the hollow needle and the sheath portion after the tip portion of the hollow needle and the sheath portion are punctured into a living body by moving the caulking in a direction causing a spring of the puncture mechanism and the elastic portion to extend when the caulking hits a movement restricting portion. The caulking released by the puncture mechanism (pressure portion), when the holding of the hollow needle using the caulking is released, and the elastic portion contracts and because bonded the hollow needle and caulking, the hollow needle was only retracted. The elongating portion elongates and is held in an elongated condition. The tip portion of the sheath is indwelt a living body.

According to a further aspect, a liquid-medicine administration device configured to be attached to a body surface of a user's living body includes a liquid-medicine storage portion configured to store liquid medicine, a hollow needle in communication with the liquid-medicine storage portion and forming a flow channel through which the liquid medicine stored in the liquid-medicine storage portion flows, the hollow needle including both a tip portion configured to puncture the user's living body and an elastic portion, a fixing portion fixed to a part of the hollow needle so that the part of the hollow needle is a fixed part of the hollow needle, with the fixed part of the hollow needle being positioned on a side of the elastic portion opposite the tip portion so that the elastic portion is located axially between the tip portion and the fixed part; and a sheath portion covering a part of or entirety of the hollow needle from the elongating portion to the tip portion. The sheath portion is bonded a plastically deformable elongating member, with one end of the sheath portion located closer to the elongating portion being fixed to the elongating portion without any gap between the outer periphery of the sheath and the inner periphery of the elongating portion. A caulking holds the hollow needle and the sheath portion in an caulking manner, and the caulking is positioned between the tip portion of the hollow needle and the plastically deformable elongating member. A caulking-release mechanism releases caulking portion between the hollow needle and the sheath portion after the tip portion of the hollow needle and the sheath portion are punctured into a living body by moving the caulking by the puncture mechanism in a direction causing the elastic portion to extend. The hollow needle is only retracted by the elastic portion. The elongating portion elongates and is held in an elongated condition when the elastic portion contracts and the hollow needle is retracted.

With this configuration, since one end of the sheath portion is fixed to the hollow needle without a gap via the elongating portion, the leading end of the hollow needle and the sheath portion is inserted into a living body by puncturing the living body with the reading of the hollow needle, and the hollow needle only returns to its original position by releasing holding a pressure of the caulking. However, since the elongating portion maintains the elongated shape, it is possible to continuously maintain only the sheath in the insertion state into the living body. Therefore, it is possible to improve user-friendliness without leaking of the liquid medicine.

According to another aspect, a liquid-medicine filling device that fills liquid medicine into a liquid-medicine administration device which administers the liquid medicine into a user's living body comprises a liquid-medicine container including a device connecting portion possessing one end configured to be connected to the liquid-medicine administration device, and first and second side face connecting portions provided with first and second holes allowing an internal space in the liquid-medicine container to communicate exteriorly of the liquid-medicine container at a predetermined height of a side face of the liquid-medicine container, and wherein the liquid-medicine container includes a piston possessing one end facing the device connecting portion and an opposite end connected to a plunger to form a plunger-linked piston that is slidably movable within the internal space. The liquid-medicine filling device also includes a pump communicating with the first side face connecting portion to draw-in liquid medicine from a liquid medicine storage communicating with the second side face connecting portion, a plunger driving mechanism that drives the piston to slidably move the plunger-linked piston in the internal space, and a pump driving portion that drives the pump. An absorption detection portion detects a predetermined amount of the liquid medicine that flows to the liquid-medicine container as the pump is driven, and a plunger driving portion operates the plunger driving mechanism to drive the piston toward the device connecting portion while communication between the pump and the first side face connecting portion and communication between the liquid medicine storage and the second side face connecting portion are closed, in order to inject the liquid medicine flowing to the liquid-medicine container into the liquid-medicine administration device.

According to a further aspect, a method for filling a liquid-medicine administration device with liquid medicine to administer the liquid medicine into a user's body involves introducing the liquid medicine into a liquid-medicine container by driving a pump that communicates with an internal space of the liquid-medicine container by way of a first side face connecting portion of the liquid-medicine container, wherein the driving of the pump draws into (sucks into) the internal space the liquid medicine from a liquid medicine storage communicating with a second side face connecting portion of the liquid-medicine container. The liquid-medicine container also includes a connecting portion possessing one end connected to the liquid-medicine administration device, with the first side face connecting portion including a first hole and the second side face connecting portion including a second hole, and the first and second holes communicating the internal space and an outer side with each other at a predetermined height position. The method also includes detecting that a predetermined amount of the liquid medicine flows into the liquid-medicine container; and injecting at least some of the liquid medicine which is in the liquid-medicine container into the liquid-medicine administration device by slidably moving a piston, which is positioned in the internal space at a position spaced from the connecting portion, toward the connecting portion which is connected to the liquid-medicine administration device while communication between the pump and the first side face connecting portion and communication between the liquid medicine storage and the second side face connecting portion is closed.

After the liquid medicine is extracted from the liquid medicine storage to the outer casing of the cylinder using the pump, the liquid medicine is injected into the liquid-medicine administration device by moving the plunger. Therefore, a user is not urged to perform a cumbersome manipulation, and it is possible to improve user-friendliness.

According to a still further aspect, a liquid-medicine administration system includes a portable liquid-medicine administration device that administers liquid medicine into a living body, a liquid-medicine filling device that introduces the liquid medicine into the liquid-medicine administration device, and a notification unit providing notification of a remaining liquid medicine amount in the liquid-medicine administration device, wherein the liquid-medicine filling device comprises: an injection portion that injects the liquid medicine into the liquid-medicine administration device, and an injection amount detection portion that detects an amount of the liquid medicine injected into the liquid-medicine administration device. The liquid-medicine administration device comprises a liquid-medicine storage portion that stores the liquid medicine, a dispensing portion that dispenses the liquid medicine stored in the liquid-medicine storage portion to the living body, and a dispense amount detection portion that detects a liquid medicine amount dispensed by the dispensing portion. The notification unit provides notification of the remaining liquid medicine amount in the liquid-medicine administration device obtained by subtracting the liquid medicine amount detected by the dispense amount detection portion from the liquid medicine amount detected by the injection amount detection portion as a remaining liquid-medicine amount of the liquid-medicine filling device.

According to another aspect of the disclosure here, a portable liquid-medicine administration device for administering liquid medicine into a living body includes a liquid-medicine storage portion containing liquid medicine received from a liquid-medicine filling device, a receiver portion that obtains a liquid-medicine filling amount from the liquid-medicine filling device, a dispensing portion that dispenses the liquid medicine stored in the liquid-medicine storage portion into the living body, a dispense amount detection portion that detects a liquid medicine amount dispensed by the dispensing portion, and a notification portion that provides notification of a value, obtained by subtracting a liquid medicine amount detected by the dispense amount detection portion from an amount of the liquid medicine in the liquid-medicine storage portion received from the liquid-medicine filling device, as a remaining liquid-medicine amount in the liquid-medicine filling device.

By virtue of this arrangement, the remaining liquid-medicine amount of the liquid-medicine storage portion can be notified to a user when the liquid medicine is administered to a living body. Therefore, it is possible to improve user-friendliness.

According to a further aspect, a portable liquid-medicine administration device comprises a first casing, a liquid-medicine storage portion in the first casing to store liquid medicine, a dispensing portion in the first casing to dispense the liquid medicine from the liquid-medicine storage portion, a second casing detachably installed in the first casing, and a puncture and sheath indwelling portion in the second casing and possessing one end communicating with the dispensing portion and an other end protruding from a surface of the second casing facing the living body while the first and second casings are connected so as to puncture and to indwell the sheath in the living body.

With this configuration of the portable liquid-medicine administration device, the puncture (and sheath indwelling) portion is detachably installed in the liquid-medicine storage portion that stores the liquid medicine and the dispensing portion that dispenses the liquid medicine. Therefore, it is possible to exchange only the puncture portion.

The liquid-medicine administration device, puncture (and sheath indwelling) device, liquid-medicine filling device, liquid-medicine filling method, and liquid-medicine filling system disclosed here are user-friendly.

BRIEF DESCRIPTION OF DRAWINGS

FIGS. 4(A) and 4(B) are schematic diagrams illustrating a liquid medicine storage/dispensing unit before and after storage.

FIGS. 7(A) and 7(B) are schematic diagrams illustrating a configuration of a dispensing portion.

FIG. 8 is an exploded perspective diagram illustrating a driving control unit.

FIGS. 10(A) and 10(B) are schematic diagrams illustrating a connector.

DETAILED DESCRIPTION

Hereinafter, an embodiment of the liquid-medicine administration device, a puncture (and sheath indwelling) device, a liquid-medicine filling device, a liquid-medicine filling method, and liquid-medicine filling system will be described in detail with reference to the accompanying drawings.

1. Configuration of Liquid-Medicine Administration System

Figure 1:
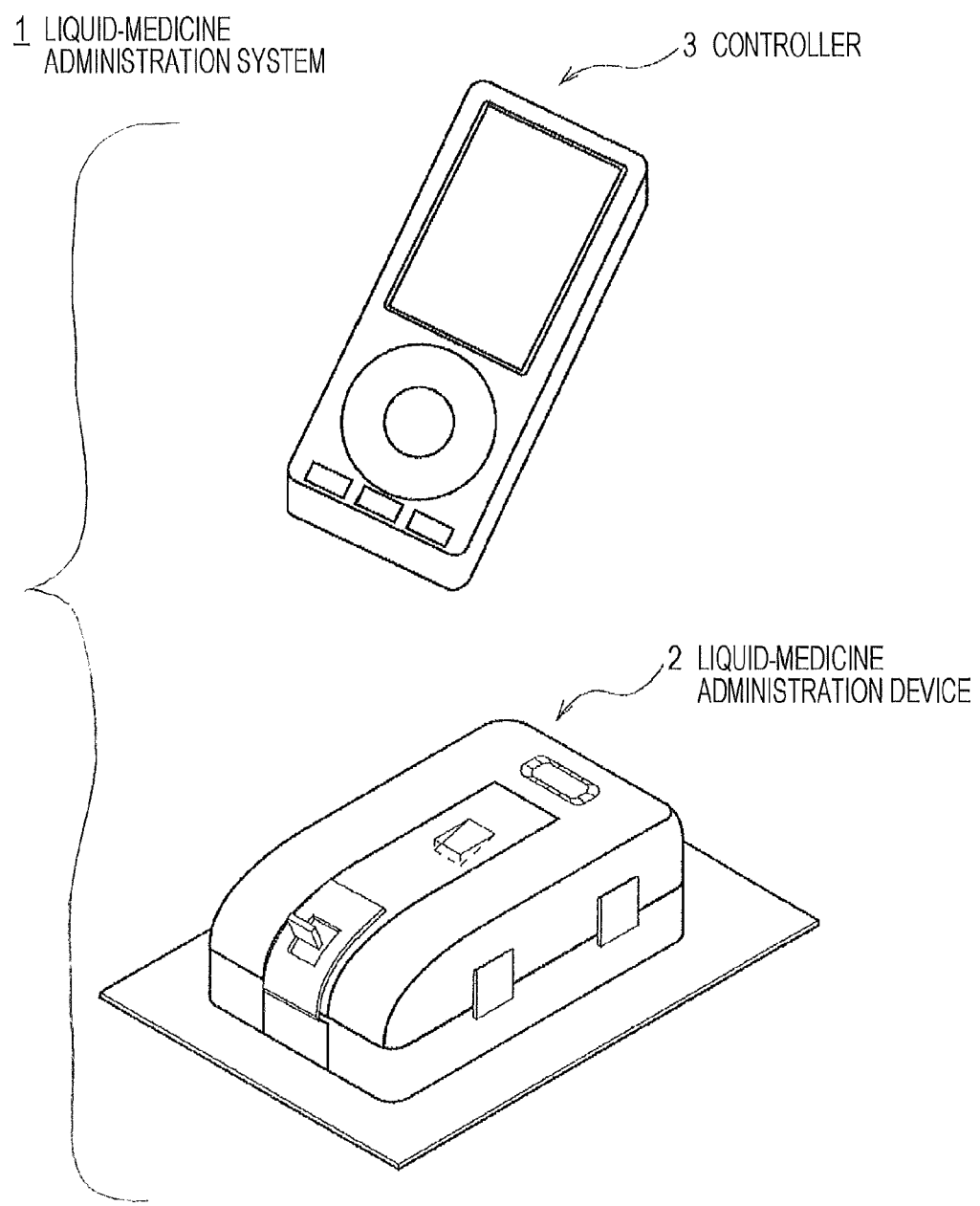
FIG. 1 is a schematic diagram illustrating a configuration of a liquid-medicine administration system.

Referring to FIG. 1, a liquid-medicine administration system 1 includes: a portable liquid-medicine administration device 2 configured to be attached to a user's skin for holding and use; a controller 3 that transmits a signal responding to a user's hollow needle and sheath insert and liquid medicine input instruction to the liquid-medicine administration device 2 via radio communication; a battery charger 4 (FIG. 18) that electrically charges a battery 206 (FIG. 8) provided in the liquid-medicine administration device 2; and a liquid-medicine filling device 5 (FIG. 19) that fills a liquid medicine in a liquid medicine bag 110 (FIG. 3) of the liquid-medicine administration device 2 through injection.

2. Configuration of Liquid-Medicine Administration Device

Figure 2:
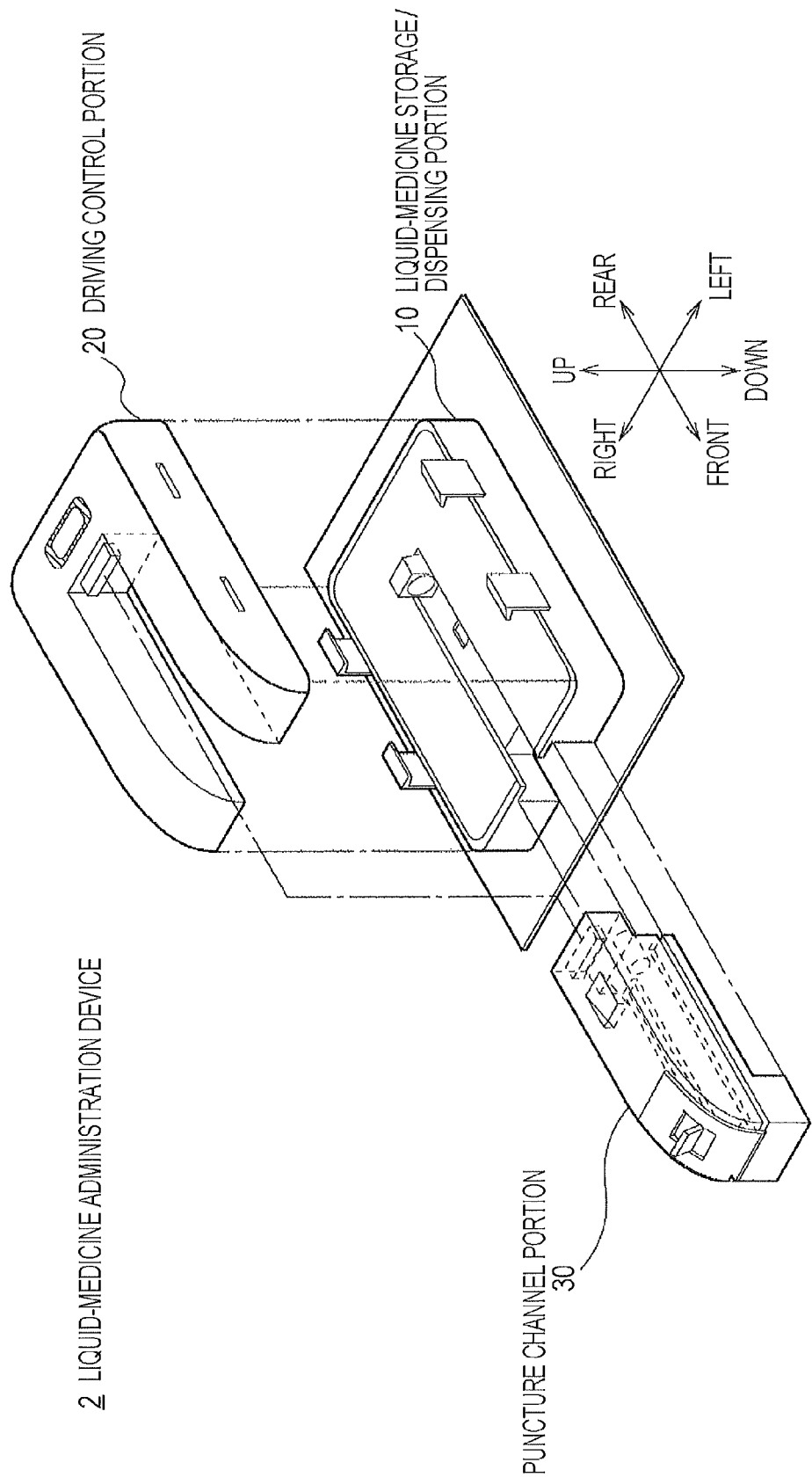
FIG. 2 is a schematic diagram illustrating a configuration of a liquid-medicine administration device.

The liquid-medicine administration device 2 internally stores a liquid medicine (such as insulin) and administers a liquid medicine into a user's body and insert the hollow needle and the sheath into a user's body in response to a control signal transmitted from a controller 3. Referring to FIG. 2, the liquid-medicine administration device 2 includes a detachably installed liquid medicine storage/dispensing unit 10, a driving control unit 20, and a puncture (and sheath indwelling) channel unit 30.

In the liquid-medicine administration device 2, the liquid medicine storage/dispensing unit 10 and the driving control unit 20 are engaged with each other in a vertical direction. Then, the puncture channel unit 30 is slidingly fitted and integrated to the liquid medicine storage/dispensing unit 10 and the driving control unit 20 from the front direction. The liquid-medicine administration device 2 is attached to a user's skin and used in this state.

The liquid-medicine administration device 2 preferably has a small enough size to be attached to a user's skin. For example, the liquid-medicine administration device 2 may have a substantially rectangular shape with a length of 43 mm, a width of 34 mm, and a height of 12 mm.

2-1. Configuration of Liquid Medicine Storage/Dispensing Unit

Figure 3:
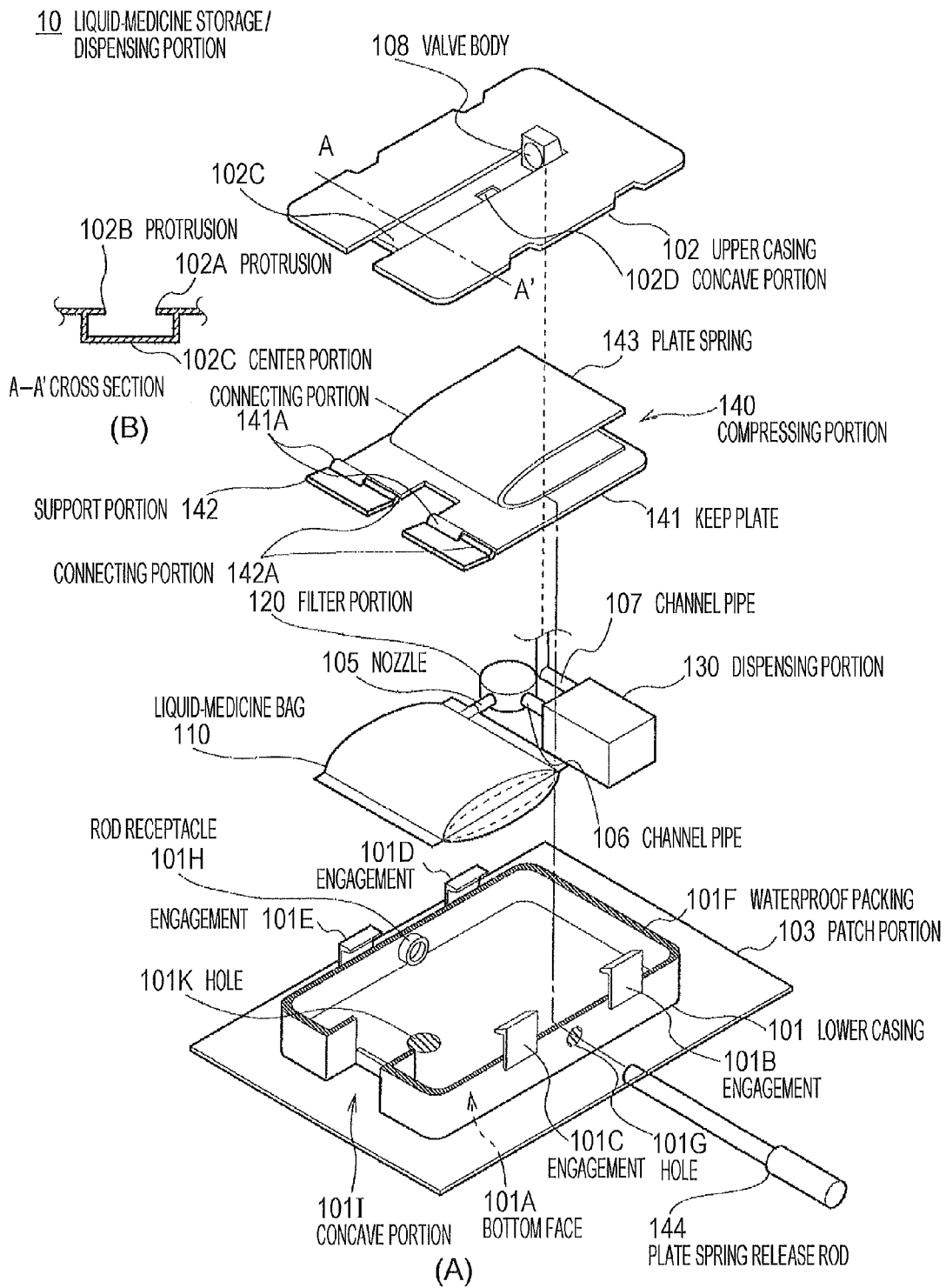
FIG. 3 is an exploded perspective view of a liquid medicine storage/dispensing unit.

Referring to FIGS. 3, 4(A), and 4(B), the liquid medicine storage/dispensing unit 10 is formed in a substantially flat rectangular shape including a lower casing 101 provided with an internal space with an opened top and an upper casing 102 closing the opening of the lower casing 101 and secured to the lower casing, for example by screws.

The liquid medicine storage/dispensing unit 10 is provided with a liquid medicine bag 110, a filter portion 120, a dispensing portion 130, and a compressing portion 140 in a space formed by the lower and upper casings 101 and 102.

The lower casing 101 is provided with a patch portion 103 made of a double-sided adhesive tape or a line of adhesive on a bottom face 101A of the lower casing 101. The liquid-medicine administration device 2 is held by a user by attaching the patch portion 103 onto a user's skin. In addition, the bottom face 101A of the lower casing 101 is formed of a transparent member so that the amount of the liquid medicine stored in the liquid medicine bag 110 is exposed to the outside. As a result, it is possible to recognize or visually observe the remaining amount of liquid medicine even after the liquid-medicine administration device 2 is attached to a user's skin.

On a side face along a longitudinal direction (hereinafter, also referred to as an anteroposterior direction) of the lower casing 101, engagement portions 101B to 101E are provided as protrusions to extend along an arrangement direction of the driving control unit 20. The engagement portions 101B to 101E are engaged with engagement receiving portions 201A to 201D (FIG. 8) described below so that the liquid medicine storage/dispensing unit 10 and the driving control unit 20 abut each other.

The lower casing 101 is provided with a waterproof packing 101F on a surface where the upper casing 102 abuts. Since the lower casing 101 is assembled with the upper casing 102 by interposing the waterproof packing 101F using a screw or by ultrasonic welding, it is possible to prevent intrusion of a liquid into an internal space from a gap between the lower casing 101 and the upper casing 102.

On a side face along the longitudinal direction of the lower casing 101, there are provided a hole 101G where a plate spring release rod 144 is inserted and a rod receptacle 101H that receives a leading end of the plate spring release rod 144 penetrating the hole 101G. A duckbill valve packing is inserted into the hole 101G so that the opening is closed when the plate spring release rod 144 is removed. In addition, a hole 101K where an injection portion 104 is fitted is provided on the bottom face 101a of the casing 101 in order to inject a liquid medicine into the liquid medicine bag 110.

Around the hole 101K of the bottom face 101A of the lower casing 101, an engagement receiving portion 101L is provided as a concave shape portion engaged with an engagement portion 523A of an injection needle portion 523 of the liquid-medicine filling device 5 described below in detail. Around the hole 101K, a waterproof function is implemented by tightly combining the lower casing 101 with au injection portion 104 which is an elastic member meltingly bonded to the liquid medicine bag 110.

In addition, in a front side of the lower casing 101, a concave portion 101I which is a space where a part of the puncture channel unit 30 is tightly inserted is provided when the liquid medicine storage/dispensing unit 10 is engaged with the puncture channel unit 30.

The upper casing 102 is provided with protrusions 102A and 102E protruding to face each other along a longitudinal direction in order to guide the puncture channel unit 30 to slide from the front side for engagement with the liquid medicine storage/dispensing unit 10. In addition, the upper casing 102 has a center portion 102C interposed between the protrusions 102A and 102B to form the protrusions 102A and 102B and formed to be lower than other portions. That is, the center portion 102C is recessed relative to the portions of the upper casing 102 adjoining (surrounding) the center portion 102C.

In a predetermined position of the center portion 102C, the upper casing 102 is provided with a concave portion 102D where a convex portion 301C (FIG. 12) of the puncture channel unit 30 is tightly inserted when the liquid medicine storage/dispensing unit 10 is engaged with the puncture channel unit 30.

Figure 5:
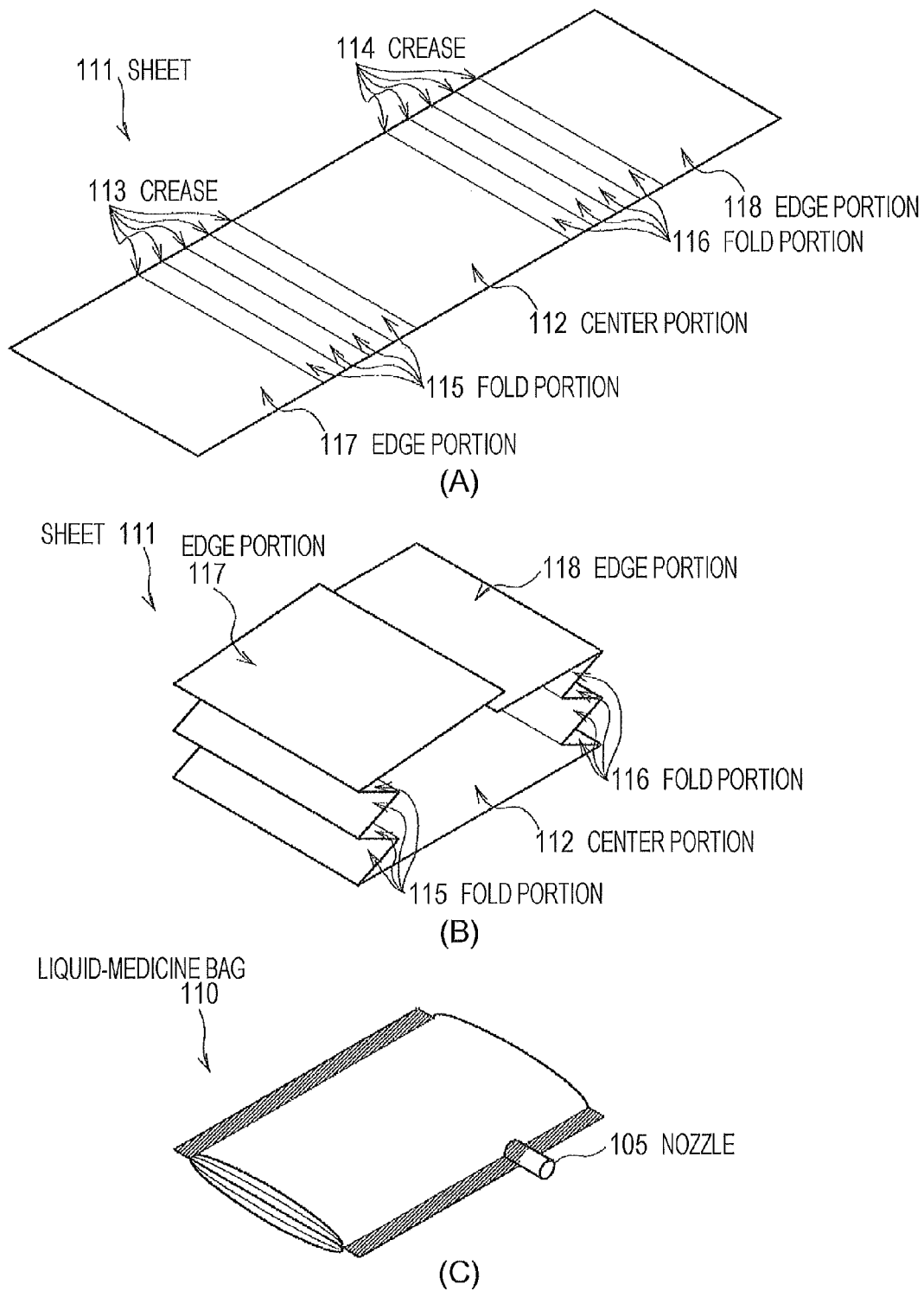
FIGS. 5(A) to 5(C) are schematic diagrams illustrating a process of forming a liquid medicine bag.

Referring to FIGS. 5(A) to 5C, the liquid medicine bag 110 as a liquid-medicine storage portion is formed from a rectangular sheet 111 made of, for example, polyurethane, vinyl chloride, or polyethylene. Referring to FIG. 5(A), the sheet 111 is provided with at least three or more odd-numbered creases 113 and 114 (five creases in this embodiment) formed with the same interval in both sides of a portion (hereinafter, also referred to as a center portion) 112 corresponding to a bottom face of the liquid medicine bag 110 made of a flexible thermoplastic resin, which is a center portion of the longitudinal direction. As a result, the sheet 111 has an even-numbered portions 115 and 116 (hereinafter, also referred to as a fold portion) having a predetermined width between the neighboring creases 113 and 114.

In addition, in the sheet 111, portions 117 and 118 (hereinafter, also referred to as an edge portion) longer than a half of the length of the center portion 112 in the longitudinal direction are provided closer to the end than the outermost creases 113 and 114 in the longitudinal direction.

In this sheet 111, the creases 113 and 114 are alternately folded with a peak and a valley such that the fold portions 115 and 116 overlaps with the center portion 112. As illustrated in FIG. 5(B), the edge sides of the edge portions 117 and 118 partially overlap each other.

In the sheet 111, the overlapping portions of the edge portions 117 and 118 are meltingly bonded, and the widthwise peripheries are meltingly bonded. When the widthwise peripheries of the sheet 111 are meltingly bonded, a nozzle 105 for causing a space enveloped by the sheet 111 and an external space to communicate with each other is nipped into one of the peripheries. That is, the nozzle 105 communicates with and opens into the interior of the bag 110 to allow communication of the bag interior, and the nozzle 105 is fixed in place along a portion of the bag.

In addition, in a predetermined position of the center portion 112 of the sheet 111, an injection portion 104 having a check valve formed of, for example, a synthetic rubber is provided in order to inject a liquid medicine into the liquid medicine bag 110 from the outside. In this manner, the liquid medicine bag 110 illustrated in FIG. 5(C) is formed.

Before the liquid medicine is introduced into the liquid medicine bag, the liquid medicine bag 110 formed in this manner is folded such that neighboring fold portions 115 and 116 adjoin each other, and the center portion 112 and the edge portions 117 and 118 overlap each other.

Therefore, the liquid medicine bag 110 is squeezed such that the center portion 112 and the edge portions 117 and 118 adjoin each other when the liquid medicine bag 110 dispenses a liquid medicine filled in the inside to the outside through the nozzle 105. Therefore, it is possible to dispense the liquid medicine to the outside without liquid medicine remaining in the inside.

Typically, in a liquid medicine bag of the related art, a pair of films is meltingly bonded to form the periphery, and the liquid medicine is injected into a space formed by a pair of films. However, in this case, a distance between a pair of films is reduced toward the periphery.

Therefore, in the liquid-medicine administration device having the liquid medicine bag of the related art, a useless space is formed in a non-inflating portion of the liquid medicine bag when the liquid medicine is injected in a portion close to the periphery of the liquid medicine bag out of a space where the liquid medicine bag is stored. Therefore, in the liquid medicine bag of the related art, a size of the liquid-medicine administration device disadvantageously increases.

The liquid medicine bag 110 has the fold portions 115 and 116 in the longitudinal direction. Therefore, as the liquid medicine is injected, the fold portions 115 and 116 expand to separate the center portion 112 and the edge portions 117 and 118 (vertically).

As a result, as the fold portions 115 and 116 expand, the liquid medicine bag 110 can vertically expand in the vicinity of the periphery of the liquid medicine bag 110 when the liquid medicine is injected. Therefore, when the liquid medicine is injected into the space formed by the lower casing 101 and the upper casing 102, a useless space is not formed even in the vicinity of the periphery of the liquid medicine bag 110, and a size of the liquid-medicine administration device 2 can be reduced. Therefore, it is possible to improve user-friendliness.

Figure 6:
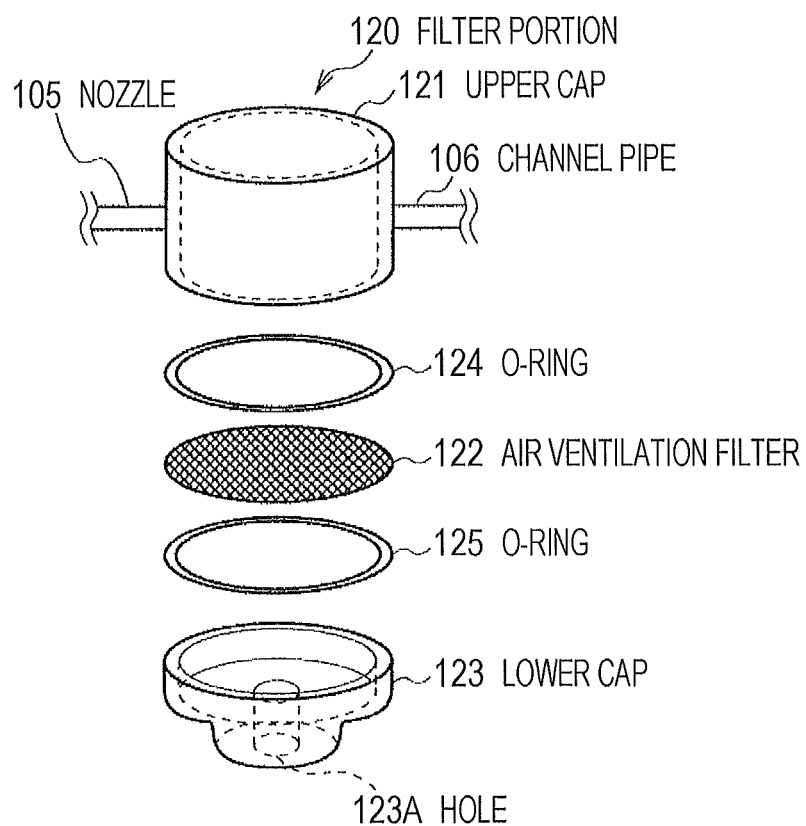
FIG. 6 is a schematic diagram illustrating a filter portion.

Referring to FIG. 6, in the filter portion 120, the nozzle 105 that causes the internal space and the liquid medicine bag 110 to communicate with each other is connected to a side face of an upper cap 121 having an open bottom and an internal space. In addition, the filter portion 120 includes a channel pipe 106 that causes the internal space and the dispensing portion 130 to communicate with each other.

The filter portion 120 is provided with an air ventilation filter 122 that covers an opening (open end) of the upper cap 121 to transmit gas and filter liquid (like an artificial lung membrane) by positive pressure generated by the plate spring. The air ventilation filter 122 is fixed between the upper cap 121 and the lower cap 123 that covers an opening of the upper cap 121 by interposing O-rings 124 and 125 on opposite sides of the filter. The upper cap 121 and the lower cap 123 tightly abut on each other, for example, using ultrasonic welding melting or the like. The lower cap 123 is provided with a vertically penetrating hole 123a.

As a result, the filter portion 120 can discharge only gas (air bubble, etc.) to the outside from the internal space of the upper cap 121 without discharging a liquid medicine through the hole 123A provided in the lower cap 123.

Referring to FIGS. 7(A) and 7(B), the dispensing portion 130 includes a so-called piston pump. A piston 132 is inserted into a cylindrical internal space 131A provided in the cylinder portion 131 from one end side.

The piston 132 is connected to a crank shaft 134 through a crank 133. As the crank shaft 134 rotates, the piston 132 slidingly moves in the internal space 131A of the cylinder portion 131. A packing 135 such as an X-ring or an O-ring is provided on a side face adjoining the internal space 131A of the cylinder portion 131 along a circumferential direction, which is an inner wall of the internal space 131A, in order to prevent a liquid medicine from leaking out of a gap between the piston 132 and the inner wall of the internal space 131A of the cylinder portion 131. The packing 135 is arranged to adjoin the piston 132. In addition, a gasket made of a silicon rubber, a butadiene rubber, or the like may be installed in the piston 132.

The crank shaft 134 is provided with a driving magnet 136 as an example of a first power transmission portion. The driving magnet 136 is provided at one end of the crank shaft 134. A position detection magnet 137 for detecting a position and number of strokes of the piston 132 is provided on or in a side face of the driving magnet 136.

The driving magnet 136 is provided in a position facing a power transmission magnet 209 (FIGS. 8 and 9), which is an example of a second power transmission portion, by interposing the upper casing 102, the driving control unit 20, and the lower casing 202 (FIG. 8). As described below, the driving magnet 136 is attracted to and rotated by the power transmission magnet 209 rotated using a motor 207 and a gear head 208. The motor 207 forms a part of a driving unit that drives the dispensing portion via the first and second power transmission mechanisms to dispense the liquid medicine from the dispensing portion.

In the dispensing portion 130, as the driving magnet 136 is rotated, the crank shaft 134 is rotated so that the piston 132 slidingly moves in the internal space 131A of the cylinder portion 131 through the crank 133.

The cylinder portion 131 is provided oppositely to a side of the internal space 131A, where the piston 132 is inserted, such that the flow channels 131B and 131C communicate with the internal space 131A.

The filter portion 120 is connected to the internal space 131A of the cylinder portion 131 through the channel pipe 106, a check valve 138, and the flow channel 131B. The check valve 138 is provided in the lower casing 101 and when the pressure of the internal space is lower than a check valve 138 opening pressure by slidingly moving the piston 132 to the direction of the open of the cylinder portion (the direction of a bottom dead point), transmits liquid medicine from the filter portion 120 to the internal space 131A, but does not transmit (does not permit transmission of) liquid medicine in the channel pipe 107 and a reverse direction.

A check valve 139 provided in the lower casing 101 is connected to the internal space 131A of the cylinder portion 131 through the flow channel 131C, the check valve 139, and the channel pipe 107. When the pressure of the internal space is higher than a check valve 139 opening pressure by moving slidingly the piston 132 to the reverse direction of the open of the cylinder portion (the direction of a top dead point), the check valve 139 transmits liquid medicine from the internal space 131A to the valve body 108 that is provided in upper casing 102, but does not transmit (does not permit transmission of) liquid medicine in a reverse direction.

While nothing is inserted, the valve body 108 blocks the flow channel. While a nozzle 302 (FIG. 12) provided in the puncture channel unit 30 is inserted, the flow channel is opened to cause the channel pipe 107 and the nozzle 302 to communicate with each other.

Therefore, as the driving magnet 136 and the crank shaft 134 are rotated, and the piston 132 slidingly moves in the internal space 131A of the cylinder portion 131, the dispensing portion 130 dispenses the liquid medicine stored in the liquid medicine bag 110 into a user's body through the flow channel provided in the puncture channel unit 30.

More specifically, the dispensing portion 130 extracts a liquid medicine from the liquid medicine bag 110 when the piston 132 moves from a top dead point to a bottom dead point. The dispensing portion 130 dispenses the liquid medicine that is extracted from the internal space 131A to the channel pipe 107 when the piston 132 moves from the bottom dead point to the top dead point.

The compressing portion 140 includes a keep plate 141, a support portion 142, and a plate spring 143. The keep plate 141 is made of a sheet material having a larger area than that of the center portion 112 of the liquid medicine bag 110 and is provided over the liquid medicine bag 110. The keep plate 141 is supported by a support portion 142 fixed to the lower casing 101 rotatably with respect to the connecting portions 141A and 142A such as a hinge mechanism so as to recede from or approach the liquid medicine bag 110.

The plate spring 143 is a sheet material bent in a substantially V-shape and inserted into a gap between the keep plate 141 and the upper casing 102. The plate spring 143 exerts a force to separate (open) the facing plates formed by bending the sheet material in a substantially V-shape. Therefore, when the plate spring 143 is arranged between the keep plate 141 and the upper casing 102, the keep plate 141 is pressed to the liquid medicine bag 110 side with a constant force at all times.

However, before a liquid medicine is injected into the liquid medicine bag 110 (FIG. 4(A)), a plate spring release rod 144 is inserted from the hole 101G of the lower casing 101 to the compressing portion 140 between the keep plate 141 and the plate spring 143. In this case, in the compressing portion 140, the plate spring 143 does not press the keep plate 141, and the keep plate 141 is freely rotatable.

In the compressing portion 140, as the plate spring release rod 144 is removed after a liquid medicine is injected into the liquid medicine bag 110, the plate spring 143 presses the keep plate 141 toward the liquid medicine bag 110 side. As a result, in the compressing portion 140, the liquid medicine bag 110 is interposed between the keep plate 141 and the lower casing 101 so that a constant positive pressure is applied to the liquid medicine bag 110 (FIG. 4(B)).

As a result, in the compressing portion 140, when air bubbles generated from a dissolved gas exist in the liquid medicine bag 110, the bubbles can be discharged to the outside through the filter portion 120. In addition, a valve open pressure of the check valve 138 connected to the filter portion 120 through the channel pipe 106 is set so as not to open when the piston 132 does not move and is set to open when the piston 132 moves from the bottom dead point to the top dead point. Therefore, liquid medicine does not flow from the liquid medicine bag 110 to the dispensing portion 130 by the positive pressure applied by the compressing portion 140.

In addition, in the compressing portion 140, when the liquid medicine stored in the liquid medicine bag 110 is dispensed by the dispensing portion 130, the liquid medicine bag 110 is pressed to a squeezing direction. Therefore, it is possible to dispense the liquid medicine stored in the liquid medicine bag 110 in an extruding manner without a remaining liquid medicine.

2-2. Configuration of Driving Control Unit

Referring to FIG. 8, a driving control unit 20 is formed in a substantially U-shape having a concave portion 20A matching a shape of the puncture channel unit 30 such that the puncture channel unit 30 is inserted from a front direction.

The driving control unit 20 includes an upper casing 201 having an open bottom and an internal space and a lower casing 202 closing the opening of the upper casing 201 and secured to the upper casing, for example by screws. In a space between the upper and lower casings 201 and 202, a charging antenna 203, a board portion 204, a communication antenna 205, a battery 206, a motor 207, a gear head 208, a power transmission magnet 209, and magnetic sensors 210 and 211 are provided.

On an outer side face along a longitudinal direction of the upper casing 201, engagement receiving portions 201A to 201D are provided as hollows or hollow portions engaged with the engagement portions 101B to 101E, respectively, provided in the liquid medicine storage/dispensing unit 10.

A bolus switch 201E pressed by a user when a certain amount of the liquid medicine is temporarily administered (bolus injection) is provided on a top face of the upper casing 201. This bolus switch 201E may be provided in a position hollowed (recessed) from the top face of the upper casing 201 in order to prevent a user from erroneously or inadvertently pressing it, for example, while turning a user's body (e.g., the user turning over in bed).

The bolus switch 201E is connected to the board portion 204 through a wiring cable 213 and a connector 214.

In the lower casing 202, a waterproof packing 202A is provided on a surface abutting on the upper casing 201, and the upper casing 201 is attached to the lower casing 202 using a screw by interposing the waterproof packing 202A or the ultrasonic welding fusion. Therefore, it is possible to prevent liquid from intruding into an internal space from a gap between the upper casing 201 and the lower casing 202.

The charging antenna 203 is bonded to the top face of the lower casing 202 to receive electricity (electromagnetic wave) supplied from the battery charger 4 (FIG. 18) described below.

On the top face of the lower casing 202, electric circuits such as a central processing unit (CPU), random access memory (RAM), and read-only memory (ROM) and the board portion 204 having the communication antenna 205 for transmitting and receiving a signal between the controller 3 and the liquid-medicine administration device 2, and between the liquid-medicine administration device 2 and the liquid-medicine filling device 5 are provided in overlapping relation to the charging antenna 203.

In addition, the battery 206 charged by electricity supplied from the charging antenna 203 to supply electricity to each portion at the time of driving is provided on the lower casing 202.

Furthermore, the motor 207, the gear head 208, and the power transmission magnet 209 are provided in overlapping relation on the top face of the lower casing 202 in this order from the top to face the driving magnet 136 of the liquid medicine storage/dispensing unit 10.

Moreover, on the top face of the lower casing 202, the magnetic sensors 210 and 211 are provided to face in a circumferential direction, where the position detection magnet 137 arranged in the side face of the driving magnet 136 moves, and are separated in a horizontal direction by interposing the power transmission magnet 209.

Figure 9:
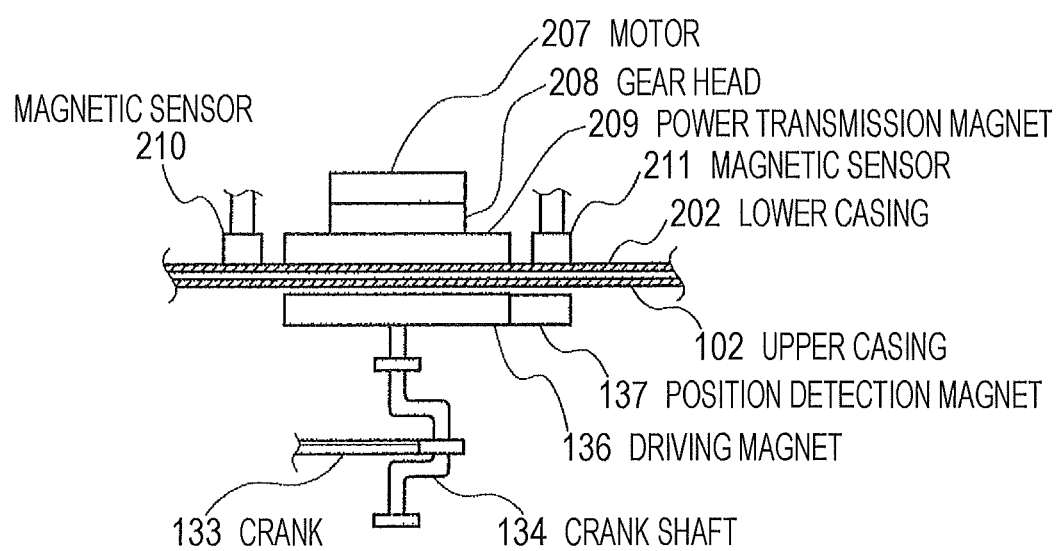
FIG. 9 is a schematic diagram illustrating a power transmission mechanism.

The motor 207 rotates the power transmission magnet 209 at a speed decelerated by the gear head 208. As illustrated in FIG. 9, the power transmission magnet 209 is arranged to face the driving magnet 136 to exert an attracting (magnetic) force with the driving magnet 136 while the liquid medicine storage/dispensing unit 10 and the driving control unit 20 abut each other.

As the motor 207 is rotated through the gear head 208, the driving magnet 136 is rotated in synchronization with the power transmission magnet 209 while the power transmission magnet 209 attracts the driving magnet 136.

Therefore, the motor 207 rotates the crank shaft 134 without contact using the gear head 208, the power transmission magnet 209, and the driving magnet 136 so that the piston 132 connected to the crank 133 slides in the internal space 131A of the cylinder portion 131.

Meanwhile, since the motor 207 causes the piston 132 to slide without contact using a magnetic force between the power transmission magnet 209 and the driving magnet 136, it is necessary to detect whether or not the piston 132 slides or axially moves in synchronization with rotation of the motor 207 (e.g., because rotation of the transmission magnet 209 can't keep pace, and the transmission magnet 209 cannot transmit the driving magnet by high rate duty of the pump). In this regard, the magnetic sensors 210 and 211 for detecting whether or not the piston 132 slides are arranged to face a circumference where the position detection magnet 137 moves.

More specifically, the position detection magnet 137 moves to a position facing the magnetic sensor 210 when the piston 132 is positioned in the top dead point. Therefore, it is detected that the piston 132 is positioned in the top dead point as the magnetic sensor 210 detects a magnetic force of the position detection magnet 137.

The position detection magnet 137 moves to a position facing the magnetic sensor 211 when the piston 132 is positioned in the bottom dead point. Therefore, it is detected that the piston 132 is positioned in the bottom dead point as the magnetic sensor 211 detects a magnetic force of the position detection magnet 137.

In this manner, the magnetic sensors 210 and 211 detect that the piston 132 reciprocates between the top dead point and the bottom dead point. Therefore, it is possible to detect a sliding movement or the number of strokes of the piston 132.

Therefore, as described below in more detail, a microcomputer 220 (FIG. 18) can check whether or not the dispensing portion 130 provided in a space formed by the upper casing 102 and the lower casing 101, where the microcomputer 220 is not provided, is driven the same rotation as the rotation of the power transmission magnet 209 using the magnetic sensors 210 and 211 provided in a space formed by the lower casing 202 by the upper casing 201, where the microcomputer 220 is provided.

On the front face of the concave portion 20A making contact when the puncture channel unit 30 abuts, the upper casing 201 is provided with a connector portion 212 for transmitting and receiving various signals to/from the puncture channel unit 30 by supplying electricity from the battery 206 to the puncture channel unit 30. As illustrated in FIGS. 10(A) and 10(B), the connector portion 212 may be configured such that the waterproof rubber 212B covers the outside of the electric connector 212A in which a plurality of spring connectors 212C for transmitting and receiving electricity and various signals are integrated.

In addition, the connector portion 350 (FIG. 12) of the puncture channel unit 30 connected to the connector portion 212 may also be configured in this manner such that the waterproof rubber 350B covers the outside of an electric connector 350A in which a plurality of connectors 350C for transmitting and receiving electricity and various signals are integrated.

As a result, in the driving control unit 20, it is possible to prevent liquid from invading into the puncture channel unit 30 and the driving control unit 20, and a contact portion between the connectors 350c and spring connectors 212c by making contact with the electric connectors 212A and 350B using the waterproof rubbers (waterproof rubber members) 212B and 350B when the connector portion 212 is connected to the connector portion 350. In addition, when the puncture channel unit 30 is inserted into the liquid medicine storage/dispensing unit 10 using a single pin of the connector, a pin having a length that does not make contact within an insertion allowable limit (in the case of insufficient insertion) is provided, and the puncture channel unit 30 side is connected to a ground electric potential. In addition, in the driving control unit 20 side, it is checked whether or not an electric potential of this pin is a ground electric potential. If the electric potential of the pin is not the ground electric potential, a notification of insufficient insertion of the puncture channel unit 30 is displayed to monitor an insertion state of the puncture channel unit.

2-3. Configuration of Puncture Channel Unit

Figure 11:
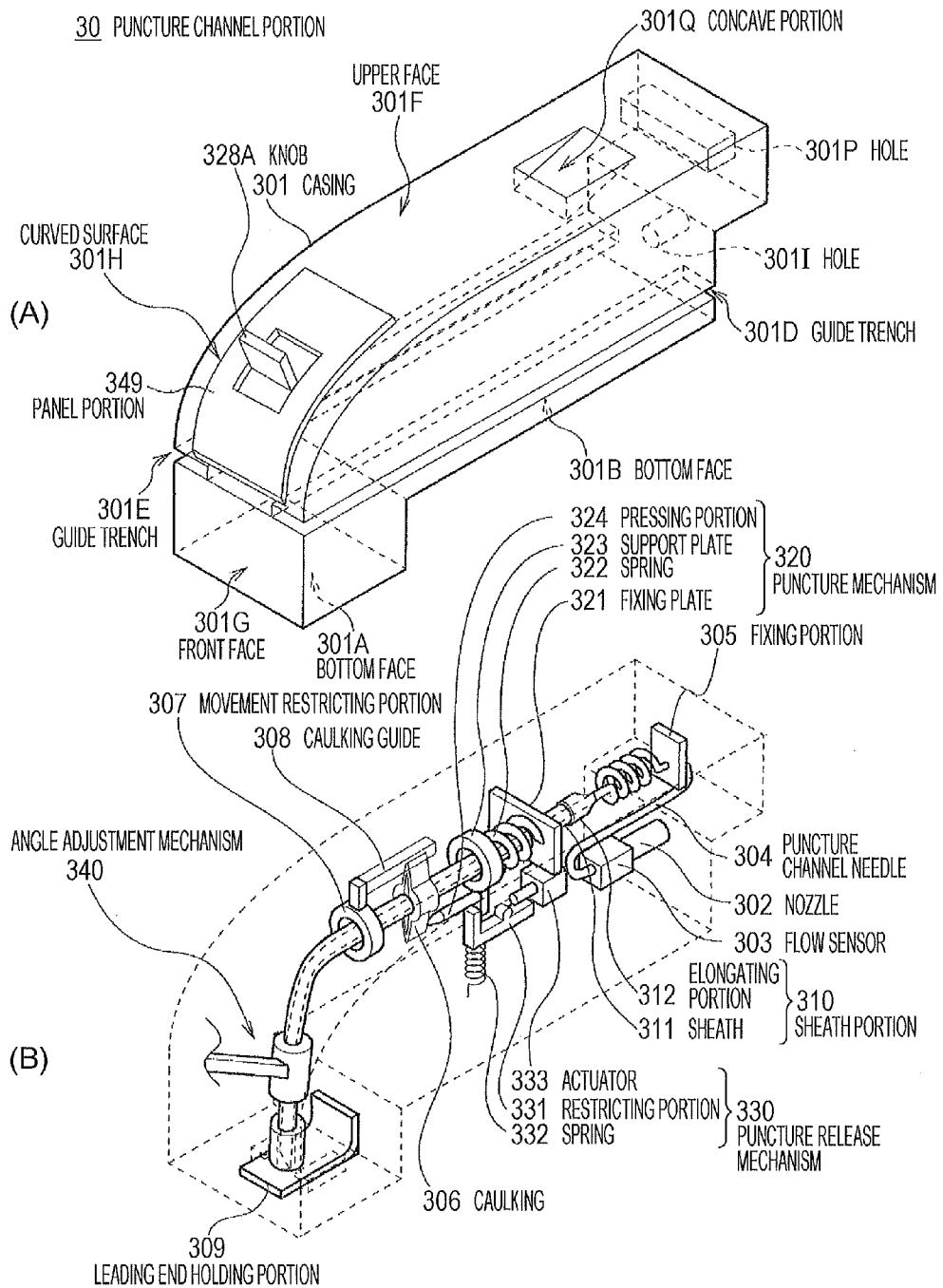
FIG. 11 is a schematic diagram illustrating a puncture (and sheath indwelling) channel unit.
Figure 12:
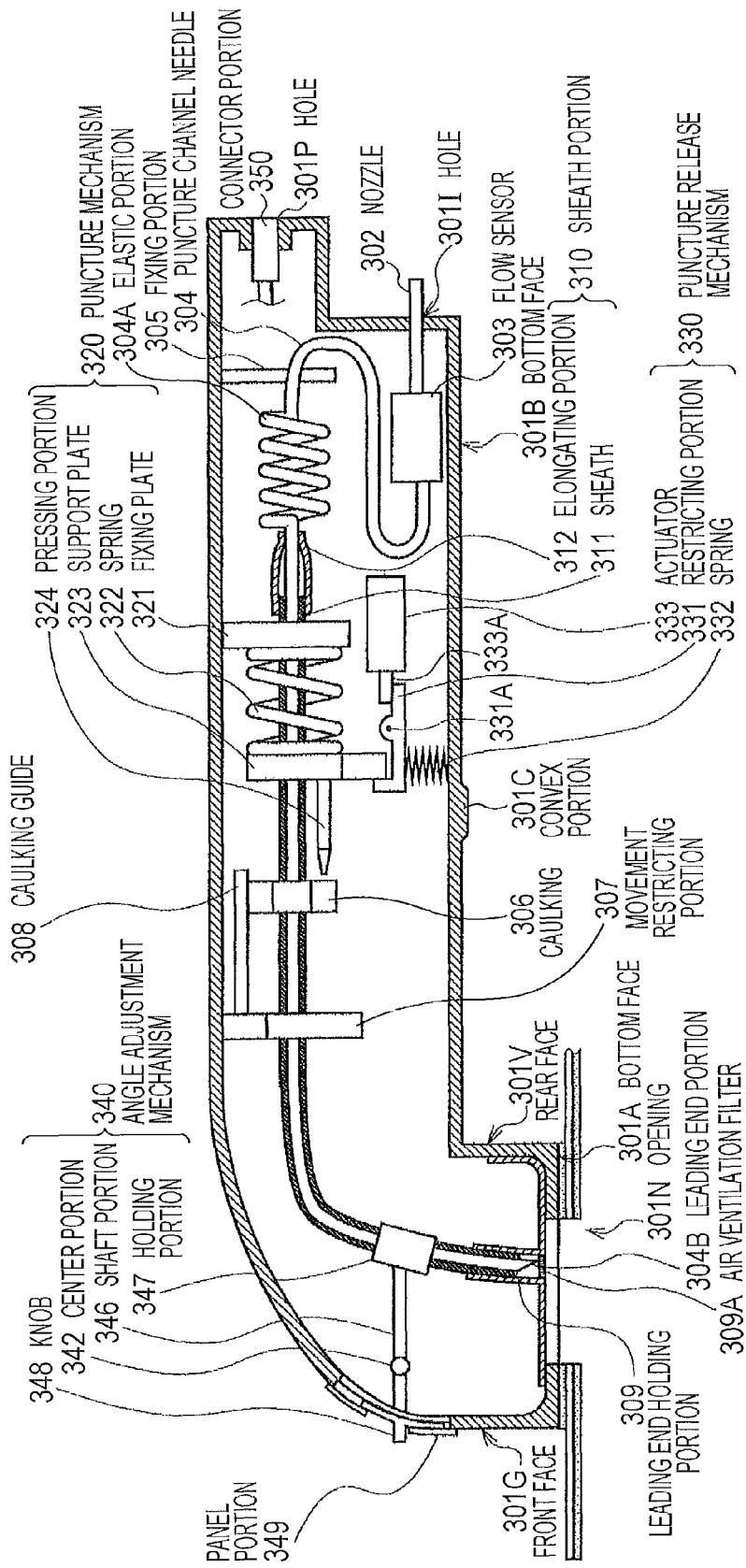
FIG. 12 is a schematic diagram illustrating a configuration of the puncture (and sheath indwelling) channel unit.

Referring to FIGS. 11 and 12, the puncture channel unit 30 has a long and narrow shape along a longitudinal direction, fitted to a space of the concave portions 101I and 20A formed by engaging the liquid medicine storage/dispensing unit 10 with the driving control unit 20. In the puncture channel unit 30, each portion is provided in the internal space of the casing 301 that forms an exterior of the puncture channel unit 30. In addition, FIG. 11(A) illustrates the exterior configuration of the puncture channel unit 30, and FIG. 11(B) illustrates the interior configuration of the puncture channel unit 30. In FIG.

12, for convenient description purposes, a part of the configuration is illustrated in a cross section.

The casing 301 includes bottom faces 301A and 301B. The bottom face 301A is positioned coplanar with the bottom face 101A of the lower casing 101 when the puncture channel unit 30 is fitted to the liquid medicine storage/dispensing unit 10. The bottom face 301B is positioned at a height adjacently facing the center portion 102C of the upper casing 102.

In the casing 301, the convex portion 301C inserted into the concave portion 102D of the upper casing 102 when the puncture channel unit 30 is fitted to the liquid medicine storage/dispensing unit 10 is provided in a position facing the concave portion 102D on the bottom face 301B.

In addition, in the casing 301, guide trenches 301D and 301E engaged with the protrusions 102A and 102B, respectively, of the upper casing 102 of the liquid medicine storage/dispensing unit 10 are formed in opposite side faces along a longitudinal direction.

The casing 301 is provided with a concave portion 301Q on a top face 301F for hooking a user's finger in order to remove the puncture channel unit 30 from the liquid medicine storage/dispensing unit 10 and the driving control unit 20.

In addition, the casing 301 is curved from the top face 301F to the front face 301G and is provided with an angle adjustment mechanism 340, described below in detail, in a curved surface 301H.

Furthermore, the casing 301 is provided with a hole 301I in a position facing the valve body 108 of the liquid medicine storage/dispensing unit 10. When the puncture channel unit 30 is fitted to the liquid medicine storage/dispensing unit 10, the nozzle 302 inserted into the valve body 108 penetrates the hole 301I and is fixed. The nozzle 302 is fixed without a gap in the hole 301I.

One end of the nozzle 302 is inserted into the valve body 108 and communicates with the channel pipe 107 while the puncture channel unit 30 is fitted to the liquid medicine storage/dispensing unit 10. The other end of the nozzle 302 is connected to a flow sensor 303.

The flow sensor 303 detects whether or not the passing liquid medicine flows. For example, the flow sensor may include a flow sensor capable of detecting a temperature change of a thermistor caused by a continuous flow of the liquid medicine by heating the thermistor with a constant electric current, a flow sensor having a single thermistor used as both a heating source and a temperature sensor, a flow sensor having a combination of separate elements for the heating source and the temperature sensor, in which a resistor, a heater wire, a semiconductor, or the like is employed as a heating source, and a thermopile, a platinum resistor, and a semiconductor, or the like is employed as a temperature sensor.

A puncture channel needle 304 is connected to an end of the flow sensor 303 opposite to the other end where the nozzle 302 is connected, so that the nozzle 302 communicates with the puncture channel needle 304. The puncture channel needle 304 is bent in an S-shape from one end side connected to the flow sensor 303, extends along a longitudinal direction therefrom, and is curved to reach the bottom face 301A in the other end side of the casing. The puncture channel needle 304 is made of a metal material. For example, a 28-gauge hollow pipe that can be rather easily bent may be employed.

The puncture channel needle 304 is fixed by the fixing portion 305 projecting to the inside from the casing 301 in a position immediately after being bent in an S-shape.

A part 304A (hereinafter, also referred to as an elastic portion) of the puncture channel needle 304 to the front side from the fixing portion 305 is wound in a helical shape. The elastic portion 304A is expandable and retractable in a longitudinal direction.

A leading end portion 304B (hereinafter, also referred to as a leading end portion) of the other end side of the puncture channel needle 304 is bent to reach the bottom face 301A and has a sharp point.

The puncture channel needle 304 having such a shape dispenses the liquid medicine flowing from the flow sensor 303 from the leading end portion 304B to the outside through an inner space.

The puncture channel needle 304 is covered by, for example, a sheath portion 310 extending from the leading end portion 304B to the elongating portion 312 while exposing the leading end portion 304B.

The sheath 311 is made of a flexible material such as Teflon (registered trademark) or polyethylene. The elongating portion 312 is made of a flexible material such as Teflon (registered trademark), polyolefin, or polyethylene and has a characteristic (permanent deformation or plastic deformation) whose shape is maintained in a deformed state without being recovered (without returning) to an original shape once it is deformed. Materials which may be used to fabricate the elongating portion 312 to exhibit flexible, pliable, and unrestorable characteristics include a material cross-linked by ultraviolet rays through heating such as heat-shrinkable tubing. Such a material may include polyolefin, Teflon (registered trademark), silicon, polyvinyl chloride, polyvinylidene fluoride, and the like.

The sheath 311 covers the most part from the leading end portion 304B up to the elongating portion 312 such that the leading end portion 304B (a sharp needle point) of the puncture channel needle 304 is exposed. However, the sheath 311 is not fixed to the puncture channel needle 304.

In addition, the elongating portion 312 covers the puncture channel needle 304 from a position overlapping with a part of the one end side of the sheath 311 to the elastic portion 304A and is fixed. One end of the elongating portion 312 is fixed to the puncture channel needle 304, and the other end is fixed to the sheath 311. In addition, the elongating portion 312 is fixed such that gaps with the puncture channel needle 304 and the sheath 311 in both fixed ends are hermetically sealed without gaps (i.e., without any gap between the outer periphery of the puncture channel needle 304 and the inner periphery of the sheath 311) along a circumferential direction in order to prevent a liquid from leaking from the gap.

A caulking 306 for fixing the puncture channel needle 304 and the sheath 311 and bonded the sheath 311 is provided in a predetermined position from a movement restricting portion (a depth of puncture needle). The caulking is an example of a holding portion that holds the hollow needle and the sheath portion in an integrated manner. The caulking 306 is made of a material that is deformable as a certain force is applied, such as aluminum or copper.

The caulking 306 is crushed from a ring shape after the puncture channel needle 304 and the sheath 311 are inserted into the ring hole, and a part of the caulking 306 overlaps in the vertical direction, so that the puncture channel needle 304 and the sheath 311 are tightly fixed. As a result, the sheath 311 is fixed to the puncture channel needle 304 without sliding (axially moving). Since the caulking 306 is bonded to the sheath 311, the caulking 306 is not separated from the sheath 311 even when a pressure of the caulking 306 is loosened.

The puncture channel unit 30 is provided with a movement restriction portion 307 positioned a predetermined distance in front of the caulking 306. This predetermined distance is a distance that the puncture channel needle 304 and the sheath 311 protrude from the bottom face 301A of the casing 301, that is, a distance equal to a depth that the puncture channel needle 304 and the sheath 311 are punctured into a user, which is set to 10 mm in the embodiment. The movement restriction portion 307 is fixed to the casing 301 and is arranged such that the puncture channel needle 304 and the sheath portion 310 are inserted into a hole provided in the center and only the puncture channel needle 304 is retracted to its original position without making contact.

The puncture channel unit 30 is provided with a puncture mechanism 320 in front of the elongating portion 312 and to the rear of the caulking 306. The puncture mechanism 320 includes a fixing plate 321, a spring 322, a support plate 323, and a pressing portion 324.

The fixing plate 321 is fixed to the casing 301 and is arranged such that the puncture channel needle 304 and the sheath portion 310 are inserted into (pass through) without contacting a hole provided in the center of the fixing plate 321 and only the puncture channel needle 304 is retracted without making contact.

A spring 322 is arranged in front of the fixing plate 321. The spring 322 is arranged such that the puncture channel needle 304 and the sheath portion 310 are inserted into an inner space without making contact and is inserted between the fixing plate 321 and the support plate 323 in a compressed state shorted than a natural extending length.

The support plate 323 is arranged such that the puncture channel needle 304 and the sheath portion 310 are inserted (pass through) without making contact and supports the pressing portion 324 under the puncture channel needle 304 and the sheath portion 310 on a surface opposite to the surface where the spring 322 adjoins. In addition, the support plate 323 is held not to move to the front side by the puncture release mechanism 330 under the position where the pressing portion 324 is provided on the coplanar surface.

Figure 13:
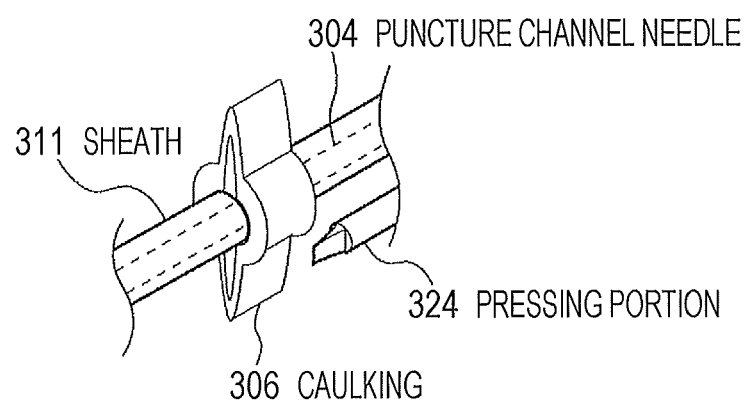
FIG. 13 is a schematic diagram illustrating configurations of a caulking and a caulking released by a pressing portion.

Referring to FIG. 13, the pressing portion 324 has a substantially cylindrical shape, and its leading end has a straight screwdriver shape (straight line shape) vertically long and horizontally short. The pressing portion 324 is supported by the support plate 323 such that its leading end is positioned in a gap between overlapping members in the lower side of the vertically extending portion of the caulking 306.

The puncture release mechanism 330 includes a restricting portion 331, a spring 332, and an actuator 333.

The restricting portion 331 has a longitudinally extending portion and a vertically extending portion so that they make a substantially L-shape. In addition, the restricting portion 331 is rotatably held with respect to a rotational shaft 331A provided in the vicinity of the center of the longitudinally extending portion. The restricting portion 331 is arranged to support the support plate 323 on a surface of the vertically extending portion of the rotational shaft 331A side to restrict the support plate 323 not to move to the front side.

In the restricting portion 331, the spring 332 is connected to a lower surface in the front side from the rotational shaft 331A of the longitudinally extending portion, and the protrusion 333A of the actuator 333 adjoins an upper surface in the rear side from the rotational shaft 331A.

One end of the spring 332 is connected to the restricting portion 331, and the other end is connected to the bottom face 301B side of the casing 301. The spring 332 is arranged to apply a force in a contracting direction at all time.

The actuator 333 receives electric power and shifts the protrusion 333A in the longitudinal direction. The actuator 333 is arranged such that the protrusion 333A adjoins the restricting portion 331.

Figure 14:
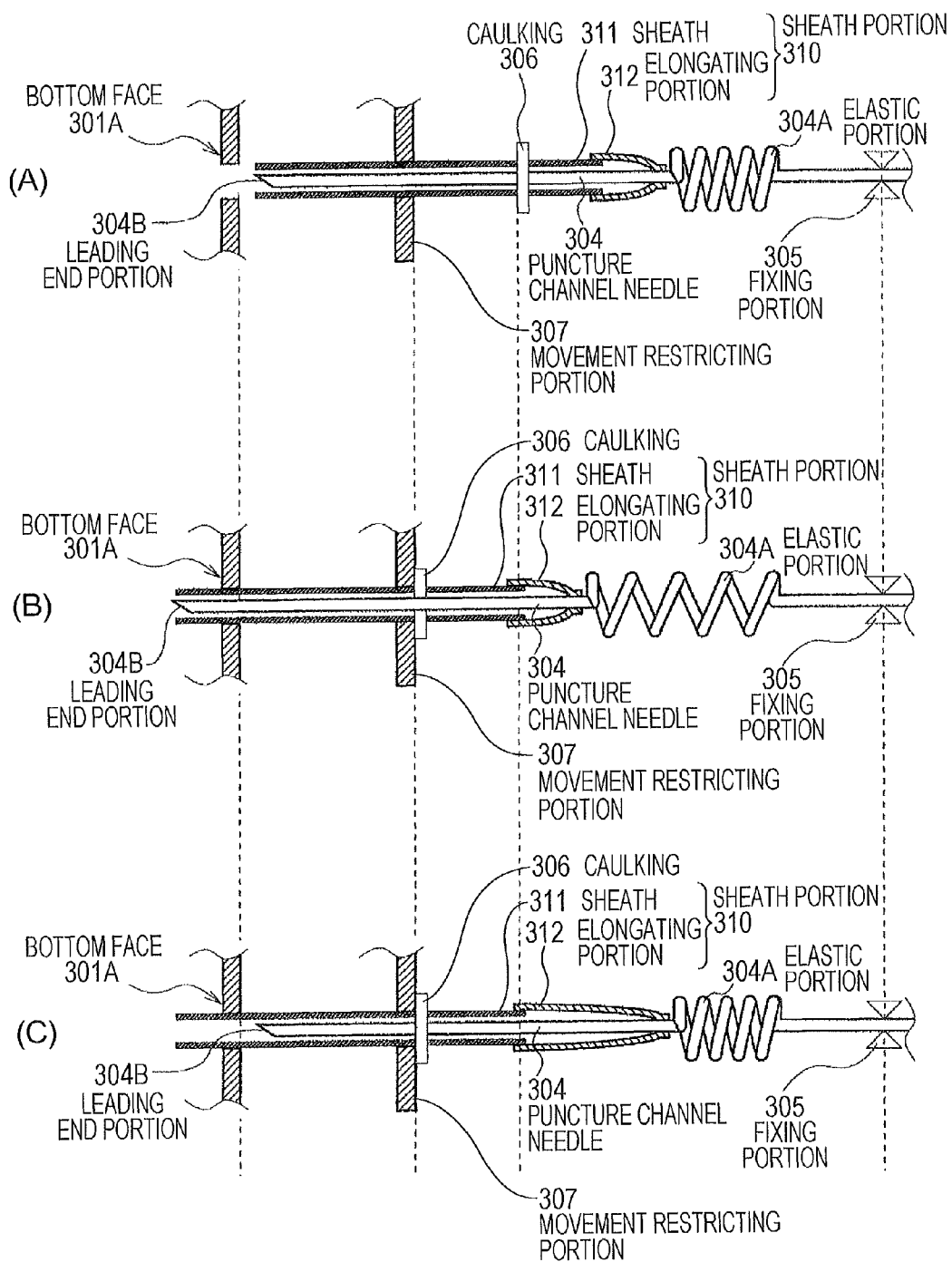
FIGS. 14(A) to 14(C) are schematic diagrams illustrating the hollow needle retraction and puncture state.

In an initial state (FIGS. 12 and 14(A)), the spring 322 is inserted or positioned between the fixing plate 321 and the support plate 323 and is compressed shorter than a natural extending length, the restricting portion 331 adjoins the support plate 323, and the protrusion 333A of the actuator 333 adjoins the restricting portion 331. Although, for purposes of convenience in description, the puncture channel needle 304 and the sheath 311 are illustrated FIGS. 14(A) and 14(C) as a straight state without being bent, a part thereof may be bent in practice as described above.

In the initial state, the actuator 333 is driven so that the protrusion 333A moves to the rear side, and the restricting portion 331 is separated from (no longer held by) the protrusion 333A. Then, the restricting portion 331 is rotated counterclockwise with respect to the rotational shaft 331A by virtue of the restoring force of the spring 332 returning to a natural extending length of the spring 332 so that the restricting portion 331 recedes from the support plate 323.

In the puncture mechanism 320, as the restricting portion 331 recedes from the support plate 323, the contracting spring 322 extends so that it is restored to a natural extending length and presses the support plate 323 and the pressing portion 324 to the front side. The pressing portion 324 is pressed toward the gap between overlapping members in the lower side of the vertically extending portion of the caulking 306 to the front side along with the puncture channel needle 304 and the sheath 311 and expanded the elastic portion 304A until the caulking 306 adjoins the movement restriction portion 307.

In this case, an upper overlapping portion of the vertically extending portion of the caulking 306 moves to the front side along the caulking guide 308 while the puncture channel needle 304 and the sheath 311 are inserted.

The cross section of the caulking guide 308 has a U-shape having an opened bottom, and the caulking 306 is held such that the upper overlapping portion of the vertically extending portion is fitted into the caulking guide 308 from the opening direction of the caulking guide 308.

When the caulking 306 moves to the front side, the elastic portion 304A of the puncture channel needle 304 expands (FIG. 14(B)). In addition, the puncture channel needle 304 and the sheath 311 protrude from the bottom face 301A of the casing 301, and the leading end portion 304B punctures and penetrates into a user's body along with the sheath 311.

In the puncture mechanism 320, the spring 322 continuously expands even after the caulking 306 adjoins the movement restriction portion 307 so that the leading end of the pressing portion 324 penetrates into the gap between the overlapping members at a lower portion of the caulking 306. In this case, the pressing portion 324 opens (expands the space between) the lower overlapping members of the caulking 306 on both sides so as to loosen a pressure of the caulking 306 applied to the puncture channel needle 304 and the sheath 311. The pressing portion 324 is an example of a holding release mechanism that releases the holding by the caulking 306 (holding portion).

As the pressure caused by the caulking 306 is loosened, the fixation of the caulking 306 for the puncture channel needle 304 is released. Then, in the puncture channel needle 304, the elastic portion 304A contracts to a natural extending length, and the leading end portion 304B is restored to an original position in the inner side of the bottom face 301A.

In this case, in the sheath portion 310, the sheath 311 is fixed to the caulking 306 and is not allowed to move. Therefore, as the elastic portion 304A contracts, the elongating portion 312 having one end fixed to the puncture channel needle 304 elongates.

In addition, once the elongating portion 312 elongates, the elongating portion 312 is not restored to its original shape. Therefore, the sheath portion 310 is held such that the leading end portion of the sheath 311 protrudes from the bottom face 301A (FIG. 14(C)).

In this manner, in the puncture channel unit 30, the metal puncture channel needle 304 having the sharp leading end portion 304B punctures a user's body. Then, only the flexible sheath 311 can be continuously inserted into a user's body (i.e., remains positioned in the user's body), and the metal puncture channel needle 304 can be restored (retracted) to a position outside of the user's body.

Therefore, while a user uses the liquid-medicine administration device 2, the metal puncture channel needle 304 does not remain in a user's body, and only the flexible sheath 311 can be continuously inserted (i.e., remains positioned in the user's body). Therefore, it is possible to alleviate a user's pain or uncomfortable feeling and thus improve user-friendliness.

In comparison, in the liquid-medicine administration device of the related art, one end of the sheath is connected to the needle through a dynamic sealing packing. In addition, when the needle is extracted to outside the user's body after the needle and the sheath are punctured into a user's skin, the sheath slides on the sealing packing portion and stays in that position.

Therefore, in the liquid-medicine administration device of the related art, a gap between the needle and the sheath is sealed with the dynamic sealing having movement relative to the needle packing. Therefore, liquid medicine may leak. In addition, a frictional force between the needle and the packing increases if the seal is reinforced. Therefore, the needle may not be inserted into a sufficient depth because can't provide a big strong spring to retract the needle in a small housing.

The liquid-medicine administration device 2 disclosed here is configured so that the puncture channel needle 304 forms a gap, but is fixed in one end of the elongating portion 312. Therefore, liquid medicine does not leak, and a hindrance to a puncture operation caused by friction between the packing and the needle is not generated.

The puncture channel unit 30 (FIGS. 11 and 12) is provided with an angle adjustment mechanism 340 that adjusts a protruding angle (hereinafter, referred to as a protrusion angle) of the puncture channel needle 304 and the sheath 311 with respect to the bottom face 301A. The angle adjustment mechanism 340 is located on a curved surface 301H of the casing 301 in front of the movement restriction portion 307. Since the bottom face 301A abuts on a user's skin, this protrusion angle is equal to an angle (hereinafter, also referred to as a puncture angle) of the puncture channel needle 304 and the sheath 311 against a user's skin.

Figure 15:
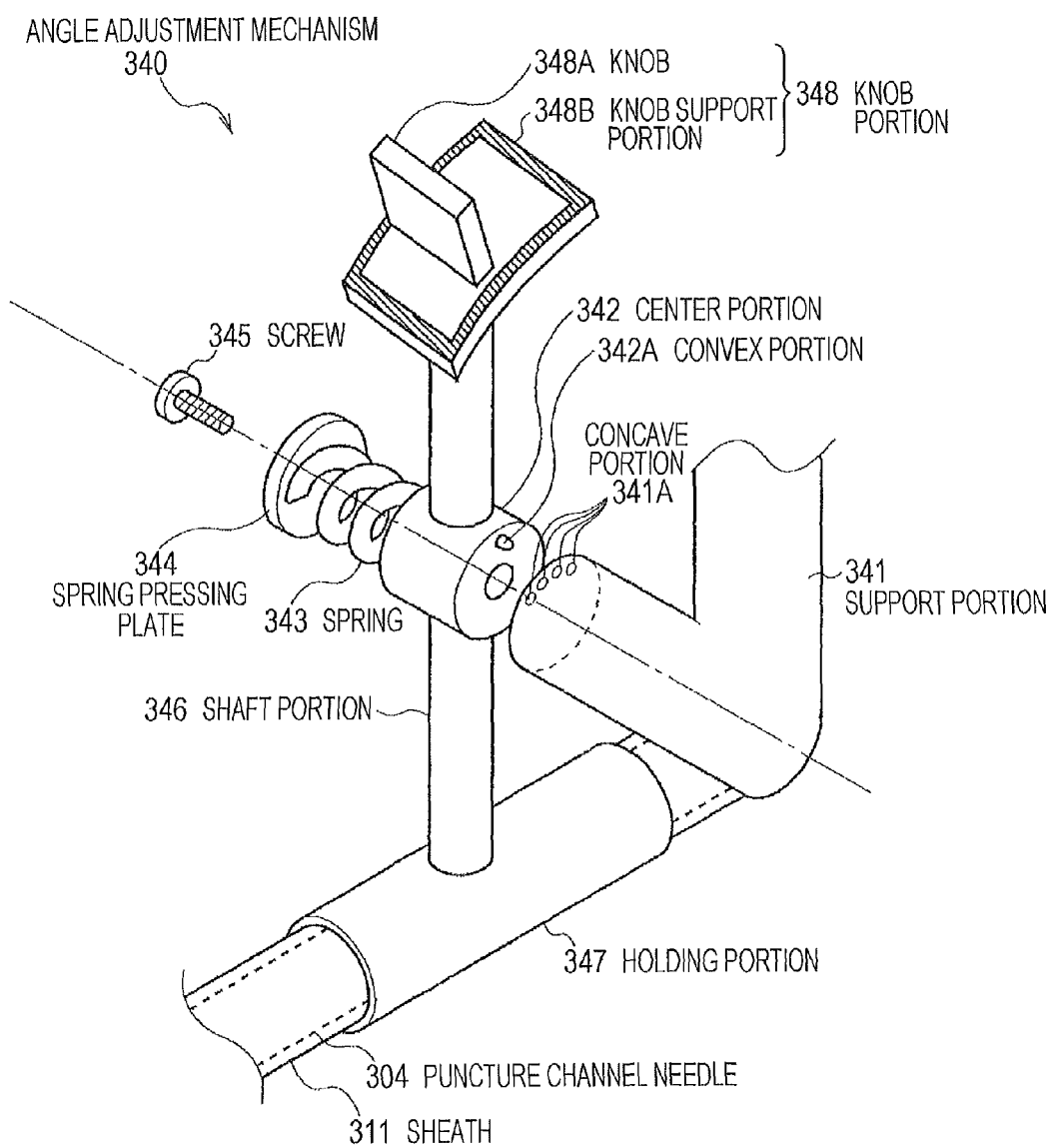
FIG. 15 is a schematic diagram illustrating an angle adjustment mechanism.

Referring to FIG. 15, the angle adjustment mechanism 340 is supported by a support portion 341 which is an L-shaped cylinder having one end fixed to the casing 301. The support portion 341 is provided with a plurality of concave portions or recessed portions 341A (four in this embodiment) for each angle. The concave portions or recessed portions 341A are arranged concentrically on the end surface of the support portion 341 arranged to be perpendicular to the horizontal direction in the opposite side to the one end fixed to the casing 301. The concave portions 341A are provided such that the puncture angle of the puncture channel needle 304 and the sheath 311 is set to 20 to 90° as described below in detail.

The angle adjustment mechanism 340 is provided with a center portion 342 where a convex portion 342A fitted to the concave portion 341A protrudes to face concentrically with the concave portion 341A on the end surface of the support portion 341. While the center portion 342 is pressed to the support portion 341 by a screw 345 by interposing a spring 343 and a spring pressing plate 344, the protruding convex portion 342A is supported by the support portion 341 in the position fitted to one of the concave portions 341A.

The center portion 342 is provided with a shaft portion 346 arranged in a direction perpendicular to a rotational axis of rotation of the center portion 342. The shaft portion 346 has a columnar shape. One end of the shaft portion 346 is connected to a holding portion 347 that holds the puncture channel needle 304 and the sheath 311, and the other end is connected to a knob portion 348 handled by a user in order to adjust the angle.

The holding portion 347 is a tube having an inner diameter larger than the exterior shape of the sheath 311. The puncture channel needle 304 and the sheath 311 are inserted into (positioned in) the holding portion 347 and are held without any fixation.

Figure 16:
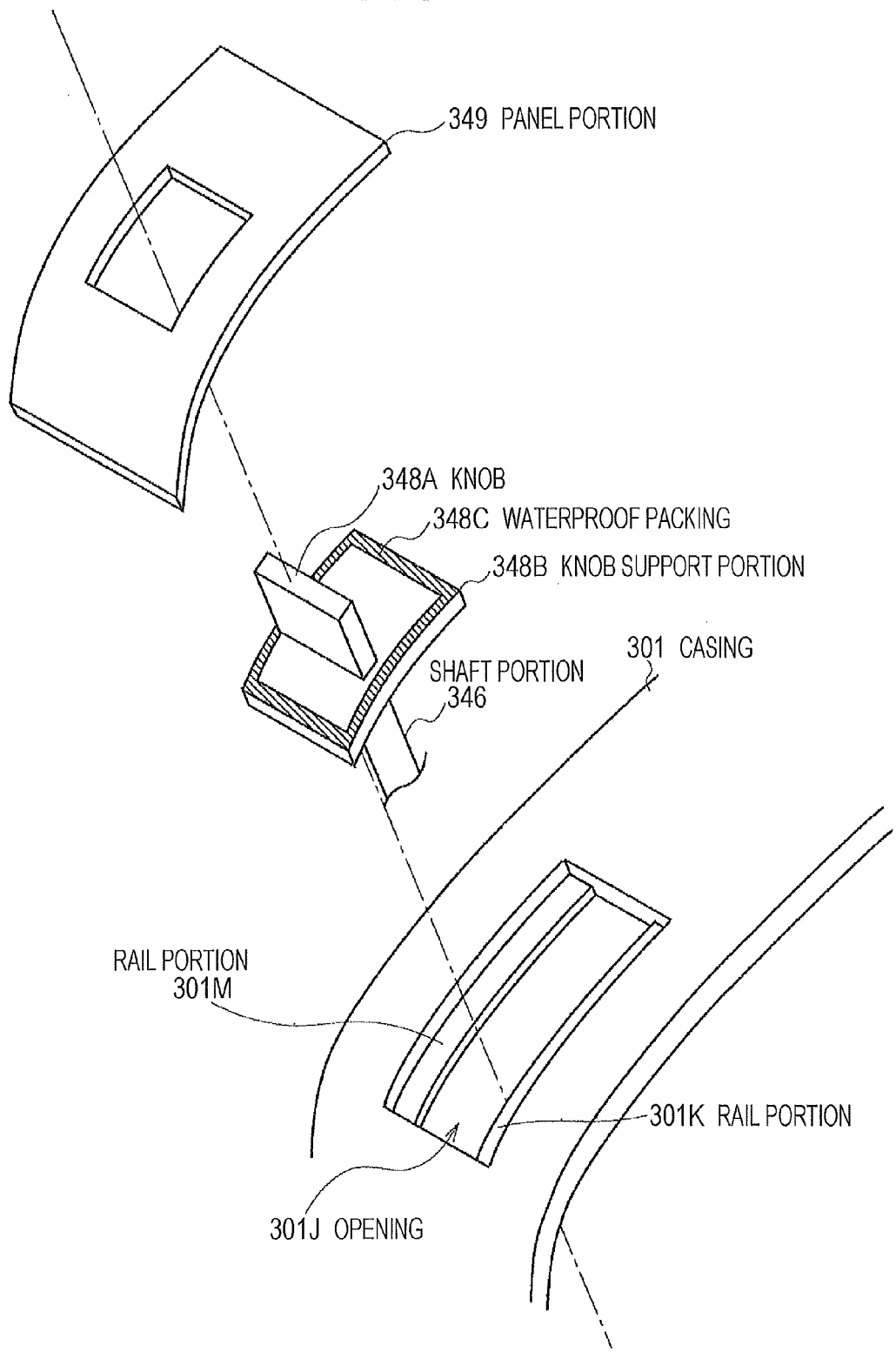
FIG. 16 is a schematic diagram illustrating placement of a knob portion in the angle adjustment mechanism.

Referring to FIG. 16, the knob portion 348 includes a knob 348A handled by a user and a knob support portion 348B that supports the knob 348A. The knob portion 348 is placed such that both ends of the knob support portion 348B are positioned in rail portions 301K and 301M having an L-shaped cross section in both left and right sides of an opening 301J provided on the curved surface 301H of the casing 301.

The knob support portion 348B is interposed between the casing 301 and a panel portion 349 provided on the curved surface 301H of the casing 301. The panel portion 349 is opened such that the knob 348A can move along the curved surface 301H (hereinafter, also referred to a curve direction) and has a shape longer than the rail portions 301K and 301M along the curve direction.

Waterproof packing 348C is provided around the periphery of the upper surface of the knob support portion 348B to prevent liquid from intruding into the inside of the casing 301 from a gap between the knob support portion 348B and the panel portion 349.

In the angle adjustment mechanism 340 having such a configuration, as the knob portion 348 moves along the curve direction by a user, the holding portion 347 is rotated in response to rotation of the shaft portion 346 with respect to the center portion 342.

Figure 17:
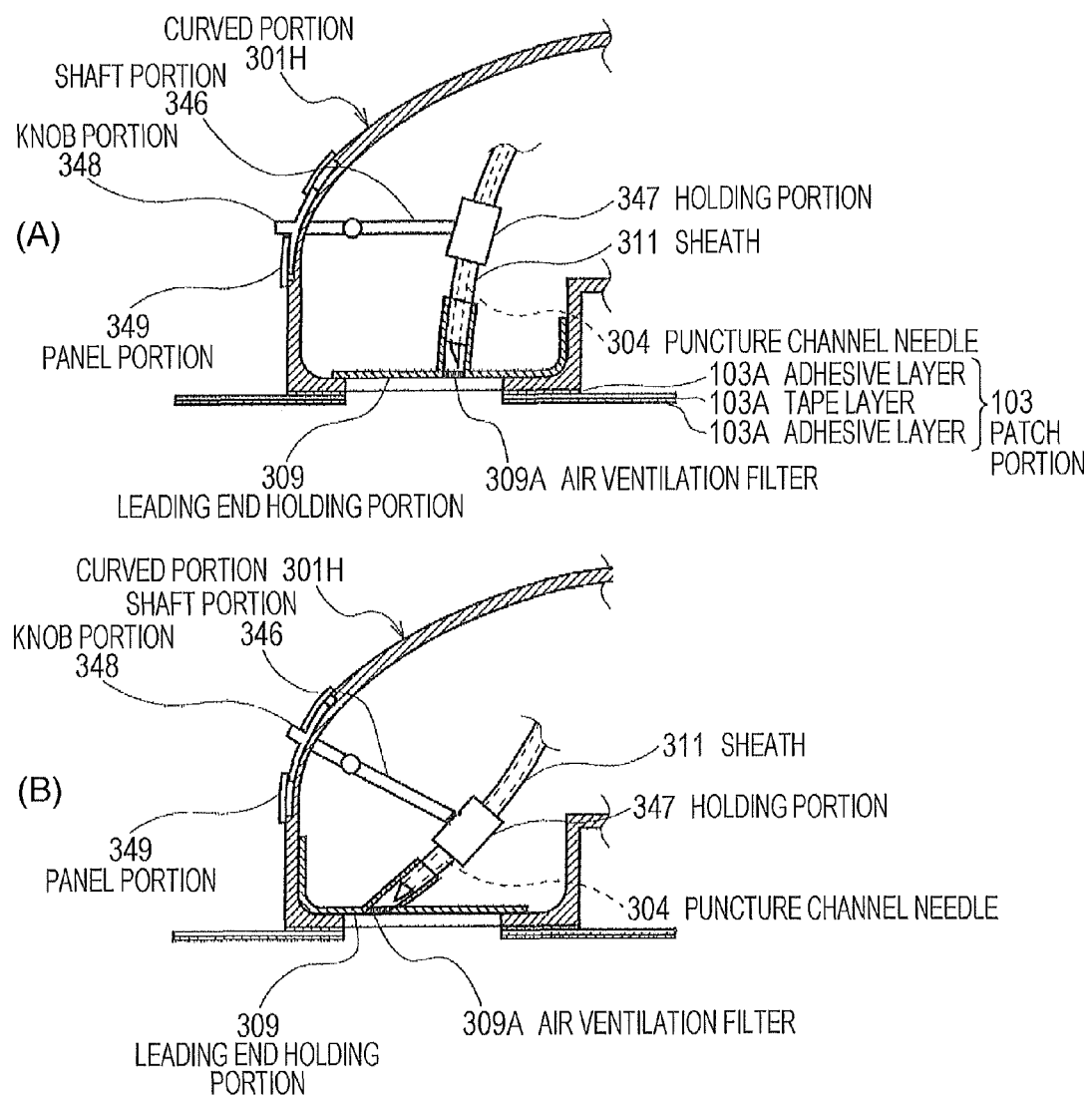
FIGS. 17(A) and 17(B) are schematic diagrams illustrating a change of a protrusion and sheath indwelling angle of the angle adjustment mechanism.

As a result, as illustrated in FIGS. 17(A) and 17(B), the angle adjustment mechanism 340 changes the protrusion angle of the puncture channel needle 304 and the sheath 311 held by the holding portion 347 against the bottom face 301A within a range of 20 to 90°. In addition, FIG. 17(A) illustrates a case where the protrusion angle is set to 90°, and FIG. 17(B) illustrates a case where the protrusion angle is set to 20°.

That is, the angle adjustment mechanism 340 can change, within a range of 20 to 90°, the angle of the puncture channel needle 304 and the sheath 311 against a user's epidermis arranged parallel to the bottom face 301A. A distance between the leading end portion 304B and the bottom face 301A changes depending on the puncture angle, but the puncture channel needle 304 and the sheath 311 are set such that the leading end portion 304B does not extend from or beyond the bottom face 301A at any of the possible puncture angles before puncture.

The leading end portion 304B of the puncture channel needle 304 and the leading end of the sheath 311 are held by a leading end holding portion 309 that seals an opening 301N provided on the bottom face 301A. The leading end holding portion 309 is arranged to adjoin the outer circumference of the sheath 311 and is made of a flexible material such as elastomer.

The leading end holding portion 309 is inserted into or positioned in an L-shaped rib provided in the inside of the bottom face 301A and slips (slides) in the longitudinal direction along the inside of the front face 301G and the rear face 301V of the casing 301 in both directions. The leading end holding portion 309 has flexibility. Therefore, even when the leading end portion 304B of the puncture channel needle 304 and the leading end of the sheath 311 move by the angle adjustment mechanism 340, the leading end holding portion 309 continuously seals the opening 301N following that movement. Therefore, it is possible to prevent liquid from intruding into the inside of the casing 301.

In addition, the leading end holding portion 309 is provided with an air ventilation filter 309A that caps the leading end portion 304B of the puncture channel needle 304 and the leading end of the sheath 311 in front of the leading end portion 304B of the puncture channel needle 304.

Therefore, the air ventilation filter 309A can discharge only the air originally existing in the puncture channel needle 304 to the outside without a liquid medicine being discharged from the puncture channel needle 304 to the outside before a user uses the liquid-medicine administration device 2.

In addition, the air ventilation filter 309A is torn off by the leading end portion 304B when the leading end portion 304B of the puncture channel needle 304 is punctured into a user's body.

In this manner, in the liquid-medicine administration device 2, the angle adjustment mechanism 340 can change the protrusion angle of the puncture channel needle 304 and the sheath 311 against the bottom face 301A within a range of 20 to 90° in response to a user's manipulation.

Meanwhile, a human body has a skin such as epidermis and derma with a thickness of 1.5 to 4 mm from the body surface. Furthermore, subcutaneous tissues are positioned with a thickness of 4 to 9 mm from the body surface, and muscles or the like are positioned in an inner side.

For example, when insulin is injected from the outside, typically, insulin is injected into subcutaneous tissues having a thickness of 4 to 9 mm from the body surface, taking into consideration a burden or wound on a user, an insulin absorption rate, and the like.

A depth of the subcutaneous tissues may be different for each individual person depending on a position, an age, a body type, a sex, and the like. However, in the liquid-medicine administration device of the related art, the needle is punctured to a defined puncture distance at a defined puncture angle. Therefore, some users may fail to inject insulin to the subcutaneous tissues.

In comparison, in the liquid-medicine administration device 2, the puncture angle of the puncture channel needle 304 and the sheath 311 against user's epidermis can change within a range of 20 to 90° using the angle adjustment mechanism 340. Therefore, it is possible to perform puncture into any depth by adjusting the protrusion angle and thus reliably perform puncture into subcutaneous tissues optimally for all users. In recent years, it was observed that the same medicine effect can be obtained by injecting a smaller amount of the liquid medicine into a dermic layer, compared to a case where the liquid medicine is injected into subcutaneous tissues. In response, the puncture distance may be set to derma. Therefore, it is possible to improve user-friendliness using the liquid-medicine administration device 2.

Meanwhile, in the casing 301, in order to attach the driving control unit 20, the connector portion 350 is bonded to the hole 301P provided to face the connector portion 212 of the driving control unit 20 without any gap. As illustrated in FIGS. 10(A) and 10(B), the connector portion 350 is structured such that the waterproof rubber 350B covers the outside of the electric connector 350A formed by integrating a plurality of lines of the connectors 350C for transmitting and receiving electricity and various signals.

In this manner, in the liquid-medicine administration device 2, the puncture channel unit 30 having the puncture channel needle 304 that punctures a user's skin is provided separately from the liquid medicine storage/dispensing unit 10 having the liquid medicine bag 110 for storing a liquid medicine and the driving control unit 20 having the motor 207 for operating the dispensing portion 130 or the board portion 204.

Therefore, in the liquid-medicine administration device 2 disclosed here, for example, even when the puncture fails, the puncture channel unit 30 may be exchanged. Therefore, the liquid-medicine administration device 2 is conveniently used.

In comparison, in the liquid-medicine administration device of the related art, a needle for puncturing a user's skin, a liquid medicine bag for storing a liquid medicine, a motor, and the like are provided in the same casing. Therefore, for example, when the puncture fails, the entire liquid-medicine administration device must inevitably be exchanged. Therefore, user-friendliness is aggravated, and a cost burden also disadvantageously increases.

3. Circuit Configuration of Liquid-Medicine Administration System

Figure 18:
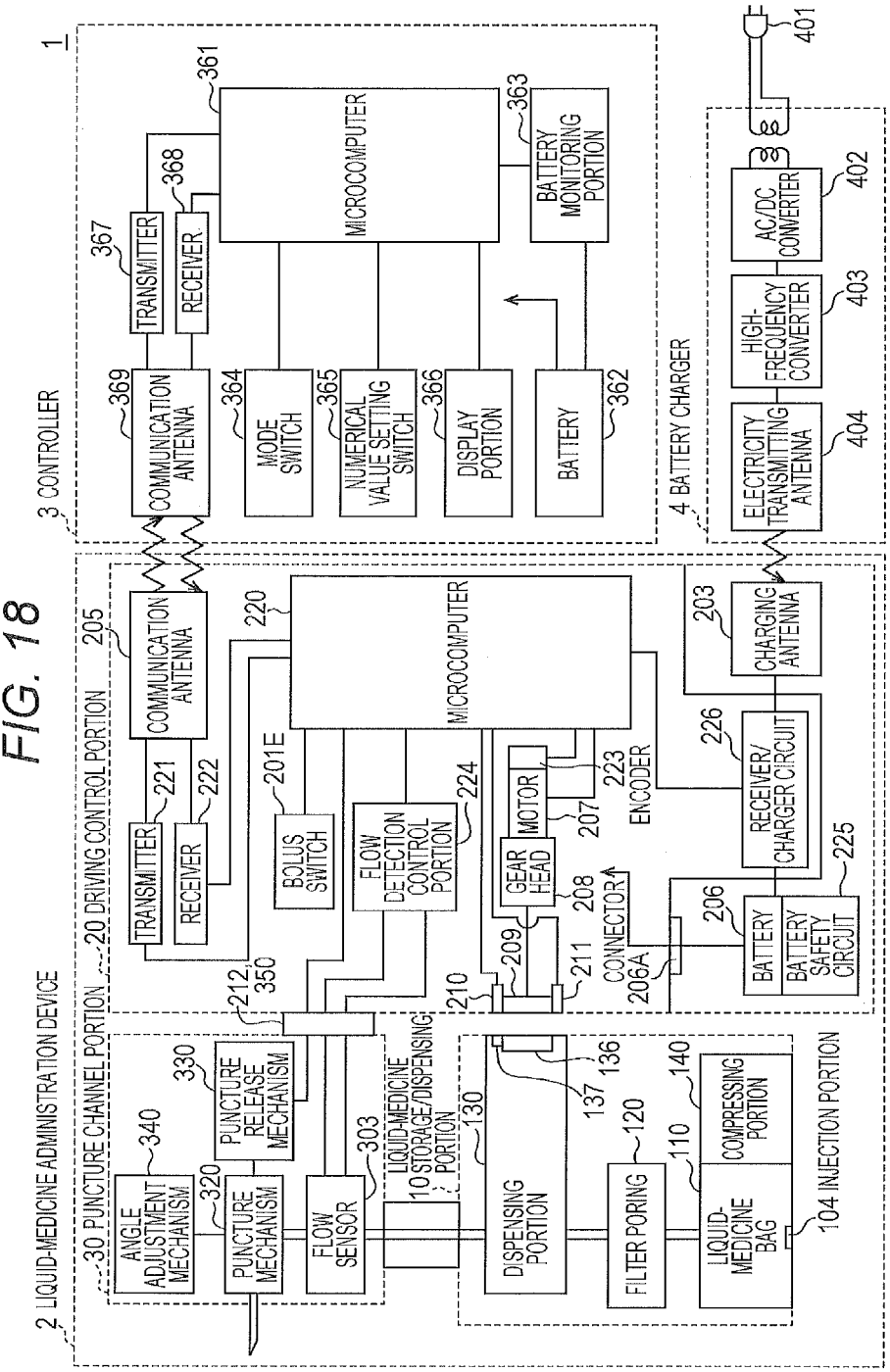
FIG. 18 is a schematic diagram illustrating a circuit configuration and a functional configuration of the liquid-medicine administration system.

Next, a circuit configuration and a functional configuration of the liquid-medicine administration system 1 will be described with reference to FIG. 18.

The controller 3 includes a microcomputer 361, a battery 362, a battery monitoring portion 363, a mode switch 364, a number setting switch 365, a display portion 366, a transmitter 367, a receiver 368, and a communication antenna 369.

The microcomputer 361 is a computer having a CPU, RAM, ROM, and the like. The entire system is integratedly controlled as the CPU reads a basic program stored in the ROM into the RAM and executes it, and various processes are executed as the CPU reads various programs stored in the ROM into the RAM and executes them.

The battery 362 supplies electric power to each part. The battery monitoring portion 363 monitors a discharging condition or a remaining amount of the battery 362 and notifies the result to the CPU 361.

The mode switch 364 is a switch for inserting the hollow needle of the liquid-medicine administration device 2 into the user's living body (for transmitting a signal of inserting the hollow needle and the sheath into the user's living body to the liquid-medicine administration device 2) and for setting a basal mode for continuously administering a liquid medicine for a long time or a bolus mode for temporarily administering a liquid medicine. The number setting switch 365 is a switch for setting number of ID, time, month, day, year, basal rate, insulin-to-carbohydrate ratio, carbohydrate, blood glucose value, a liquid medicine dose per hour, an administration time, and the like.

The microcomputer 361 displays a parameters setting screen by for the mode switch 364 or a number of parameter set by the setting switch 365 on the display portion 366 and transmits the content set to the liquid-medicine administration device 2 via the transmitter 367 and the communication antenna 369.

In addition, as the signal transmitted from the liquid-medicine administration device 2 and the liquid-medicine filling device 5 is received via the communication antenna 369, the microcomputer 361 obtains the signal using the receiver 368 and displays the content of the signal on the display portion 366 to notify a user and execute a process corresponding to the content.

For example, the microcomputer 361 executes a liquid medicine remaining amount notification process and displays the amount of the liquid medicine remaining in the liquid medicine bag 110 on the display portion 366 as described below in detail.

Meanwhile, in the liquid-medicine administration device 2, an electric circuit is operated by electric power supplied from the battery 206, and the microcomputer 220 provided in the driving control unit 20 integratedly controls the entire liquid-medicine administration device 2.

The microcomputer 220 is a computer having a CPU, RAM, ROM, and the like. The entire system is integratedly controlled as the CPU reads a basic program stored in the ROM and stored into the RAM and executes it, and various processes are executed as the CPU reads various programs stored in the ROM and stored into the RAM and executes them.

As a signal received by the communication antenna 205 and transmitted from the controller 3 and the liquid-medicine filling device 5 is received by the receiver 222, the microcomputer 220 operates each part in response to the content of the signal.

Specifically, the puncture angle is adjusted by operating the angle adjustment mechanism 340. As a liquid medicine administration signal is supplied from the controller 3 while the liquid-medicine administration device 2 is attached to a user using the patch portion 103, the microcomputer 220 recognizes whether or not the puncture channel unit 30 is connected to the driving control unit 20 based on connection of the connector portions 212 and 350. In addition, the microcomputer 220 drives the puncture release mechanism 330 in order to puncture a user with the puncture channel needle 304 and the sheath 311 with the controller 3.

In addition, as a signal representing a liquid medicine dose and an administration rate is received from the controller 3, the microcomputer 220 rotates the motor 207 and drives the dispensing portion 130 to administer a liquid medicine into a user's body in order to perform administration at the corresponding liquid medicine dose and the corresponding administration rate.

In this case, in the liquid-medicine administration device 2, the liquid medicine stored in advance in the liquid medicine bag 110 through the injection portion 104 is administered into a user's body through the filter portion 120, the dispensing portion 130, the flow sensor 303, the puncture channel needle 304, the sheath 311, and the like.

While the liquid medicine is administered, the microcomputer 220 monitors a rotation number of the motor 207 using an encoder 223 and detects whether or not a liquid medicine flows using the flow detection control portion 224. In addition, the flow detection control portion 224 heats a thermistor of the flow sensor 303 and monitors a temperature change of the thermistor.

The microcomputer 220 detects whether or not the piston 132 slides based on a magnetic force detected by the magnetic sensors 210 and 211.

When the motor 207 is not normally rotated, when the piston 132 does not normally slide, or when the liquid medicine does not flow, the microcomputer 220 performs detection again. If there is no change, the microcomputer 220 does not stop each part and notifies the controller 3 of this fact using the transmitter 221 and the communication antenna 205.

As it is detected that the piston 132 moves from the bottom point to the top point based on a magnetic force of the position detection magnet 137 detected by the magnetic sensors 210 and 211, the microcomputer 220 transmits a signal representing a liquid medicine dose (corresponding to a discharge volume of the piston 132), to the controller 3 through the transmitter 221 and the communication antenna 205 whenever the detection occurs. Otherwise, the microcomputer 220 integrates the dose computed by the internal RAM of the microcomputer 220 or records the computed dose in a chronological manner, so that the integrated value of the dose or the chronological data of the dose are transmitted to the controller 3 when there is an instruction from the controller 3. The magnetic sensor 221 and the position detection magnet 137 together comprise a detection portion.

In order to charge the battery 206, the microcomputer 220 controls a charge and discharge control circuit 226 such that electric magnetic wave supplied from the battery charger 4 is received via the charging antenna 203, and the battery 206 is charged. In addition, the battery 206 is provided with a battery safety circuit portion 225 so that the battery safety circuit portion 225 prevents an overcharge or over-current during the charging.

The battery charger 4 includes an electric outlet 401, an AC/DC converter 402, a high-frequency converter 403, and a transmitter antenna 404. The battery charger 4 converts an AC current transmitted from the electric outlet 401 into a DC current in the AC/DC converter 402, converts the DC current into a high frequency in the high-frequency converter 403 in order to transmit it to the transmitter antenna 404, and then transmits electric energy to the liquid-medicine administration device 2 via the transmitter antenna 404 (the Wireless discharge).

Therefore, in the liquid-medicine administration device 2, the liquid medicine storage/dispensing unit 10 having the liquid medicine bag 110 and the puncture channel unit 30 having the puncture channel needle 304 and the sheath 311 are single use units for sanitary purposes in use of a liquid medicine. In comparison, the driving control unit 20 that does not relate to a liquid medicine may be reusable by installing and removing the liquid medicine storage/dispensing unit 10 and the puncture channel needle 30. In this case, since the battery 206 of the driving control unit 20 is charged by the battery charger, the battery 206 may be used a plurality of times.

4. Configuration of Liquid-Medicine Filling Device

Next, a liquid-medicine filling device 5 that fills a liquid medicine in the liquid medicine bag 110 of the liquid-medicine administration device 2 will be described.

4-1. Exterior Configuration of Liquid-Medicine Filling Device

Figure 19:
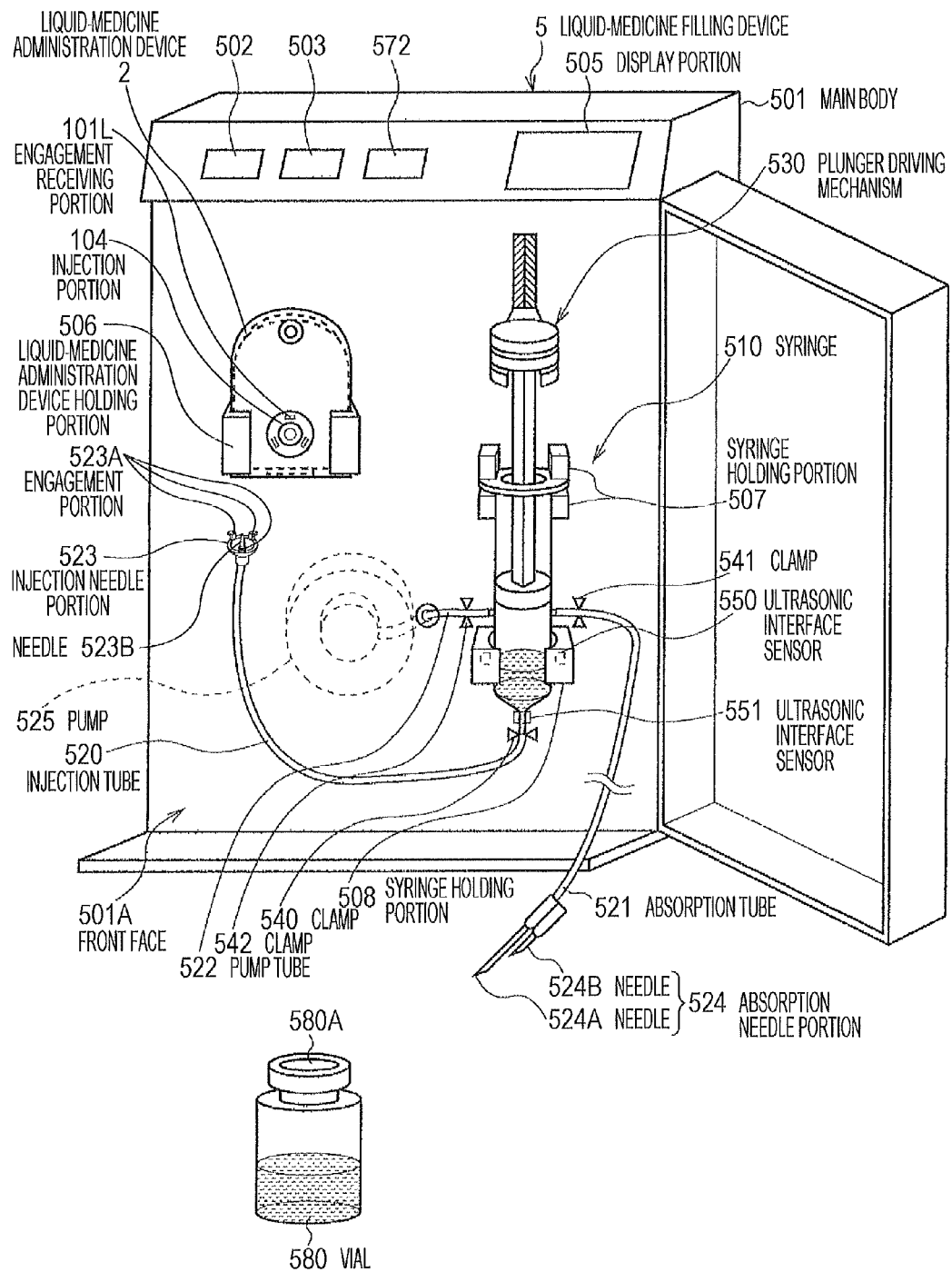
FIG. 19 is a schematic diagram illustrating a configuration of a liquid-medicine filling device.

Referring to FIG. 19, the liquid-medicine filling device 5 includes a power switch 572 that receives a user's input manipulation, a start/stop switch 502, a mode setting switch 503, and a display portion 505 that displays an input content, an operation content, or the like provided on an upper side of the front face 501A of the main body 501 having a substantially rectangular shape.

The main body 501 is provided with a liquid-medicine administration device holding portion 506 that holds the liquid-medicine administration device 2 on the front face 501A. The liquid-medicine administration device holding portion 506 holds the liquid-medicine administration device 2 such that the bottom face 101A of the liquid-medicine administration device 2 faces the front side of the liquid-medicine administration device holding portion 506.

The main body 501 is provided with syringe holding portions 507 and 508 that hold a syringe 510 on the front face 501A. The syringe 510 constitutes a liquid medicine container.

Figure 20:
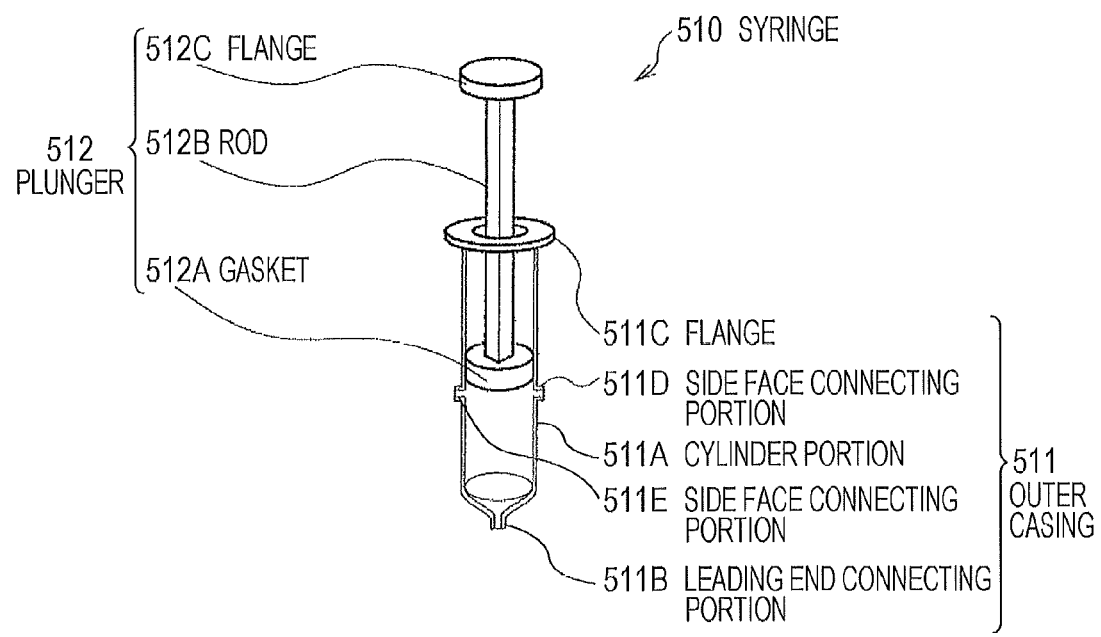
FIG. 20 is a schematic diagram illustrating a configuration of a syringe.

Referring to FIG. 20, the syringe 510 includes an outer casing 511 formed in a cylindrical hollow shape and a plunger 512 slidably inserted into the outer casing 511.

The outer casing 511 includes a cylinder portion 511A, a leading-end connecting portion 511B, a flange 511C, and side face connecting portions 511D and 511E. The end surface of the cylinder portion 511A is opened, and the plunger 512 is inserted from the opening.

In the outer casing 511, a leading-end connecting portion 511B narrowly protruding is formed in the leading end of the cylinder portion 511A, and a flange 511C is formed in the outer circumference of the end of the outer casing 511. In the outer casing 511, the injection tube 520 is connected to the leading-end connecting portion 511B, and the internal space of the cylinder portion 511a communicates with the injection tube 520.

As described below in detail, in the outer casing 511, side face connecting portions 511D and 511E having holes that cause the internal space of the outer casing 511 to communicate with the outer space are formed in side faces of the cylinder portion 511A. In the outer casing 511, a vial connecting tube 521 and a pump tube 522, for example, made of a rubber material with flexibility, are connected to the side face connecting portions 511D and 511E, respectively, and the internal space of the cylinder portion 511A communicates with the vial connecting tube 521 and the pump tube 522.

The plunger 512 includes a gasket 512A, a rod 512B, and a flange 512C. One end of the rod 512B is connected to the gasket 512A, and the other end is connected to the flange 512C. The gasket 512A tightly abuts on an inner wall of the outer casing 511.

The syringe holding portion 507 protrudes from the front face 501A of the main body 501 to suspend the flange 511C of the outer casing 511. The syringe holding portion 507 holds the flange from a vertical direction without rattling using a latch where the resin flange 511C is inserted in order to prevent vertical movement of the outer casing 511.

The syringe holding portion 508 protrudes from the front face 501A of the main body 501 to cover the vicinity of the leading-end connecting portion 511B in the cylinder portion 511A of the outer casing 511.

Therefore, the syringe holding portions 507 and 508 can vertically hold the outer casing 511 such that the leading-end connecting portion 511B is directed downward.

Figure 21:
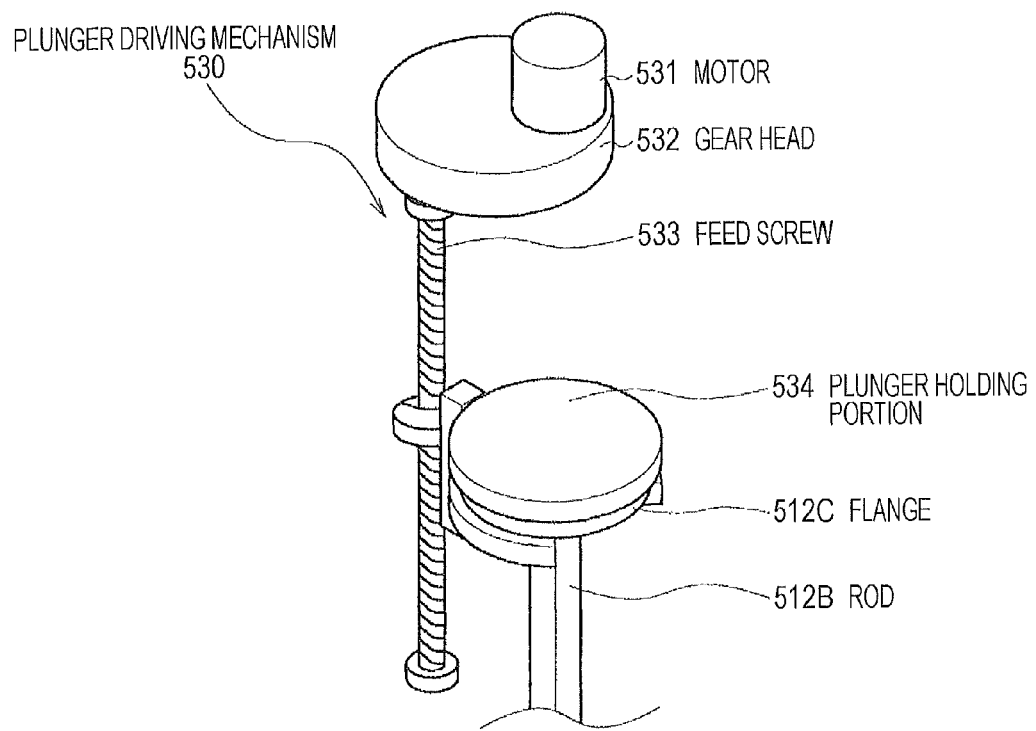
FIG. 21 is a schematic diagram illustrating a configuration of a plunger driving mechanism.

The main body 501 is provided with a plunger driving mechanism 530 for driving the plunger 512 to move vertically on the front face 501A. Referring to FIG. 21, the plunger driving mechanism 530 includes a motor 531, a gear head 532, a feed screw 533, and a plunger holding portion 534. The motor 531, the gear head 532, and the feed screw 533 are provided inside the main body 501 such that a part of the plunger holding portion 534 protrudes from the front face 501A.

The motor 531 rotates the feed screw 533 through the gear head 532 to vertically move the plunger holding portion 534 screwed to the feed screw 533. The plunger holding portion 534 is screwed to the feed screw 533 using a clutch mechanism inside the main body 501, and the flange 512C of the plunger 512 is vertically inserted into the portion protruding from the front face 501A of the main body 501.

The plunger holding portion 534 holds the plunger 512 such that the gasket 512A of the plunger 512 is located over the side face connecting portions 511D and 511E provided in the cylinder portion 511A of the outer casing 511.

Therefore, in the plunger driving mechanism 530, by rotating the motor 531, the plunger 512 vertically moves such that the gasket 512A is located over the side face connecting portions 511D and 511E in the main body 501.

The injection tube 520 is made of a flexible material such as polypropylene, polyolefin, polyvinyl chloride and silicon, and is connected to the leading-end connecting portion 511B of the main body 501. The injection needle portion 523 is connected an end of the injection tube 520 opposite to the end where the leading-end connecting portion 511B is connected. In addition, a clamp 540 that seals the inner hollow of the injection tube 520 is openable/closably provided in the end where the leading-end connecting portion 511B is connected.

In the injection needle portion 523, an engagement portion 523A engaged with the engagement receiving portion 101L provided in the bottom face 101A of the liquid-medicine administration device 2 is protrudingly provided. The needle length of the injection needle portion 523 is set such that a leading end of the needle 523B does not reach the sheet of the liquid medicine bag 110 that the needle faces when the engagement portion 523A is engaged with the engagement receiving portion 101L.

One end of the vial connecting tube 521 is connected to the side face connecting portion 511D, and the other end is connected to the vial septum connecting needle portion 524. A clamp 541 that seals an inner hollow of the vial connecting tube 521 is openably/closably provided in the end where the side face connecting portion 511D is connected.

A pair of needles 524A and 524B are provided in the absorption needle portion 524. The vial connecting tube 521 communicates with the needle 524A. The needle 524B, having a length shorter than that of the needle 524A so that it does not reach liquid medicine inside a vial 580, is not connected to anything. Instead, both ends of the needle 524B are open so as to be used as a ventilation needle.

One end of the pump tube 522 is connected to the side face connecting portion 511E, and the other end of the pump tube 522 is connected to the pump 525 provided inside the main body 501. A clamp 542 that seals an inner hollow of the pump tube 522 is openably/closably provided in the side where the side face connecting portion 511E is connected.

It is noted that the clamps 540, 541, and 542 are opened/closed by an actuator.

Ultrasonic sensors 550 and 551 for measuring the amount of the liquid medicine stored in the outer casing 511 are provided on a surface of the syringe holding portion 508 facing the outer casing 511 such that a pair of transmitter and receiver elements are separated with a predetermined distance by interposing the outer casing 511. This predetermined distance is set such that a space interposed on the same level as that of the ultrasonic sensors 550 and 551 inside the outer casing 511 corresponds to the liquid medicine amount injected into the liquid medicine bag 110 of the liquid-medicine administration device 2.

Using the ultrasonic sensor 550 provided across the cylinder barrel portion 511A of the outer casing 511 of the syringe 510, the transmitter element emits ultrasonic waves to the receiver element to determine whether or not a liquid medicine is filled in the outer casing based on an output of the receiver element.

Specifically, in order to identify whether or not a specified amount of medicine is filled at the time of taking-up or drawing-in the medicine, it is detected that a liquid level of the outer casing 511 increases, and the liquid medicine is filled in a gap between the transmitter element and the receiver element of the ultrasonic sensor 550 if the output of the receiver element of the ultrasonic sensor 550 increases to a constant value. In addition, in order to identify whether or not a specified amount is injected at the time of injection, it is detected that the liquid level (interfacial surface) of the outer casing decreases, and a gap between the transmitter element and the receiver element of the ultrasonic sensor 551 becomes vacant if the output of receiver element decreases.

The ultrasonic sensors 550 and 551 may have each of the transmitter and receiver elements or may have a plurality of receiver elements for a single transmitter element. In addition, although the positions of the ultrasonic sensors 550 and 551 are fixed, they may be vertically movable. For example, they may be supported by an actuator that can move vertically. As a result, it is possible to change a filling amount of the liquid medicine filled in the liquid-medicine administration device 2.

4-2. Circuit Configuration of Liquid-Medicine Filling Device

Figure 22:
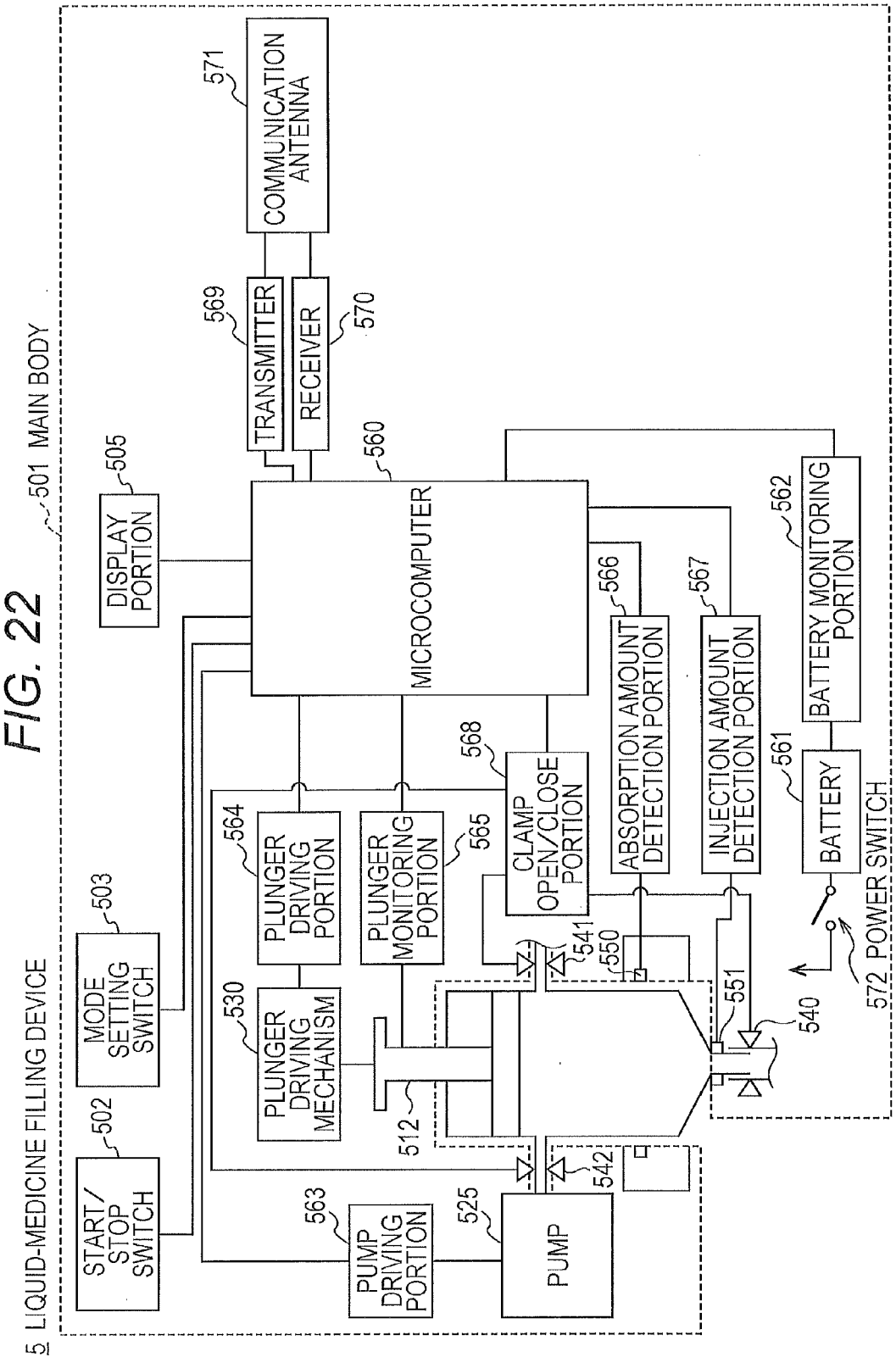
FIG. 22 is a schematic diagram illustrating a circuit configuration and a functional configuration of the liquid-medicine filling device.

Next, a circuit configuration and a functional configuration of the liquid-medicine filling device 5 will be described with reference to FIG. 22.

In the liquid-medicine filling device 5, each part is operated by electric power supplied from the battery 561 through the power switch 572, and the microcomputer 560 integratedly controls the entire liquid-medicine filling device 5.

The microcomputer 560 is a computer having a CPU, RAM, ROM, and the like. The entire system is integratedly controlled as the CPU reads a basic program transferred from the ROM into the RAM and executes it, and various processes are executed as the CPU reads various programs transferred from the ROM into the RAM and executes them.

In addition to the microcomputer 560, the liquid-medicine filling device 5 includes a battery monitoring portion 562, a pump driving portion 563, a plunger driving portion 564, a plunger monitoring portion 565, an absorption amount detection portion 566, an injection amount detection portion 567, a clamp open/close portion 568, a RF transmitter 569, a RF receiver 570, and a communication antenna 571.

The battery monitoring portion 562 monitors whether or not the battery 561 is installed or the battery remaining amount and notifies the microcomputer 560. The pump driving portion 563 drives the pump 525.

The plunger driving portion 564 drives a motor 531 of the plunger driving mechanism 530 to vertically move the plunger 512 through the motor 531, the gear head 532, the feed screw 533, and the plunger holding portion 534.

While the plunger driving portion 564 drives the motor 531 to move, the plunger monitoring portion 565 detects a position of the plunger 512 based on a signal from an encoder installed in a shaft of the motor 531. Alternatively, it is detected whether or not the plunger 512 moves inside the outer casing 511, for example, based on the number of output pulses of the encoder for a case where a DC motor 531 is employed or the number of pulses for a case where a pulse motor is employed. Specifically, the plunger monitoring portion 565 counts the number of pulses, for example, from an encoder and notifies the microcomputer 560 of the movement amount of the plunger 512. Alternatively, when detection of the number of output pulses per unit time greatly decreased, it is determined that the gasket 512A of the plunger 512 is caught in the inner wall of the outer casing 511, and this fact is notified to the microcomputer 560.

The absorption amount detection portion 566 and the injection amount detection portion 567 receive the measurement result from the ultrasonic sensors 550 and detects whether or not an installation height of the ultrasonic sensors 550 is equal to the height of the liquid medicine inside the outer casing 511. The detection result is notified to the microcomputer 560.

The clamp open/close portion 568 receives an instruction from the microcomputer 560 and opens or closes the clamps 540, 541, and 542 using an actuator.

The microcomputer 560 transmits various signals to the liquid-medicine administration device 2 and the controller 3 via the transmitter 569 and the communication antenna 571 and receives a signal from the liquid-medicine administration device 2 and the controller 3 via the communication antenna 571 and the receiver 570, regarding whether or not the signal transmitted to the liquid-medicine administration device 2 and the controller 3 is appropriately received.

5. Sequence of Filling Liquid Medicine Using Liquid-Medicine Filling Device

Next, a sequence of manipulation performed by a user to fill a liquid medicine in the liquid medicine bag 110 of the liquid-medicine administration device 2 using the liquid-medicine filling device and a filling process of the microcomputer 560 will be described with reference to the flowcharts of FIGS. 23 and 24.

As the power switch 572 is turned on, the microcomputer 560 starts a filling process by deploying a filling process program stored in the ROM to the RAM and executing the filling process.

First, a user sets the syringe 510, where injection tube 520, the vial connecting tube 521, and the pump tube 522 are connected, in the main body 501. Specifically, the outer casing 511 is fitted to the syringe holding portion 508, the flange 511C is fitted to the syringe holding portion 507, and the flange 512C of the plunger 512 is inserted into the plunger holding portion 534. In addition, a rubber cap is installed in the injection needle portion 523 so that the injection needle portion 523 is hermetically sealed.

A user cleans, with alcohol cotton, a rubber cap 580A of the vial 580 as a liquid medicine reservoir where the liquid medicine is stored. In addition, a user prods the vial 580 with the absorption needle portion 524 (needles 524A and 524B) to penetrate a septum of the vial 580 and insert a leading end of the needle 524A into the inside of the liquid medicine. It is noted that the length of the needle 524B is set in advance such that needle 524B does not reach the liquid medicine inside the vial 580.

The injection tube 520 is connected to the syringe 510 while a rubber cap is installed in the leading end, and the clamp 540 is set in the injection tube 520. The power switch 572 of the liquid-medicine filling device 5 is turned on, and the mode setting switch 503 is set to a mode (mode 1) of suctioning a liquid medicine into the syringe 510 from the vial 580.

The mode setting switch 503 is set to a filling amount check and setting mode. The filling amount is checked and changed using the mode setting switch 503 and the display portion 505.

Figure 23:
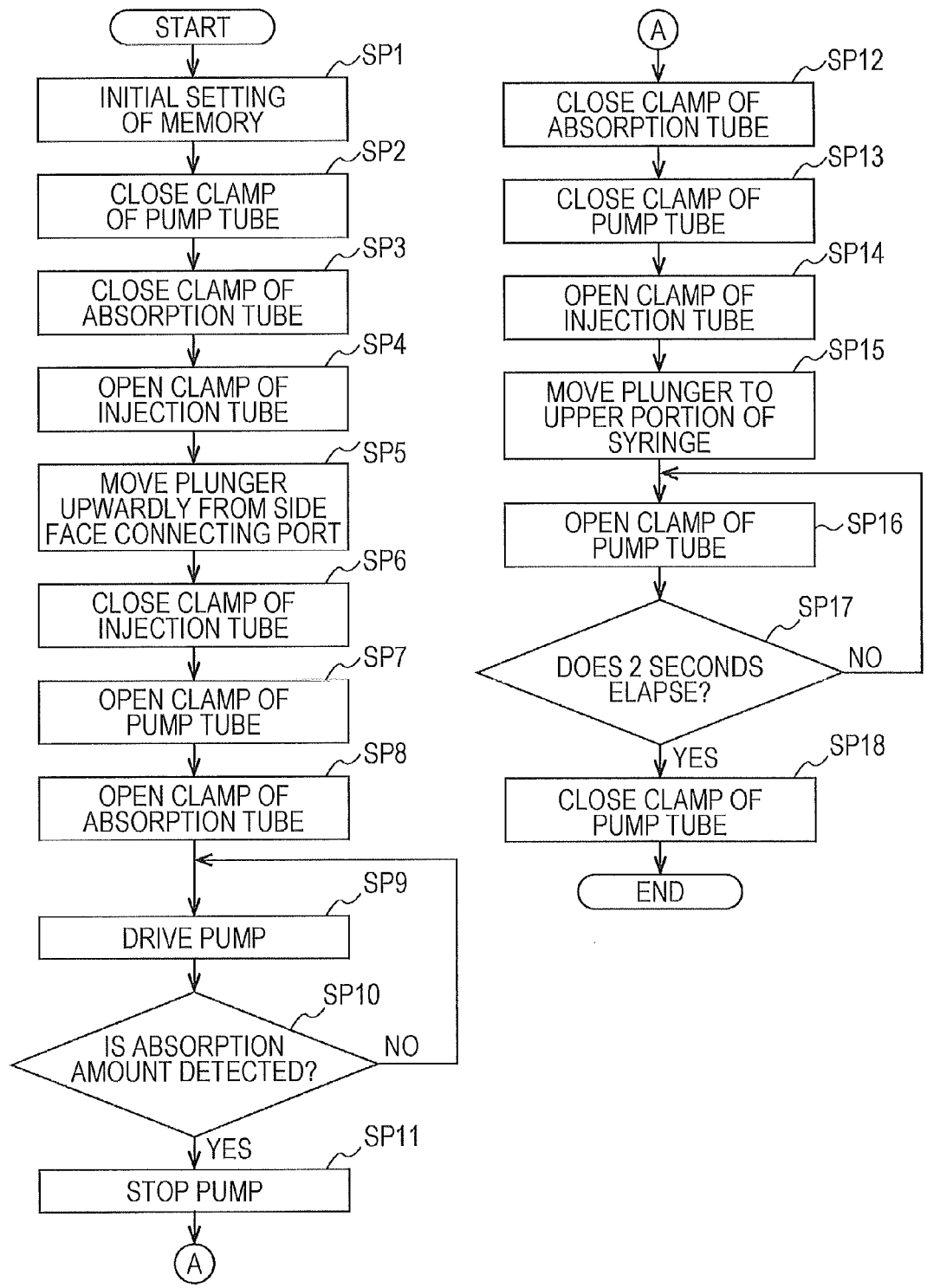
FIG. 23 is a flowchart illustrating a mode for suctioning a liquid medicine into a liquid-medicine filling device from a vial in a filling process sequence.

As a user presses the start/stop switch 502 in this state, the microcomputer 560 executes the mode 1 regarding the filling process illustrated in FIG. 23 so that an initial setup of the memory is executed in step SP1.

The microcomputer 560 closes the clamp 542 of the pump tube 522 in step SP2, closes the clamp 541 of the vial connecting tube 521 in step SP3, closes the clamp 540 of the injection tube 520 in step SP4, and moves the gasket 512A of the plunger 512 to a position higher than the side face connecting ports 511D and 511E (toward the flange 511C) using the plunger driving mechanism 530 in step SP5.

The microcomputer 560 closes the clamp 540 of the injection tube 520 in step SP6, opens the clamp 542 of the pump tube 522 in step SP7, and opens the clamp 541 of the vial connecting tube 521 in step SP8.

In addition, the microcomputer 560 starts absorption by driving the pump 525 using the pump driving portion 563 in step SP9.

As the pump 525 starts absorption, an internal space interposed between the cylinder portion 511A of the outer casing 511 and the gasket 512A of the plunger 512 becomes a negative pressure, so that a liquid medicine flows from the vial 580 to the outer casing 511 through the vial connecting tube 521. In this case, since the air is sucked into the inside of the vial 580 from the needle 524B, a liquid medicine is sucked into the internal space of the outer casing 511 from the vial 580. In addition, the liquid medicine flowing into the internal space of the outer casing 511 drops to the bottom by virtue of gravity. Therefore, even if sucked the air from the tube 521 for example, this air sucked up into the pump 522 via the pump tube 522, the air is not mixed in the liquid medicine in the internal space of the outer casing 511.

In step SP10, the microcomputer 560 detects a height of the liquid level of the liquid medicine stored in the internal space of the outer casing 511 using the ultrasonic sensor 550 and the absorption amount detection portion 566 in order to check whether not the amount of the liquid medicine filled in the liquid-medicine administration device 2 is extracted from the vial 580 to the internal space of the outer casing 511. That is, the microcomputer 560 detects whether or not the liquid medicine is stored in the internal space of the outer casing 511 up to an installation height of the ultrasonic sensor 550.

In addition, the microcomputer 560 actuates the pump 525 until the liquid medicine is extracted into the internal space of the outer casing 511 up to the installation height of the ultrasonic sensor 550. As the amount of the liquid medicine filled in the liquid-medicine administration device 2 is extracted into the outer casing 511 from the vial 580, the microcomputer 560 advances to step SP11 to stop the pump 525 using the pump driving portion 563.

The microcomputer 560 closes the clamp 541 of the vial connecting tube 521 in step SP12, closes the clamp 542 of the pump tube 522 in step SP13, and opens the clamp 540 of the injection tube 520 in step SP14.

The microcomputer 560 moves the plunger 512 upward using the plunger driving portion 564 and the plunger driving mechanism 530 in step SP15 and removes the air existing in the injection tube 520 by forcedly suctioning the air inside the injection tube 520. This work may be performed several times.

The microcomputer 560 opens the clamp 542 of the pump tube 522 in step SP16 and sets the pressure inside the syringe 510 to the atmospheric pressure after 2 seconds in step SP17. Through this operation, the inside of the injection tube 520 is filled with the liquid medicine. Then, the microcomputer 560 closes the clamp 542 of the pump tube 522 in step SP18 and notifies a user of this fact by displaying it on the display portion 505.

After notification, a user removes a rubber cap provided in the injection needle portion 523 and engages the engagement portion 523A with the engagement receiving portion 101L of the liquid-medicine administration device 2. Then, the user inserts the needle 523B of the injection needle portion 523 into the injection portion 104.

In this state, a user sets a mode (mode 2) of injecting a liquid medicine into the liquid-medicine administration device 2 from the liquid-medicine filling device 5 using the mode setting switch 503.

Figure 24:
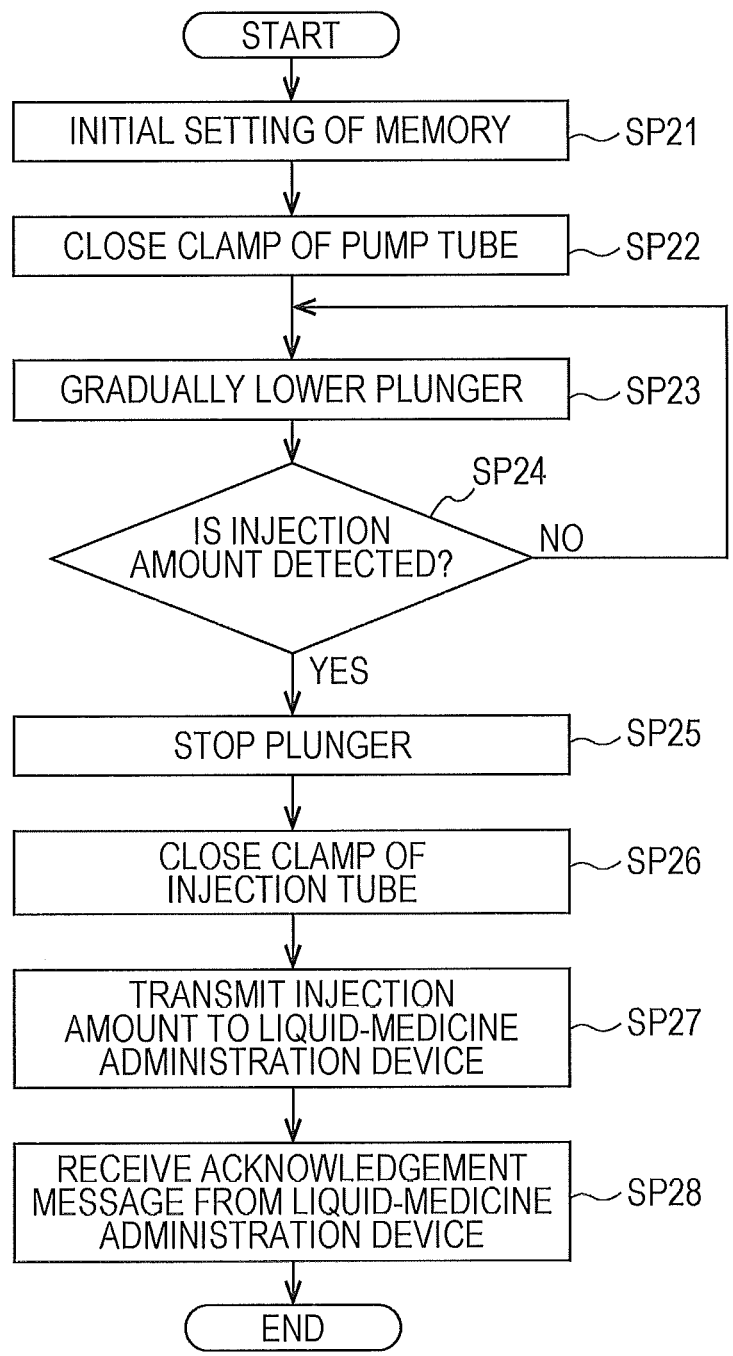
FIG. 24 is a flowchart illustrating a mode for injecting a liquid medicine into a liquid-medicine administration device from the liquid-medicine filling device in a filling process sequence.

As the start/stop switch 502 is pressed, the microcomputer 560 executes the filling process mode (mode 2) illustrated in FIG. 24 and performs an initial setup of the memory in step SP21. In addition, the microcomputer 560 transmits, to the liquid-medicine administration device 2, a signal representing a fact that the liquid medicine is injected.

The microcomputer 560 moves the plunger 512 downward using the plunger driving portion 564 and the plunger driving mechanism 530 in step SP22 and injects the liquid medicine extracted to the outer casing 511 into the liquid-medicine administration device 2 through the injection tube 520.

In the liquid-medicine administration device 2, as a liquid medicine is injected from the injection portion 104, the liquid medicine not only flows to the liquid medicine bag 110, but also sequentially flows to each channel including the nozzle 105, the filter portion 120, the channel pipe 106, the dispensing portion 130, the channel pipe 107, the valve body 108, the nozzle 302 of the puncture channel unit 30, the flow sensor 303, and the puncture channel needle 304 before the liquid medicine bag 110 is inflated.

In this case, the air existing in the liquid medicine bag 110, the nozzle 105, the filter portion 120, and the channel pipe 106 is discharged to the outside from an air ventilation filter 309A and the filter portion 120. Since an air ventilation filter 309A is provided in a tip of the leading end portion 304B of the puncture channel needle 304, the air existing in the flow channel from the dispensing portion 130 to the puncture channel needle 304 is discharged from the air ventilation filter 309A to the outside. It is noted that, although the liquid medicine also flows to a gap between the puncture channel needle 304 and the sheath portion 310, the amount thereof is negligible, and the existing air is also discharged to the outside.

If the liquid medicine is injected through the injection portion 104 after the liquid medicine is filled in each channel, the liquid medicine bag 110 is pressurized and inflated so that the liquid medicine is filled therein.

The microcomputer 560 detects the liquid medicine amount injected from the outer casing 511 to the liquid-medicine administration device 2 based on the height of the liquid level of the outer casing 511 using the ultrasonic sensor 551 and the injection amount detection portion 567 in step SP23.

As the air is filled up to the installation height of the ultrasonic sensor 551, the microcomputer 560 determines that the liquid medicine can be injected into the liquid-medicine administration device 2 as much as a desired filling amount and stops the movement of the plunger 512 in step SP24.

The microcomputer 560 closes the clamp 540 of the vial connecting tube 521 in step SP25, transmits the injection amount of the liquid medicine to the liquid-medicine administration device 2 in step SP26, and receives an injection completion notification from the liquid-medicine administration device 2 in step SP27.

In this manner, the liquid-medicine filling device 5 can fill a desired amount of the liquid medicine in the liquid-medicine administration device 2.

In the liquid-medicine administration device of the related art, a user extracts a liquid medicine from a vial using a syringe and fills the liquid medicine in the liquid-medicine storage portion that stores the liquid medicine.

In this regard, if a user does not inject the air with a syringe in advance, a relatively strong force is necessary in order to extract a liquid medicine from a vial using a syringe. In addition, a cumbersome work is necessary when a liquid medicine amount in a vial is small, and a special attention is necessary to treat a needle for guaranteeing safety. Furthermore, in consideration of sanitation, a delicate skill is demanded to extract a necessary liquid medicine amount from a vial. These increase a user's burden.

Furthermore, the air may be mixed in the liquid-medicine storage portion when a liquid medicine is filled. If the air is mixed in the liquid-medicine storage portion, a problem may occur. For example, it is difficult to inject an accurate amount of the liquid medicine into a user, and it is difficult say that a liquid medicine is appropriately filled. For this reason, a user must pay attention not to mix air into the liquid-medicine storage portion.

In this manner, in order to appropriately fill a liquid medicine in the liquid-medicine storage portion of the liquid-medicine administration device, a user is required to perform a cumbersome operation.

In comparison, in the liquid-medicine filling device 5 disclosed here, it is possible to fill an accurate amount of a liquid medicine in the liquid medicine bag 110 of the liquid-medicine administration device 2 just by causing a user to perform a relatively easy operation including setting the syringe 510, inserting the vial septum connecting needle portion 524 into the vial 580, and inserting the injection needle portion 523 into the injection portion 104.

Therefore, using the liquid-medicine filling device 5, it is possible to alleviate a user's burden compared to the related art, fill an accurate amount of a liquid medicine, and improve user-friendliness.

In the liquid-medicine administration device 2, a liquid medicine may leak from a tip of the needle due to an increase of the pressure in the liquid medicine bag 110 when the liquid medicine is completely filled. In order to prevent such a leakage, the piston 132 is shifted to the top dead point in advance as the injection start signal is received from the liquid-medicine filling device 5. Then, as the filling completion signal is received, the piston 132 is shifted to the bottom dead point.

As a result, the pressure in the liquid medicine bag 110 is lowered to a valve open pressure of the check valve 138.

6. Sequence of Remaining Liquid-Medicine Amount Notification Process

In the liquid-medicine administration system 1, a remaining liquid-medicine amount (remaining amount) in the liquid medicine bag 110 is notified to a user while a liquid medicine is administered into a user using the liquid-medicine administration device 2.

Specifically, each of the microcomputer 220 of the liquid-medicine administration device 2, the microcomputer 361 of the controller 3, and the microcomputer 560 of the liquid-medicine filling device 5 executes a remaining liquid-medicine amount notification process by deploying the remaining liquid-medicine amount notification process program stored in the ROM into the RAM and executing the program.

As the remaining liquid-medicine amount notification process is executed, the microcomputer 560 of the liquid-medicine filling device 5 transmits a signal representing the amount of the liquid medicine (filling amount) filled in the liquid medicine bag 110 to the liquid-medicine administration device 2 via the transmitter 569 and the communication antenna 571.

Specifically, the microcomputer 560 stores the filling amount in the RAM or the like in advance and transmits the filling amount to the liquid-medicine administration device 2 after the filling of the liquid medicine is completed.

The controller 3 transmits an administration program programmed by a user in advance to the liquid-medicine administration device 2 immediately before the liquid-medicine administration device 2 is set on a living body, and administration starts.

The microcomputer 220 of the liquid-medicine administration device 2 computes, as the remaining liquid-medicine amount, a value obtained by subtracting a total administration amount administered already by a user based on the administration program after the administration starts and a bolus injection amount from the filling amount transmitted from the liquid-medicine filling device 5. In addition, the microcomputer 220 monitors whether or not the remaining liquid-medicine amount is larger than a specified value at all times.

In the bolus injection, the microcomputer 220 of the liquid-medicine administration device 2 starts administration of a liquid medicine into a user's body by driving the dispensing portion 130 when a signal representing a request of starting the bolus injection is received from the controller 3 via the communication antenna 205 and the receiver 222, or the bolus switch 201E of the liquid-medicine administration device 2 is pressed.

Specifically, whenever it is detected that the piston 132 moves from the bottom point to the top point based on a magnetic force of the position detection magnet 137 detected by the magnetic sensors 210 and 211, the microcomputer 220 of the liquid administration device 2 records a dose of the liquid medicine dispensed from the dispensing portion 130 as the piston 132 moves from the bottom point to the top point. In addition, the microcomputer 220 subtracts the dose of the liquid medicine from the filling amount obtained from the liquid-medicine filling device 5 and monitors whether or not the remaining amount is within a specified value. Furthermore, a signal representing the remaining amount is transmitted to the controller 3 via the transmitter 221 and the communication antenna 205. The controller 3 displays the remaining amount. In the remaining amount monitoring function of the liquid-medicine administration device, if the remaining amount is equal to or smaller than a specified value, this fact is notified to the controller 3.

As a result, a user can easily check the remaining liquid-medicine amount in the liquid medicine bag 110 by viewing a display portion 366 of the controller 3.

It is noted that the liquid-medicine administration device 2 dispenses a liquid medicine using a piston pump type dispensing portion 130, and the liquid medicine bag 110 is a flexible container. In this configuration, it is difficult to directly measure the remaining liquid-medicine amount of the liquid medicine bag 110. Therefore, the remaining liquid-medicine amount notification sequence is particularly useful.

It is noted that, although the description has been made for a case where the remaining liquid-medicine amount is displayed on the display portion 366 of the controller 3, the display portion may be provided on the liquid-medicine administration device 2 to display the remaining liquid-medicine amount.

7. Alternatives 7-1. Alternative 1

In the aforementioned embodiment, the description has been made for a case where the sheath 311 of the sheath portion 310 covers the most part of the puncture channel needle 304 from the leading end portion 304B up to the front of the elongating portion 312, and the elongating portion 312 covers the puncture channel needle 304 from a position overlapping with a part of one end of the sheath 311 to the elastic portion 304A.

The invention is not limited thereto. Instead, the elongating portion may having a characteristic of maintaining a deformed shape without returning to its original shape once it is deformed. In addition, the elongating portion may elongate and maintain a deformed shape when the elastic portion 304A of the puncture channel needle 304 contracts.

Figure 25:
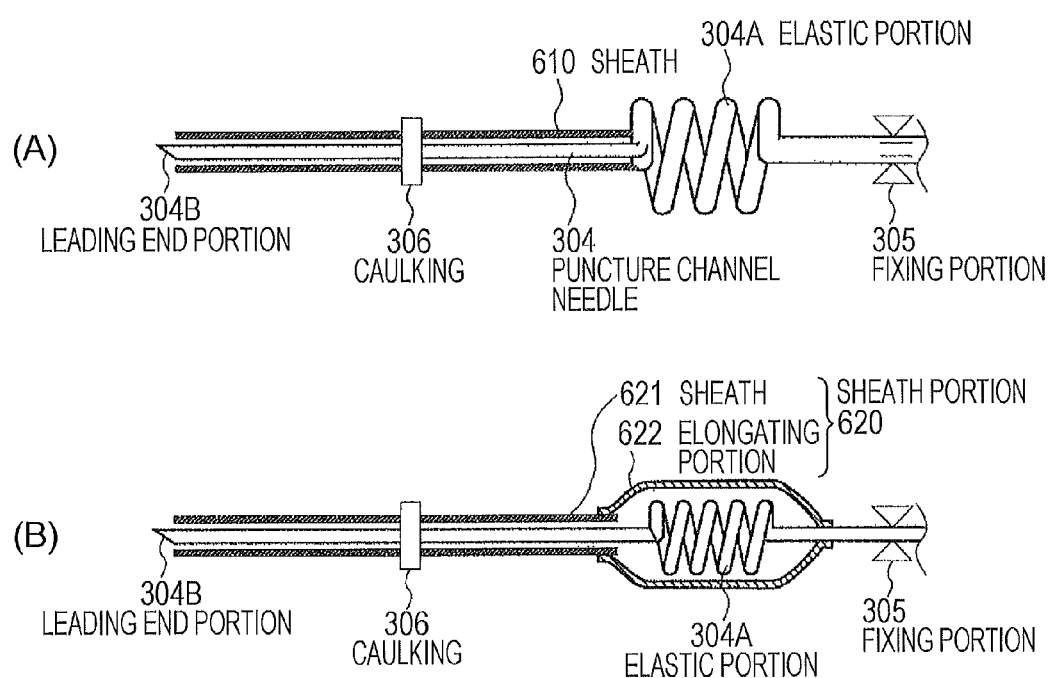
FIGS. 25(A) and 25(B) are schematic diagrams illustrating a configuration of a sheath portion according to another embodiment.

For example, as illustrated in FIG. 25(A), in which like reference numerals denote like elements as in FIGS. 14(A) to 14(C), the sheath 610 of the sheath portion, having a characteristic of maintaining a deformed shape without returning to its original shape once it is deformed, covers the puncture channel needle 304 from the leading end portion 304B up to the fixing portion 305.

The caulking 306 holds the sheath 610 not to slip on the puncture channel needle 304. In addition, the caulking 306 is bonded to the sheath 610 and is not separated from the sheath 610 even when the caulking 306 is loosened.

In addition, if the caulking 306 is pressed to the front side by the pressing portion 324 until it adjoins the movement restriction portion 307, the elastic portion 304A of the puncture channel needle 304 elongates. However, in this case, the sheath 610 does not elongate.

In addition, as the pressing portion 324 is inserted into a gap of the overlapping portion in the lower side of the caulking 306 to loosen the pressure of the caulking 306, the elastic portion 304A of the puncture channel needle 304 contracts. In this case, since the sheath 610 is bonded to the caulking 306, the front side from the caulking 306 is not deformed, and a part of the sheath 610 from the caulking 306 to the fixing portion 305 elongates in response to contraction of the elastic portion 304A. As a result, it is possible to continuously insert only the flexible sheath 610 into a user's body and recover the metal puncture channel needle 304 out of a user's body.

As another example, as illustrated in FIG. 25(B), a part of the sheath portion 620 from the leading end portion 304B of the puncture channel needle 304 right up to the elastic portion 304A is covered by the sheath 621, and the elastic portion 304A is covered by the elongating portion 622 having a characteristic of maintaining a deformed shape without returning to its original shape once it is deformed.

The elongating portion 622 is fixed such that one end of the fixing portion 305 side is fixed to the puncture channel needle 304, and the other end covers the sheath 621. It is noted that the caulking 306 is not necessarily fixed to the sheath 621.

When the caulking 306 moves to the front side, the elastic portion 304A of the puncture channel needle 304 elongates. Accordingly, the elongating portion 622 also elongates.

In addition, as the pressing portion 324 is inserted into a gap of the overlapping member in the lower side of the caulking 306 and loosen the pressure of the caulking 306, the elastic portion 304A of the puncture channel needle 304 contracts. In this case, the sheath portion 620 maintains its shape, and the leading end of the sheath portion 620 protrudes from the bottom face 301A and is maintained in this state.

As a result, when a user's body is punctured using the puncture channel unit 30, the puncture is performed using the metal puncture channel needle 304 having a sharp leading end portion 304B. Then, only the flexible sheath 621 can be continuously inserted into (remain inserted into) the inside of a user's body, and the metal puncture channel needle 304 can be retracted to the outside of a user's body.

7-2. Alternative 2

In the embodiment described above, the protrusion angle of the puncture channel needle 304 and the sheath 311 against the bottom face 301A is adjusted using the angle adjustment mechanism 340 in order to perform the puncture to a certain depth from epidermis. However, the invention is not limited in this regard. Instead, while the protrusion angle is fixed, the puncture distance may change in order to perform the puncture to a certain depth from the epidermis.

Figure 26:
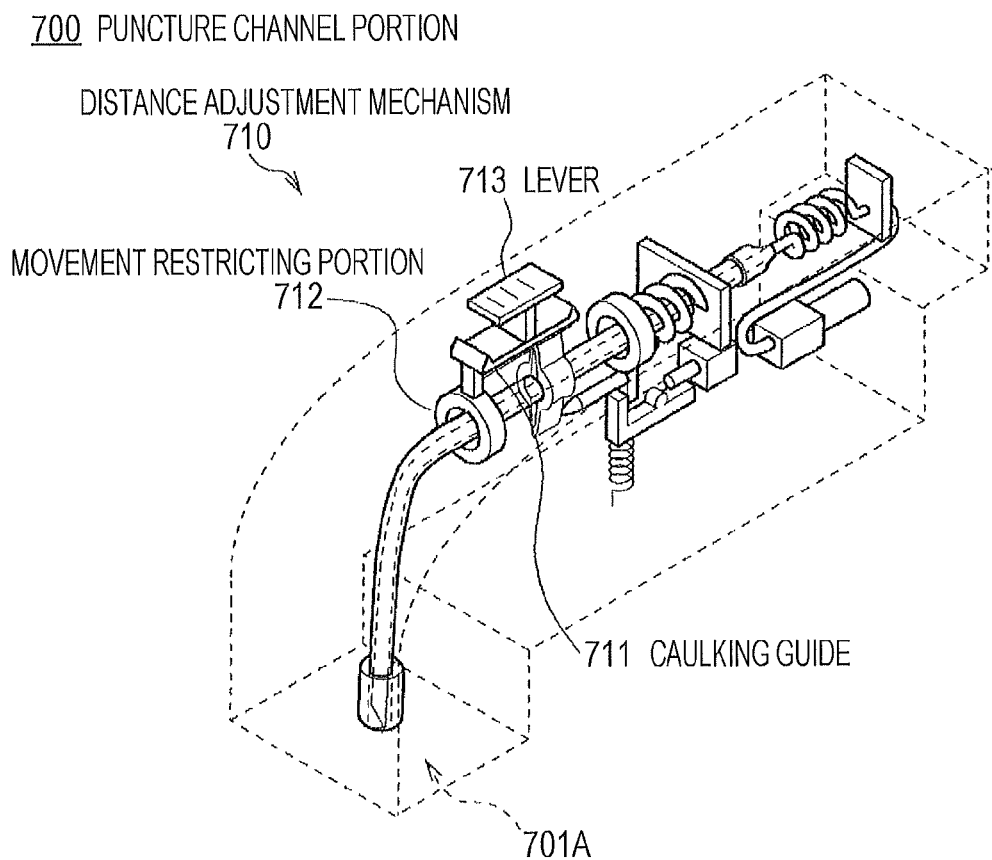
FIG. 26 is a schematic diagram illustrating a puncture channel unit according to another embodiment.
Figure 27:
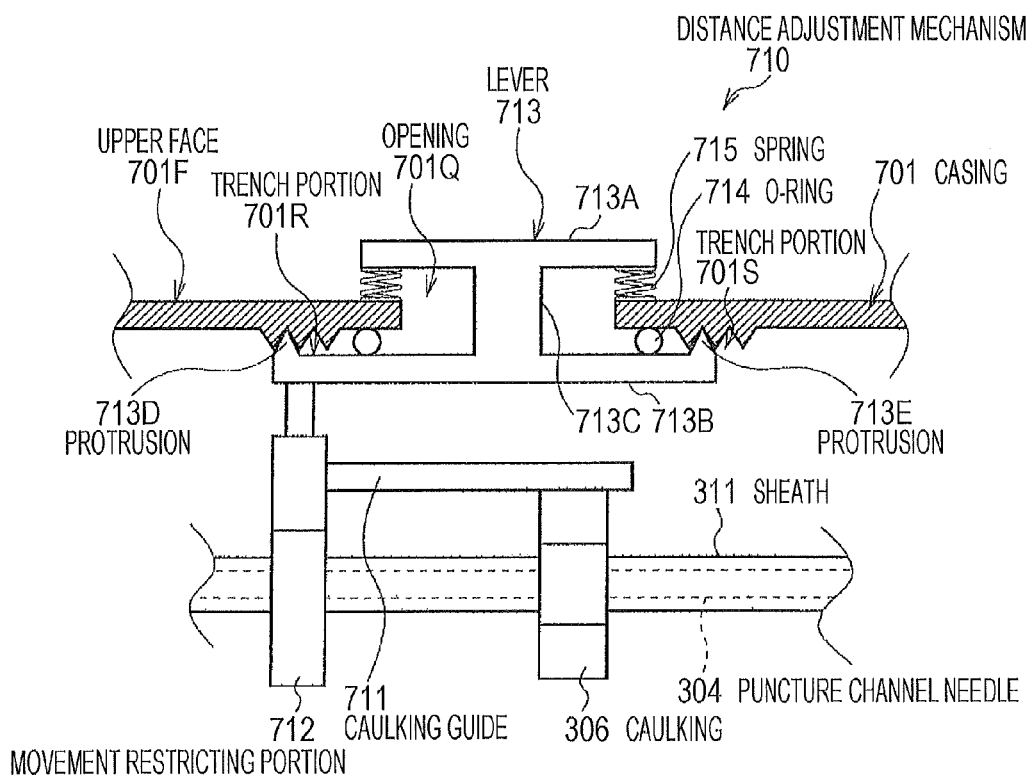
FIG. 27 is a schematic diagram illustrating a distance adjustment mechanism.

Specifically, as illustrated in FIGS. 26 and 27, the puncture channel unit 700 is different from the puncture channel unit 30 in that a distance adjustment mechanism 710 is provided instead of the angle adjustment mechanism 340. The distance adjustment mechanism 710 is held by a lever 713 such that a caulking guide 711 and a movement restriction portion 712 are movable along a longitudinal direction.

The lever 713 has a cross section having a substantially H-shape, in which a manipulation portion 713A and a holding portion 713B extending in a longitudinal direction are arranged in inner and outer sides, respectively, of the opening 701Q provided on an upper face 701F of the casing 701, and the manipulation portion 713A and the holding portion 713B are connected by the connecting portion 713C arranged to penetrate the opening 701Q.

In the distance adjustment mechanism 710, an O-ring 714 for preventing a liquid from flowing from the outside to the inside of the casing 701 is provided between the holding portion 713B and the casing 701. In addition, in the distance adjustment mechanism 710, a spring 715 for pressing the holding portion 713B to the casing 701 side is provided between the manipulation portion 713A and the casing 701.

The lever 713 is provided with protrusions 713D and 713E having a substantially triangular cross section on a surface of the holding portion 713B facing the casing 701 in both ends of the longitudinal direction. In addition, the casing 701 is provided with a plurality of trench portions (notches) 701R and 701S arranged in positions facing the protrusions 713D and 713E to extend in the longitudinal direction and engaged with the protrusions 713D and 713E. In addition, the casing 701 is not provided with the opening 301J where the knob support portion 348B of the angle adjustment mechanism 340 is placed.

In the lever 713, the movement restriction portion 712 is fixed to the holding portion 713B provided in the inside of the casing 701. The movement restriction portion 712 has a hole where the puncture channel needle 304 and the sheath 311 are inserted (positioned).

In the movement restriction portion 712, the caulking guide 711 for guiding the caulking 306 to move along the longitudinal direction is provided on a surface of the caulking 306 side.

Therefore, in the distance adjustment mechanism 710, as a user manipulates the manipulation portion 713A of the lever 713 along the longitudinal direction, the caulking guide 711 and the movement restriction portion 712 move while the protrusions 713D and 713E are engaged with the trench portions 701R and 701S.

In this case, in the distance adjustment mechanism 710, the distance between the caulking 306 and the movement restriction portion 712 changes. Therefore, it is possible to change a movement distance of the caulking up to the movement restriction portion 712 when the caulking 306 is moved by the puncture mechanism 320.

As a result, in the distance adjustment mechanism 710, it is possible to change the puncture distance of the puncture channel needle 304 and the sheath 311 protruding from the bottom face 701A of the casing 701. Therefore, even when the puncture angle is fixed, it is possible to perform the puncture up to a certain depth from a body surface.

Furthermore, both the puncture angle and the puncture distance may change. In this case, both the angle adjustment mechanism 340 and the distance adjustment mechanism 710 described above may be provided together.

7-3. Alternative 3

In the aforementioned embodiment, the description has been made for the angle adjustment mechanism 340, in which the puncture angle of the puncture channel needle 304 and the sheath 311 is adjusted by rotating the holding portion 347 that holds the puncture channel needle 304 and the sheath 311 with respect to the center portion 342. However, the invention is not limited thereto.

Figure 28A:
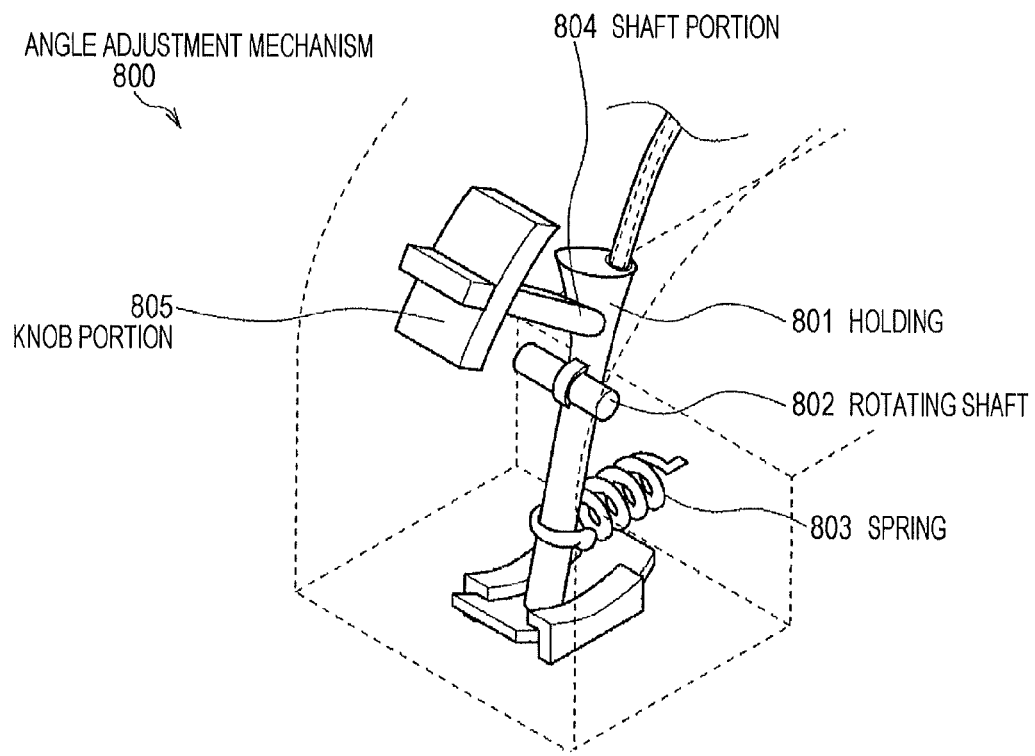
FIGS. 28(A) and 28(B) are schematic diagrams illustrating an angle adjustment mechanism according another embodiment.
Figure 28B:
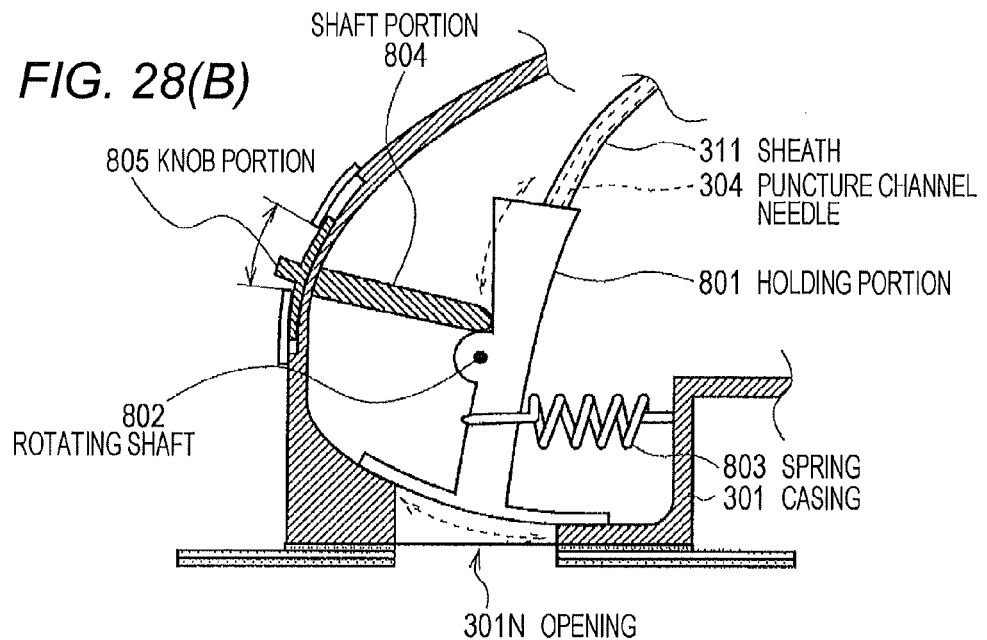
Figure 29:
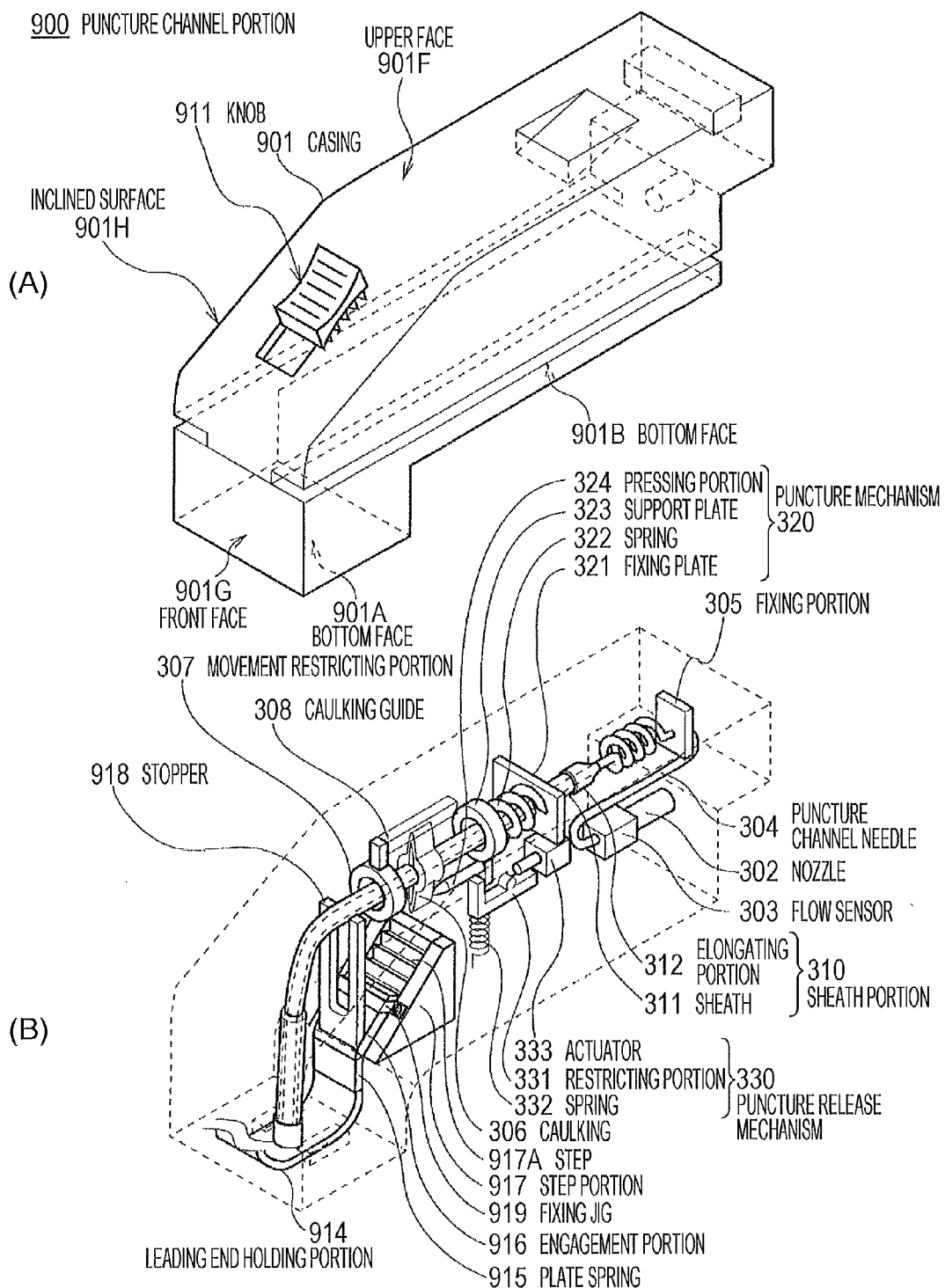
FIGS. 29(A) and 29(B) are schematic diagrams illustrating a puncture channel unit according to another embodiment.
Figure 30:
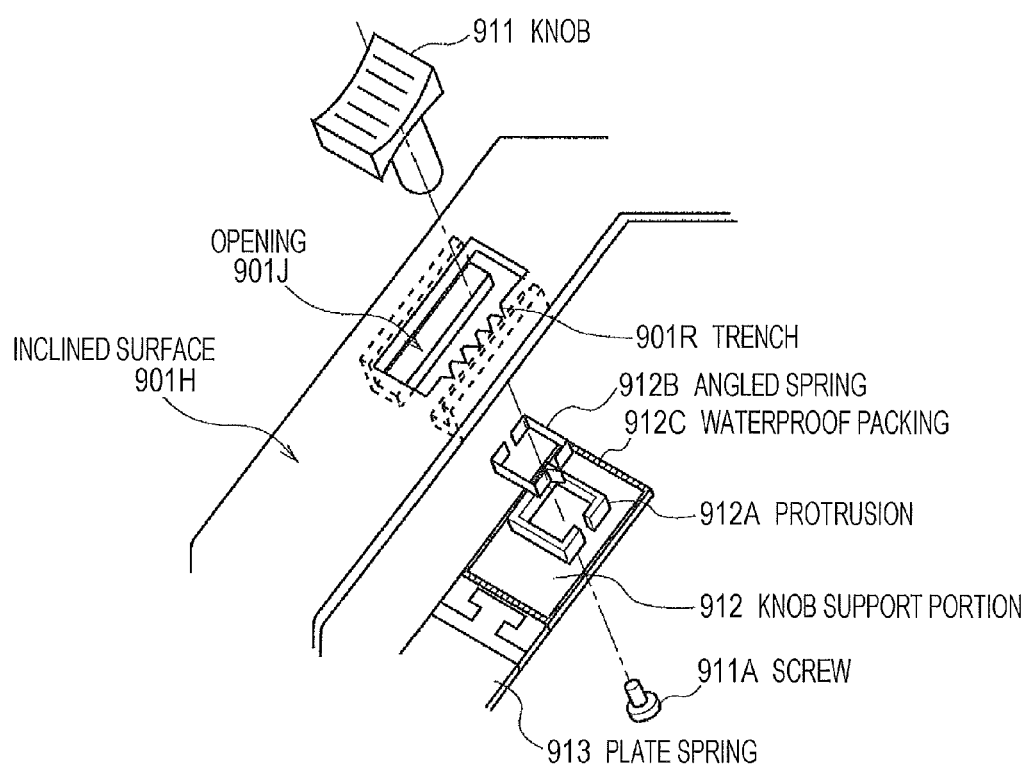
FIG. 30 is a schematic diagram illustrating a knob and a knob support portion according to another embodiment.
Figure 31:
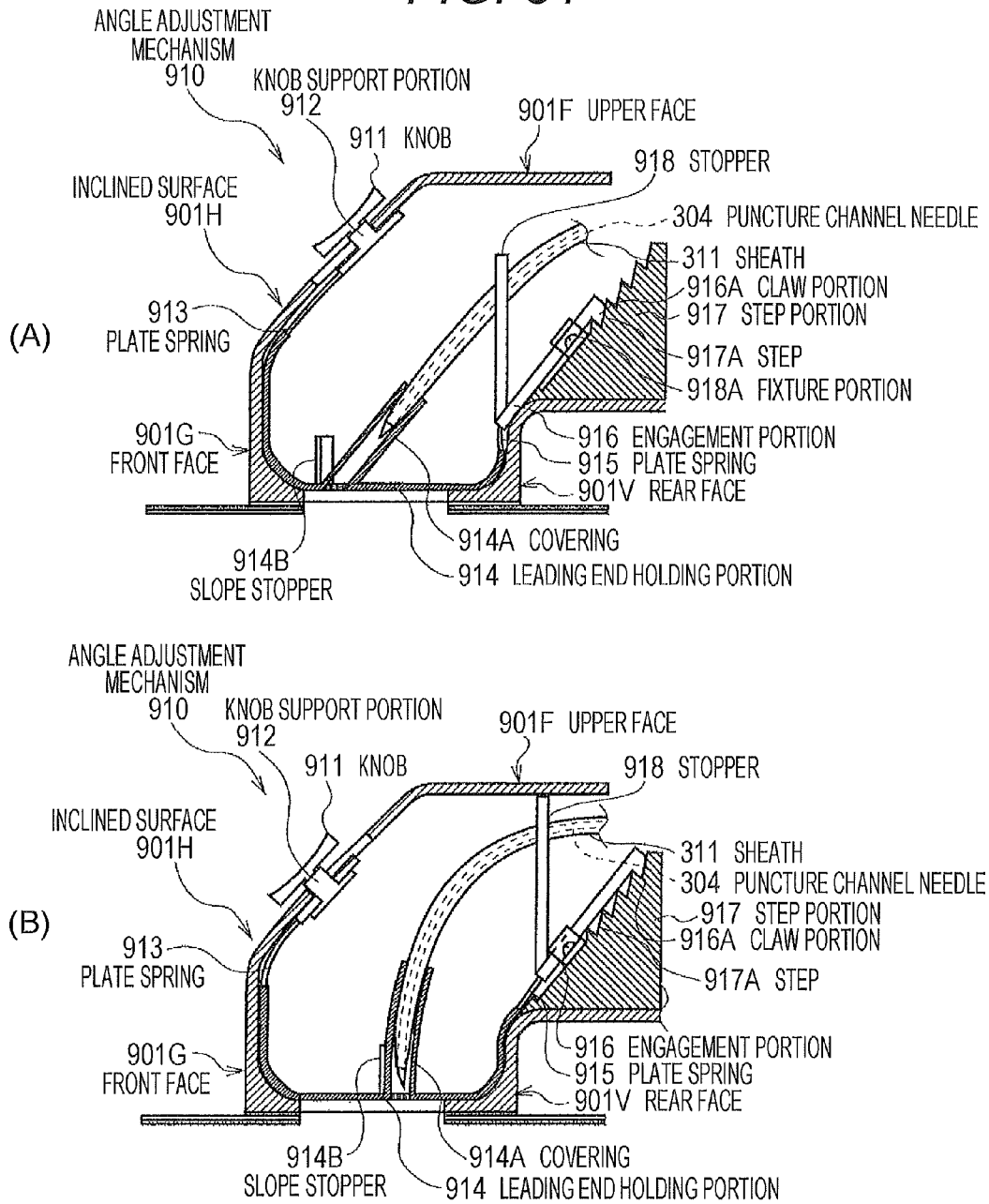
FIGS. 31(A) and 31(B) are schematic diagrams illustrating a change of a protrusion and sheath indwelling angle using an angle adjustment mechanism according to another embodiment.

For example, as illustrated in FIGS. 28(A) and 28(B), in an angle adjustment mechanism 800, a holding portion 801 made of a flexible material to hold the puncture channel needle 304 and the sheath 311 and seal the opening 301N of the casing 301 is provided rotatably with respect to the rotational shaft 802 fixed to the casing 301.

In the holding portion 801, a certain biasing force is applied by a spring 803 to a lower side of the holding portion 801 with respect to the rotational shaft 802 in the rear direction, and an upper side of the holding portion 801 with respect to the rotational shaft 802 abuts on the shaft portion 804 that moves along the curve direction in response to a user's manipulation. One end of the shaft portion 804 abuts on the holding portion 801, and the other end of the shaft portion 804 is connected to the knob portion 805.

In the angle adjustment mechanism 800, as the shaft portion 804 moves upward along a curve direction using the knob portion 805, the upper side of the holding portion 801 with respect to the rotational shaft 802 moves to the rear direction. As a result, the holding portion 801 is rotated with respect to the rotational shaft 802 (clockwise in FIG. 27(B)).

As a result, in the angle adjustment mechanism 800, it is possible to reduce the protrusion angle of the puncture channel needle 304 and the sheath 311 against the bottom face 301A and reduce the puncture angle of the puncture channel needle 304 and the sheath 311 against a user's skin surface.

Meanwhile, in the angle adjustment mechanism 800, as the shaft portion 804 moves downward along the curve direction using the knob portion 805, the shaft portion 804 moves to the front side to recede from the upper side of the holding portion 801 with respect to the rotational shaft 802. Therefore, the holding portion 801 is rotated with respect to the rotational shaft 802 by virtue of a biasing force of the spring 803 (counterclockwise in FIG. 28(B)).

As a result, in the angle adjustment mechanism 800, it is possible to increase the protrusion angle of the puncture channel needle 304 and the sheath 311 against the bottom face 301A and increase the puncture angle of the puncture channel needle 304 and the sheath 311 against a user's skin surface.

7-4. Alternative 4

As another example, as illustrated in FIGS. 29(A) to 31(B), the casing 901 of the puncture channel unit 900 is provided with an opening 901J having a predetermined width and a predetermined length on an inclined surface 901H inclined from the upper face 901F to the front face 901G. A plurality of triangular trenches (notches) 901R are provided in one side surface of the opening 901J with a predetermined interval. In addition, L-shaped ribs are provided in both longitudinal sides of the opening 901J in back of the inclined surface 901H.

The angle adjustment mechanism 910 includes a knob 911, a knob support portion 912, a plate spring 913, a leading end holding portion 914, a plate spring 915, an engagement portion 916, a step portion 917, and a stopper 918.

The knob support portion 912, the plate spring 913, the leading end holding portion 914, the plate spring 915, and the engagement portion 916 are continuously connected along the inner sides of the inclined surface 901H, the front face 901G, the bottom face 901A, and the rear surface 901V of the casing 901.

The knob 911 is fixed to the knob support portion 912 using a screw 911A such that the opening 901J provided in the inclined surface 901H of the casing 901 is interposed between the L-shaped rib provided in back of the opening 901J and the knob support portion 912 held movable on the back surface of the inclined surface 901H.

In the knob support portion 912, a protrusion 912A projecting to the knob 911 side is positioned inside the opening 901J, the inside of the protrusion 912A is made of a plate-like fitting type spring member, and a horn-like spring 912B having a substantially triangular protrusion is arranged to fit into the trench 901R.

In the knob support portion 912, a waterproof packing 912C is provided in the periphery of the upper face so that a liquid is prevented from intruding into the casing 901 from a gap between the knob support portion 912 and the inclined surface 901H.

The leading end holding portion 914 is made of, for example, elastomer having flexibility to seal the opening 901N and is arranged to adjoin the outer circumference of the sheath 311.

The leading end holding portion 914 is fitted to the L-shaped rib provided in the inside of the bottom face 901A, and both sides of the leading end holding portion 914 slip in the longitudinal direction along the inner sides of the front face 901G and the rear surface 901V of the casing 901. By virtue of the flexibility of the leading end holding portion 914, even when the leading end portion 304B of the puncture channel needle 304 and the leading end of the sheath 311 move in the angle adjustment mechanism 910, it is possible to follow such a movement and continuously seal the opening 901N. Therefore, it is possible to prevent a liquid from intruding into the casing 301.

In the leading end holding portion 914, a half-cylindrical slope stopper 914B projects in a vertical direction in front of a cover portion 914A that covers the puncture channel needle 304 and the sheath 311. As a result, even when the leading end holding portion 914 moves to the rear direction, the puncture channel needle 304 and the sheath 311 can obtain an angle of 90°.

An end of the engagement portion 916 opposite to the end connected to the plate spring 915 has a claw portion 916A protruding to the step portion 917 side. The engagement portion 916 is held movably in the longitudinal direction along the step portion 917 using a fixture 918.

The step portion 917 is formed in a substantially triangular prism shape having an inclined surface inclined at a predetermined inclination angle φ (52° in this embodiment) with respect to the upper direction from the front direction to the rear direction in the foremost direction in the inner side of the bottom face 901B. In the step portion 917, a plurality of steps 917A are provided on the inclined surface at the same interval as that of the trench 901R, and the claw portion 916A of the engagement portion 916 is engaged with the step 917A.

In the angle adjustment mechanism 910 configured in this manner, as an initial position, as illustrated in FIG. 31(A), the horn-like spring 912B of the knob support portion 912 is engaged with the uppermost trench 901R of the casing 901, and the claw portion 916A of the engagement portion 916 is engaged with the lowermost step 917A of the step portion 917 such that the protrusion angle of the puncture channel needle 304 and the sheath 311 is set to the smallest angle of 20°.

In the angle adjustment mechanism 910, as a user manipulates the knob 911 to move downward, the horn-like spring 912E of the knob support portion 912 is engaged with the trench 901R of the casing 901 in a creeping manner one by one, and the claw portion 916A of the engagement portion 916 is engaged with the step 917A of the step portion 917 in a creeping manner one by one. As a result, the angle adjustment mechanism 910 slowly increases the protrusion angle of the puncture channel needle 304 and the sheath 311.

In the angle adjustment mechanism 910, as the knob 911 moves to the lowermost step in response to a user's manipulation, a protrusion of the horn-like spring 912E of the knob support portion 912 is engaged with the lowermost trench 901R of the casing 901, and the claw portion 916A of the engagement portion 916 is engaged with the uppermost one of the steps 917A of the step portion 917. In this case, in the angle adjustment mechanism 910, the stopper 918 abuts upon the inner side of the upper face 901F of the casing 901 and sets the protrusion angle of the puncture channel needle 304 and the sheath 311 to 90°.

In the angle adjustment mechanism 910, the protrusion angle of the puncture channel needle 304 and the sheath 311 changes from 20° to 90° between the uppermost step position of the knob 911 and the lowermost step position of the knob 911. In response, a distance between the leading end of the puncture channel needle 304 and the sheath 311 and a lower surface of the leading end holding portion 914 (puncture hole) changes.

Therefore, in the angle adjustment mechanism 910, it is difficult to maintain a constant puncture depth unless the movement distance of the leading end of the puncture channel needle 304 and the sheath 311 is corrected by the changed distance between an assembly of the puncture channel needle 304 and the sheath 311 and the lower surface of the leading end holding portion 914.

In this consideration, the angle adjustment mechanism 910 adjusts the position of the stopper 918. However, the longitudinal movement amount of the leading end holding portion 914 and the movement distances of the leading end of the puncture channel needle 304 and the sheath 311 and the lower surface (puncture hole) of the leading end holding portion 914 are different. Therefore, the movement amount of the stopper 918 is corrected based on the inclination angle of the step portion 917 as following formula (1):

$$\text{movement amount of stopper 918} = (\text{longitudinal movement amount of leading end holding portion 914}) \times \cos \phi \quad (1).$$

It is noted that "ϕ" denotes a puncture angle of 20° (inclination angle of the step portion 917).

In this manner, using the angle adjustment mechanism 910, it is possible to adjust the puncture angle of the puncture channel needle 304 and the sheath 311 against a user's skin surface.

7-5. Alternative 5

In the above-described embodiment, the puncture release mechanism 330 includes the restricting portion 331, the spring 332, and the actuator 333. However, the invention is not limited in this regard. Instead, the puncture release mechanism 330 may be configured such that the support plate 323 is opened based on control of the microcomputer 220.

Figure 32:
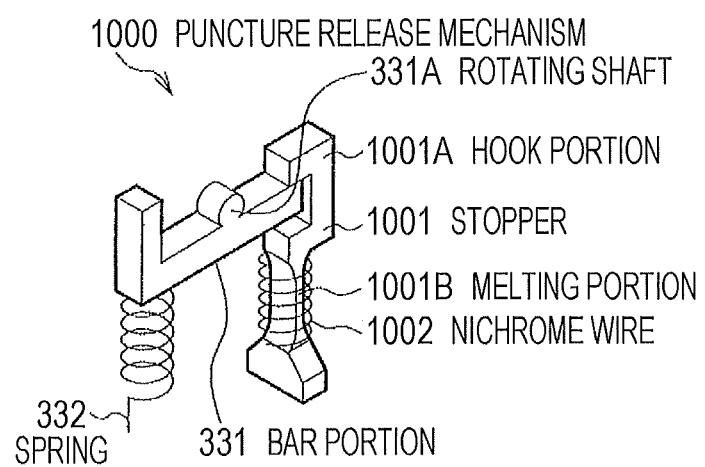
FIG. 32 is a schematic diagram illustrating a puncture release mechanism according to another embodiment.

For example, referring to FIG. 32, the puncture release mechanism 1000 includes a restricting portion 331, a spring 332, a stopper 1001, and a nichrome wire 1002. The restricting portion 331 and the spring 332 are similar to those of the puncture release mechanism 330.

In the stopper 1001, one surface of a substantially U-shaped hook portion 1001A abuts on the upper face of the restricting portion 331 in rear of the rotational shaft 331A such that the rear side of the restricting portion 331 from the rotational shaft 331A is fitted.

The hook portion 1001A is connected to a long and narrow melting portion 1001B and is fixed to the casing 301 through the melting portion 1001B.

In the stopper 1001, the nichrome wire 1002 electrically conducted under control of the microcomputer 220 is wound around the melting portion 1001B by several windings.

The microcomputer 220 performs control such that an electric current flows through the nichrome wire 1002 to melt the melting portion 1001B, when the puncture channel needle 304 and the sheath 311 puncture a user's skin. In this case, in the puncture release mechanism 1000, the restricting portion 331 is released from the stopper 1001, and the restricting portion 331 is rotated counterclockwise with respect to the rotational shaft 331A to recede from the support plate 323 by virtue of a restoring force of the spring 332. As a result, the puncture channel needle 304 and the sheath 311 of the puncture mechanism 320 punctures a user's skin.

7-6. Alternative 6

In the above-described embodiment, a single convex portion 342A is provided in the center portion 342, and a plurality of concave portions 341A are provided in the support portion 341. However, the invention is not limited in this regard. Instead, a plurality of convex portions 342A may be provided in the center portion 342, and a single concave portion 341A may be provided in the support portion 341. In addition, a single or a plurality of concave portions may be provided in the center portion 342, and a plurality of or a single convex portion may be provided in the support portion 341.

7-7. Alternative 7

The description above explains that the side face connecting portions 511D and the 511E are coplanar. However, the invention is not limited in this regard. Instead, the side face connecting portion 511E may be provided in a position higher than that of the side face connecting portion 511D.

As a result, it is possible to prevent a liquid medicine from flowing into the pump 525 when the pump 525 suctions a liquid medicine from the vial 580.

7-8. Alternative 8

The description above describes that the transmitter 221, the receiver 222, and the flow detection control portion 224 have a hardware configuration separate from that of the microcomputer 220. However, the invention is not limited to this as the microcomputer 220 may have a software configuration serving as the transmitter, the receiver, and the flow detection control portion. Alternatively, a part of the transmitter, the receiver, and the flow detection control portion may have a hardware configuration, and other parts may have a software configuration.

The description above describes that the battery monitoring portion 363, the transmitter 367, and the receiver 368 have a hardware configuration separate from that of the microcomputer 361. However, the invention is not limited in this regard as the microcomputer 361 may have a software configuration serving as the battery monitoring portion, the transmitter, and the receiver. Alternatively, a part of the battery monitoring portion, the transmitter, and the receiver may have a hardware configuration, and other parts may have a software configuration.

In the description above, the battery monitoring portion 562, the pump driving portion 563, the plunger driving portion 564, the plunger monitoring portion 565, the absorption amount detection portion 566, the injection amount detection portion 567, and the clamp open/close portion 568 have a hardware configuration separate from that of the microcomputer 361. However, the invention is not limited in this regard as other arrangements or configurations are possible. As another possibility, the microcomputer 560 may have a software configuration serving as the battery monitoring portion, the pump driving portion, the plunger driving portion, the plunger monitoring portion, the absorption amount detection control portion, the injection amount detection control portion, and the clamp open/close portion. Alternatively, a part of the battery monitoring portion, the pump driving portion, the plunger driving portion, the plunger monitoring portion, the absorption amount detection control portion, the injection amount detection control portion, and the clamp open/close portion may have a hardware configuration, and other parts may have a software configuration.

Furthermore, in the above-described embodiment, the clamps 540, 541, and 542 of the liquid-medicine filling device 5 are opened or closed under control of the microcomputer 560. However, the invention is not limited in this way. Instead, a clamp opened/closed by a user may be employed.

The detailed description above describes a liquid-medicine administration device, a puncture device, a liquid-medicine filling device, a liquid-medicine filling method, and liquid-medicine filling system disclosed by way of example. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A puncture device comprising:
   a hollow needle possessing both a tip portion configured to puncture a living body and an elastic portion;
   a fixing portion fixed to a part of the hollow needle so that the part of the hollow needle is a fixed part of the hollow needle, the fixed part of the hollow needle being positioned on a side of the elastic portion opposite the tip portion so that the elastic portion is located axially between the tip portion and the fixed part;
   a sheath portion covering a part of or entirety of the hollow needle from the fixed part to the tip portion, the sheath portion including a plastically deformable elongating member, one end of the sheath portion being located closer to the fixing portion than the tip portion and being fixed to the hollow needle without any gap between an outer periphery of the hollow needle and an inner periphery of the sheath portion;
   a holding portion holding the hollow needle and the sheath portion in an integrated manner, the holding portion being positioned between the tip portion of the hollow needle and the plastically deformable elongating member;
   a holding release mechanism that releases the holding of the holding portion between the hollow needle and the sheath portion after the tip portion of the hollow needle and the sheath portion are punctured into the living body by moving the holding portion in a direction causing the elastic portion to extend; and
   wherein the sheath portion elongates and is held in an elongated condition when the holding portion moves by the holding release mechanism, or when the holding of the hollow needle using the holding portion in an integrated manner is released, and the elastic portion contracts.

2. The puncture device according to claim 1, wherein the sheath portion comprises:
   a sheath covering a part of the hollow needle including the tip portion and a portion of the hollow needle on a tip portion side with respect to the elastic portion; and
   the elongating member covers the elastic portion of the hollow needle and has one end connected to the sheath; and
   the holding portion is fixed to the sheath.

3. The puncture device according to claim 1, wherein the sheath portion covers the hollow needle from a position distal to where the hollow needle is fixed to the fixing portion to the tip portion, and the holding portion is fixed to the sheath portion.

4. The puncture device according to claim 1, wherein the sheath portion comprises:
   a sheath that covers the tip portion of the hollow needle as well as a portion of the hollow needle on a tip portion side of the elastic portion, and
   the elongating member possessing one end connected to the sheath portion and completely covering the elastic portion.

5. The puncture device according to claim 1, comprising:
   a liquid-medicine storage portion configured to store liquid medicine; and
   the hollow needle being in communication with the liquid-medicine storage portion and forming a flow channel through which the liquid medicine stored in the liquid-medicine storage portion flows.

* * * * *